United States Patent
Pyle et al.

(10) Patent No.: US 8,292,975 B2
(45) Date of Patent: *Oct. 23, 2012

(54) METHODS OF REFINING HYDROCARBON FEEDSTOCKS

(75) Inventors: Jason L. Pyle, San Diego, CA (US);
Alex M. Aravanis, San Diego, CA (US);
Daniel Crunkleton, Broken Arrow, OK (US); Geoffrey L. Price, Tulsa, OK (US)

(73) Assignees: Sapphire Energy, Inc., San Diego, CA (US); The University of Tulsa, Tulsa, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/294,999

(22) Filed: Nov. 11, 2011

(65) Prior Publication Data

US 2012/0055081 A1     Mar. 8, 2012

Related U.S. Application Data

(63) Continuation of application No. 12/212,558, filed on Sep. 17, 2008, now Pat. No. 8,075,641.

(60) Provisional application No. 60/973,394, filed on Sep. 18, 2007, provisional application No. 61/085,780, filed on Aug. 1, 2008.

(51) Int. Cl.
*C10L 1/18* (2006.01)
(52) U.S. Cl. ............... 44/307; 44/308; 44/605; 585/240
(58) Field of Classification Search ............ 44/307–308, 44/605; 585/240
See application file for complete search history.

(56) References Cited

U.S. PATENT DOCUMENTS

| 4,300,009 A | 11/1981 | Haag et al. |
| 4,508,930 A | 4/1985 | Wideman et al. |
| 5,186,722 A | 2/1993 | Cantrell et al. |
| 8,075,641 B2* | 12/2011 | Aravanis et al. ............... 44/307 |
| 2004/0074760 A1 | 4/2004 | Portnoff et al. |
| 2008/0083158 A1 | 4/2008 | Renninger et al. |

FOREIGN PATENT DOCUMENTS

| WO | WO 2009/008893 A1 | 1/2009 |
| WO | WO 2009/025635 A1 | 2/2009 |

OTHER PUBLICATIONS

Tracy, N.I. et al. (2011). Biomass and Bioenergy, 35, 1060-1065.*
Tracy, N.I. et al. (2010). Fuel, 89, 3493-3497.*
Elias, et al. "Sesquiterpenoids in sediments of a hypersaline lagoon: A possible algal origin." Org. Geochem. 1997, vol. 26, 11-12, pp. 721-730.
Hillen et al., "Hydrocracking of the oils of *Botryococcus braunii* to transport fuels," Biotechnology and Bioengineering 1982, vol. XXIV, pp. 193-205.
Milne et al., "Catalytic conversion of microalgae and vegetable oils to preumium gasoline, with shape-slective zeolites,"Biomass 1990 vol. 21; 219-232.
Ruchardt et al., "Towards an understanding of the carbon-carbon bond." Agnew. Chem. Int. Ed. Engl. 1980 vol. 19, 429-440.

* cited by examiner

*Primary Examiner* — Brian McCaig

(57) ABSTRACT

Processes of converting to feedstocks comprising hydrocarbons to compositions comprising light hydrocarbon products are described herein. Also described are processes and methods of producing and refining compositions comprising terpenes from biomass that can be suitable as a fuel product.

20 Claims, 30 Drawing Sheets

METHODS OF REFINING HYDROCARBON FEEDSTOCKS

CROSS-REFERENCE

This application is a continuation of and claims the benefit of U.S. patent application Ser. No. 12/212,558 (filed Sep. 17, 2008) now U.S. Pat. 8,075,641 which claims the benefit of U.S. Provisional Patent Applications Nos. 60/973,394 (filed Sep. 18, 2007) and 61/085,780 (filed Aug. 1, 2008) which applications are incorporated herein by reference.

BACKGROUND OF THE INVENTION

Carbon-based fossil fuels, such as coal, petroleum and natural gas, are finite and non-renewable resources. At the current consumption rate, supplies of fossil fuels will be exhausted in the foreseeable future. In the meantime, burning fossil fuels has resulted in a rise in the concentration of carbon dioxide in the atmosphere, which is believed to have caused global climate change.

Biofuels are viable alternatives to fossil fuels for several reasons. Biofuels are renewable energy sources produced from biomass, a material derived from recently living organisms. Although biofuels are also carbon-based, they do not cause a significant net increase in atmospheric carbon dioxide levels because the carbon dioxide released during the fuel consumption is reabsorbed through new growth of the organisms.

Because transportation-related gasoline consumption represents the majority of all liquid fossil fuel use, supplementing or replacing gasoline with liquid biofuels is expected to reduce our reliance on fossil fuels and carbon dioxide production. Currently available liquid biofuels include ethanol and lipids. Ethanol is typically produced from crops rich in carbohydrates such as sugar and starch. Complex carbohydrates such as cellulose and hemicellulose can also be broken down into sugar, which can then be converted to ethanol by microorganisms. Lipids-based biofuels, also called biodiesels, are vegetable oils derived from vegetables such as corn, soybean, sunflower, and sorghum.

The energy benefit of using ethanol and lipid-based biofuels has, however, been called into question. Ethanol has lower energy content than gasoline such that more ethanol is required to provide the same energy output. More significantly, both ethanol and lipid productions are currently driven by fossil fuel. For example, the energy for producing ethanol includes running farm machinery and irrigation, transporting and grinding the crop, producing pesticides and fertilizer and fermenting and distilling ethanol. There have been concerns that the energy input for ethanol production may exceed the energy output from the combustion of ethanol. In addition, widespread production and use of ethanol and biodiesel will require constructing new distribution pipelines because neither is suitable for transportation using existing fuel-distribution infrastructure. Moreover, any large-scale development of crop-based fuels such as ethanol and traditional biodiesel will compete for the same resources as food production, and ultimately be limited by the amount of arable land.

Accordingly, there is a need for producing fuels from renewable sources, as well as overcoming the drawbacks of existing biofuels.

SUMMARY OF THE INVENTION

Disclosed herein is a catalytic cracking process for cracking a sesquiterpene, the process comprising contacting under catalytic cracking conditions a feedstock containing the sesquiterpene with a catalytic composition. The sesquiterpene, for example, can be cuparene or farnesene. The process can comprise producing a mixture comprising percentages by weight of greater than 50% toluene, less than 2% benzene, less than 20% xylene, and greater than 30% of a combination of cyclohexanes and cyclopentanes. In another instance, the process comprises producing a mixture comprising percentages by weight of greater than 15% toluene and greater than 10% paraffins. In some instances, the cracking conditions comprise heating the feedstock to greater than 350 C, and wherein said process comprises producing a mixture comprising percentage by weight of greater than 75% of components with an octane number greater than 90. Also, a mixture as described can comprise percentages by weight of about 15% to about 20% toluene and about 10% to about 15% paraffins. A mixture can also percentages by weight of greater than 50% aromatic hydrocarbons.

In another aspect, a catalytic cracking process is provided for cracking a diterpene, the process comprising contacting under catalytic cracking conditions a feedstock containing the diterpene with a catalytic composition. In an instance, the diterpene is phytol. The process can comprise producing a mixture comprising percentage by weight of greater than 55% C5-C9 paraffins, wherein more than 70% by weight of the paraffins are mono-methyl paraffins. In some instances, cracking conditions comprise heating the feedstock to greater than 350 C, and wherein said process comprises producing a mixture comprising percentage by weight of greater than 75% of components with an octane number greater than 90. In some instances, the mixture comprises percentages by weight of greater than 40% methylbutane. The mixture can also comprise percentage by weight of less than 1% C4 paraffins.

In yet another aspect, a catalytic cracking process is provided herein for cracking a triterpene, the process comprising contacting under catalytic cracking conditions a feedstock containing the triterpene with a catalytic composition. The triterpene can be squalene.

Also provided is a catalytic cracking process for cracking a tetraterpene, the process comprising contacting under catalytic cracking conditions a feedstock containing the triterpene with a catalytic composition. The tetraterpene can be carotene.

In an aspect, a catalytic cracking process is provided herein for cracking a mixture comprising at least three terpenes, the process comprising contacting under catalytic cracking conditions a feedstock containing the mixture comprising at least three terpenes with a catalytic composition. The at least three terpenes can be sesquiterpenes. In an instance, the feedstock contains ginger oil. The process can produce a mixture comprising percentages by weight of greater than 15% naphthenes, greater than 20% paraffins, greater than 5% xylenes, and greater than 5% toluene. The mixture can also comprise at least three terpenes of different sizes selected from the group consisting of the following: monoterpenes, sesquiterpenes, diterpenes, triterpenes, and tetraterpenes. A process can further comprise extracting the mixture comprising at least three terpenes from algae.

In another aspect, a catalytic cracking process is provided for cracking oil from algae, the process comprising: extracting oil from algae to form a feedstock comprising a terpene; contacting under catalytic cracking conditions the feedstock containing the terpene with a catalytic composition. In some instances, the process further comprises genetically modifying the algae prior to the extracting oil. Genetically modifying the algae can produce increased amounts of the terpene compared to not genetically modifying the algae. In some instances, the process further comprises mixing the oil from algae with a fuel component prior to contacting the feedstock. For example, a fuel component is selected from the group consisting of the following: fossil fuel, petroleum, a mixture for fuel blending, gasoline, diesel, jet fuel, and any combination thereof. The terpene can be, for example, a sesquiterpene, diterpene, triterpene, tetraterpene, cuparene, farnesene, phytol, squalene, or carotene.

In some instances, a catalytic cracking process comprises cracking conditions wherein the cracking conditions comprise heating the feedstock to between about 100-1000 C. In further instances, the catalytic cracking conditions include heating the feedstock to a temperature between about 180 and 580 C or between about 200 and 400 C or between about 350 and 400 C.

In some instances, a catalytic cracking process comprises contacting a feedstock with a catalytic composition comprising a molecular sieve. The molecular sieve can be a large pore molecular sieve having a pore size greater than 6 Angstrom and/or have a cage diameter of 10-15 angstroms. In some instances, the large pore molecular sieve is a 12-ring zeolite, such as a β-type, L-type, Y-type, LZY-72, Valfor CP811BL-25, ELZ-L, or T-4546. In other instances, the molecular sieve is a 10-ring zeolite, such as a ZSM-5 zeolite. In some instances the catalytic composition comprises more than one molecular sieve. For example, the catalytic composition further comprises a second molecular sieve that can be a different size than the molecular sieve.

In an aspect, a process of refining is described herein that comprises cracking a feedstock comprising squalene in a flow reactor; distilling the cracking product; and obtaining a fuel product with an octane rating between about 85 to 125. In some instances, the octane rating is greater than 90.

Also provided herein is a method for making a fuel product comprising: obtaining a feedstock from a genetically modified non-vascular photosynthetic organism; and contacting under catalytic cracking conditions the feedstock with a catalytic composition thereby making a fuel product, wherein the catalytic composition comprises a large pore molecular sieve having a pore size greater than 6 Angstrom. The cracking can occur at a temperature up to 420 C. The catalytic composition can be a 12 ring zeolite. The fuel product can have an octane number of between about 85 to 125 or can have an octane number of greater than 90. In some instances, the method further comprises adding a fuel component to the fuel product, wherein the fuel component is ethanol, jet fuel, diesel, biodiesel, or gasoline. In some instances, the method further comprises adding a fuel additive to the fuel product.

In an aspect, a composition is provided that comprises: oil extracted from algae and a catalytic cracking composition. Also provided is a composition comprising: a terpene and a catalytic cracking composition, wherein the terpene can be selected from the group consisting of the following: a monoterpene, a sesquiterpene, a diterpene, a triterpene, a tetraterpene, cuparene, farnesene, squalene, zingerene, and carotene. Other compositions described herein include a composition comprising: ginger oil and a catalytic cracking composition and a composition comprising: phytol and a catalytic cracking composition. The catalytic cracking composition is a molecular sieve. In some instances, the molecular sieve is a large pore molecular sieve having a pore size greater than 6 Angstrom and/or a cage diameter of 10-15 angstroms. In some instances, the large pore molecular sieve is a 12-ring zeolite, such as a β-type, L-type, Y-type, LZY-72, Valfor CP811BL-25, ELZ-L, or T-4546. In other instances, the molecular sieve is a 10-ring zeolite, such as a ZSM-5 zeolite.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Many novel features of the invention are set forth with particularity in the appended claims. A better understanding of exemplary features and advantages of the invention will be obtained by reference to the following detailed description that sets forth illustrative embodiments, in which many principles of the invention are utilized, and the accompanying drawings of which:

DETAILED DESCRIPTION OF THE INVENTION

Figure 1A:
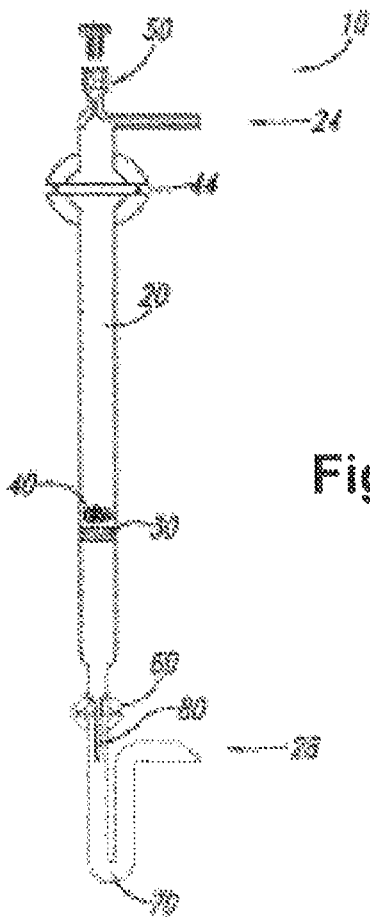
FIG. 1A shows a pulse reactor for carrying out catalytic reactions and evaluating product distribution.

Refining a hydrocarbon mixture can be performed to optimize the types, shapes, and sizes of the hydrocarbon mixture to produce a fuel product. Typical refining processes in the fuel industry include, but are not limited to, distillation, fractionation, extraction, solvent extraction, hydrotreatment, isomerization, dimerization, alkylation, and cracking. A cracking process typically refers process that breaks down hydrocarbons into smaller hydrocarbons, for example, by scission of a carbon-carbon bond. Complex organic molecules such as isoprenoids or heavy hydrocarbons can be cracked into simpler molecules (for example light hydrocarbons) by the breaking of carbon-carbon bonds in the precursors. Cracking is commonly performed by using high temperatures, catalysts, or a combination thereof. Example cracking methods include, but are not limited to, thermal cracking, fluid catalytic cracking, thermofor catalytic cracking, catalytic cracking, steam cracking, and hydrocracking.

Catalytic cracking processes can involve scission of an organic molecule in the presence of a catalyst, typically an acid catalyst such as silica-alumina catalyst or zeolites. Catalysts promote a heterolytic (asymmetric) breakage of bonds yielding pairs of ions of opposite charges, usually a carbocation and a very unstable hydride anion. Carbon-localized free radicals and cations are both highly unstable and undergo processes of chain rearrangement, for example C—C scission in the beta position and also intra- and intermolecular hydrogen transfer or hydride transfer. In both types of processes, the corresponding reactive intermediates (radicals, ions) are permanently regenerated, and thus the reaction can proceed by a self-propagating chain mechanism. The chain of reactions can then be eventually terminated by radical or ion recombination.

In an embodiment, the catalytic cracking process and catalytic cracking conditions comprise contacting an organic molecule with a molecular sieve, for example a zeolite. Catalytic cracking conditions can also comprise heating an organic molecule, for example from 100-1000° C. In an embodiment, cracking conditions comprise heating a feedstock to between about 100-1000° C. Further, catalytic cracking conditions comprise heating a feedstock to between about 180 and 580° C. In yet another embodiment, catalytic cracking conditions include heating the feedstock to a temperature between about 200 and 400° C. or a temperature between about 350 and 400° C. Catalytic cracking conditions can comprise heating a feedstock to a temperature wherein C—C bond scission is encouraged in the presence of a catalyst.

In an aspect, a catalytic cracking process is disclosed for cracking a terpene, the process comprising contacting under catalytic cracking conditions a feedstock containing the terpene with a catalytic composition.

Terpenes are a large and varied class of hydrocarbons, produced primarily by a wide variety of photosynthetic organisms. When terpenes are modified chemically, such as by oxidation or rearrangement of the carbon skeleton, the resulting compounds are generally referred to as terpenoids or isoprenoids. Terpenoids or isoprenoids generally comprise a heteroatom. As referred to herein the term terpene can be used to describe terpenoids or isoprenoids.

Terpenes can be the primary constituents of the essential oils of many types of plants and flowers. Essential oils are used widely as natural flavor additives for food, as fragrances in perfumery, and in traditional and alternative medicines such as aromatherapy. Synthetic variations and derivatives of natural terpenes also greatly expand the variety of aromas used in perfumery and flavors used in food additives.

Terpenes are a diverse class of biosynthetic hydrocarbons comprising multiple units of isoprene (2-methyl-buta-1,3-diene), which is a five-carbon hydrocarbon. The isoprene units can be linked together to form acyclic (including branched or linearly arranged carbon atoms) or cyclic framework. Among these, hemiterpenes consist of one isoprene unit (for example isoprene), monoterpenes consist of two isoprene residues and include, for example, limonene and myrcene; sesquiterpenes consist of three isoprene residues and include, acyclic sesquiterpenes (for example, farnesene) and cyclic sesquiterpenes (for example, cuparene, curcumene, zingiberene and bisabolene); and diterpenes consist of four isoprene residues and include, for example, cembrene, taxadiene; triterpenes consist of six isoprene residues and include, for example, squalene, and tetraterpenes consist of eight isoprene residues and include, for example, carotene, the acyclic lycopene, the monocyclic γ-carotene, and the bicyclic α- and β-carotenes. The size of an isoprenoid refers to the total number of the carbon atoms of the isoprenoid framework, and is typically a multiplicity of five. Table 1 shows exemplary terpenes that are suitable substrate or feedstock for refining.

TABLE 1

| Name | Structure | Size | CAS | MW |
|---|---|---|---|---|
| isoprene | 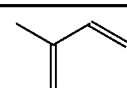 | 5 | | 68.1 |
| myrcene | 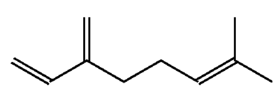 | 10 | | 136.2 |
| ocimene | 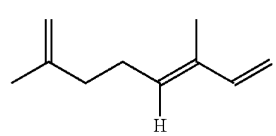 | 10 | 13877-91-3 | 136.2 |
| limonene | 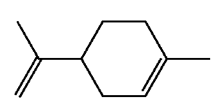 | 10 | | 136.2 |

TABLE 1-continued
| Name | Structure | Size | CAS | MW |
|---|---|---|---|---|
| terpinolene | 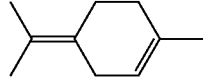 | 10 | 586-62-9 | 136.2 |
| phellandrene | 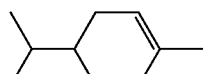 | 10 | 99-83-2 | 136.2 |
| farnesene | 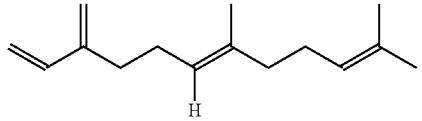 | 15 | | 204.3 |
| cuparene | 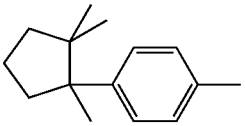 | 15 | | 202.3 |
| cuprenene | 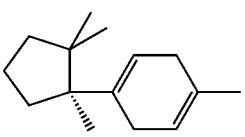 | 15 | 5046-93-5 | 204.4 |
| isobazzanene | 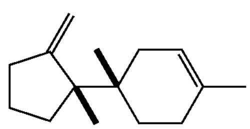 | 15 | 88661-59-0 | |
| sesquiphellandrene | 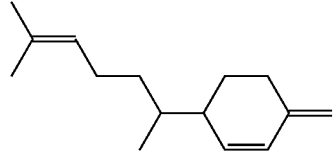 | 15 | 20307-83-9 | 204.4 |
| bisabolene | 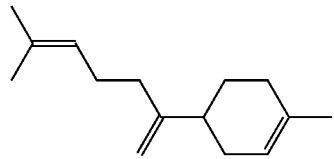 | 15 | 495-61-4 | 204.3 |
| curcumene | 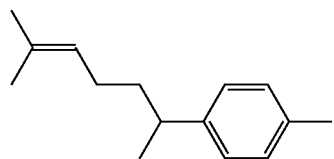 | 15 | 28976-68-3 | 202.3 |
| zingiberene | 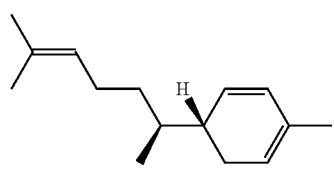 | 15 | 495-60-3 | 204.3 |

TABLE 1-continued

| Name | Structure | Size | CAS | MW |
|---|---|---|---|---|
| barbatene | 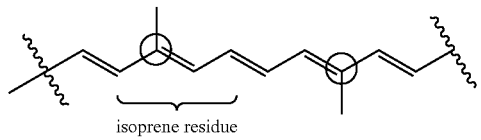 | 15 | 53060-59-6 | 204.3 |

In some embodiments, the hydrocarbon has a polyene structure. As used herein, "polyene" refers to a hydrocarbon having a main carbon-based backbone wherein the carbon atoms are linearly joined by single and double bonds. The main carbon-based backbone refers to a longest straight-chain of the hydrocarbon structure and comprises at least two double bonds. One or more carbon atoms that form the backbone can be further substituted with alkyl groups, in particular, with methyl groups. The polyene can exhibit both E and Z (cis and trans, respectively) geometric isomers. In some embodiments, the polyene includes terminal cyclic structures (for example, cyclohexenyl or substituted cyclohexenyl) at one or both ends of the carbon-based backbone.

In one embodiment, the polyene structure comprises at least one "quaternary olefinic carbon", which refers to a carbon atom of a polyene backbone that is connected to two adjacent carbon atoms of the polyene backbone via a C═C bond and a C—C bond, respectively. The quaternary olefinic carbon is further connected to an alkyl substituent (for example, a methyl). A representative quaternary olefinic carbon is shown below:

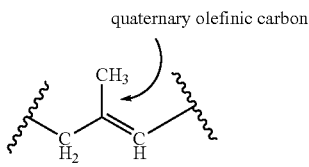

quaternary olefinic carbon

Quaternary olefinic carbon is typically present in an isoprene derivative such as terpenes. As discussed, isoprene residue is a common structural motif in biological systems. Many biological derivatives of isoprene, such as carotenoids, are chain elongation products of multiple isoprene residues.

Thus, in some embodiments, the polyene chain comprises two or more repeating units of isoprene residues to provide an isoprenoid. An exemplary structure of a polyene backbone segment having three repeating units of isoprene residues is shown below, in which the quaternary olefinic carbons are indicated in circles.

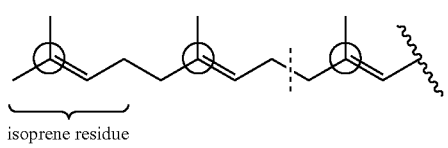

isoprene residue

Depending on how the isoprene units are connected, the polyene chain may comprise an alternative arrangement of the isoprene residues. As shown below, the polyene segment comprises alternating C—C bonds and C═C bonds to provide a conjugated structure. An exemplary structure of a conjugated backbone segment is shown below, in which the quaternary olefinic carbons are indicated in circles:

isoprene residue

In an aspect, a catalytic cracking process for cracking a sesquiterpene, the process comprising contacting under catalytic cracking conditions a feedstock containing the sesquiterpene with a catalytic composition. The sesquiterpene can be part of a mixture of organic molecules or can be a mixture comprising greater than 75% sesquiterpene. A sesquiterpene is any organic molecule comprising three isoprene units. Sesquiterpenes are a class of terpenes that consist of three isoprene units and are C15 molecules. Like monoterpenes, sesquiterpenes may be acyclic or contain rings, including many unique combinations. Biochemical modifications such as oxidation or rearrangement produce sesquiterpenes known as sesquiterpenoids. For the purposes of this disclosure, the term sesquiterpene includes sesquiterpenoids or other organic molecules comprising three isoprene units as well as additional atoms, such as oxygen. Sesquiterpenes include, for example without limitation, cuparene, farnesene, and zingiberene.

A sesquiterpene can be cracked using a process described herein by heating a sesquiterpene or a mixture comprising a sesquiterpene in a reactor. For example without limitation, the reactor can be a pulse reactor, plug flow reactor, or a continuous flow reactor. A catalyst, for example a zeolite catalyst, can be pretreated with a gas until the desired atmosphere and catalyst is obtained. For example, helium (inert atmosphere), hydrogen (reducing atmosphere), or oxygen (oxidizing atmosphere) can be used to pretreat a catalyst in the reactor. After the optional pretreatment of a catalyst, the reactor can be maintained at the desired reaction temperature, for example, the temperature of the cracking conditions. In an exemplary embodiment using a pulse reactor, small quantities of the sesquiterpene are pulsed through the reactor over the catalyst. Depending on the temperature and the catalyst used for the reaction, different products from the cracking reaction can be generated. Optionally, after the reaction has proceeded, the reaction products can be identified by, for example, gas chromatography and/or mass spectrometry (GC/MS). Other atom identification techniques can also be used as would be obvious to one skilled in the art.

A catalytic composition can comprise an acidic catalyst, for example, a molecular sieve. A molecular sieve is a material containing pores of a precise and uniform size that can be used as an adsorbent for gases and liquids or to trap organic molecules. Molecules small enough to pass through the pores are adsorbed while larger molecules are not. It is different from a common filter in that it operates on a molecular level. For instance, a water molecule may be small enough to pass through while larger molecules are not. In an embodiment, the molecular sieve is a zeolite. A zeolite is an aluminosilicate, aluminophosphate, aluminosilicophosphate, or other oxide that has a microporous or mesoporous structure.

Cracking catalysts such as zeolites typically provide numerous BrØnsted acid sites. Under such an acidic condition, the quaternary olefinic carbon of the biomass polyene can be converted to a tertiary carbenium ion (shown in Scheme N). As used herein, "tertiary carbenium ion" (or simply "carbenium ion") refers to a trivalent carbocation that is connected to three other carbons.

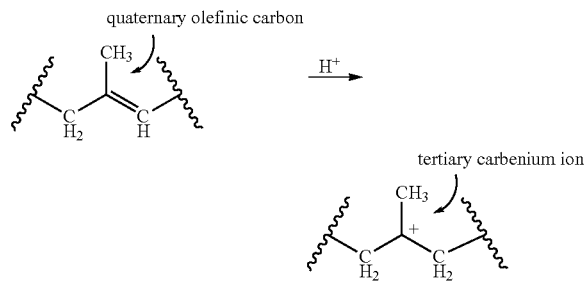

Scheme IV

It is believed that the tertiary carbenium ion is a reactive intermediate that induces carbon-carbon bond scission. As shown in Scheme V, as the carbon-carbon bond at the β-position of the carbenium ion ruptures, the bond electrons neutralize the carbenium ion.

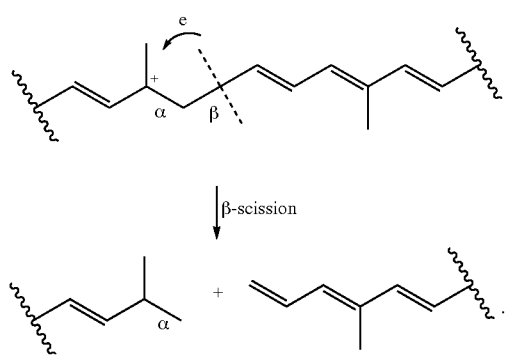

Scheme V

Moreover, the reactive carbenium ions may also lead to isomerization and oligomerization. Accordingly, the carbenium intermediates resulting from the quaternary olefinic carbons play an important role in transforming the polyene-based feedstock into diverse products.

As discussed in more detail herein, zeolites are widely used for cracking processes, and they are especially useful for the production of fuels because of shape selectivity. N. Y. Chen et al., Shape Selective Catalysis in Industrial Applications, Marcel Dekker, New York, 1996. Shape selectivity refers to the property of zeolites arising from their precisely defined pore structure, which results in products of rather narrowly defined molecular weights and structures.

Typically, catalytic scissions produce light olefins or light alkanes, which are shorter segments of the polyene structure. Depending on the actual structure and the point of scission, the light olefin may be a short acyclic chain of the polyene or may comprise a cyclic structure (for example, cyclohexenyl). In various embodiments, the light olefins comprise between 3 to 15 carbons, more typically, between 3-12 carbons.

Any catalyst suitable for catalytic cracking in petroleum refinery processes can be used in combination with a feedstock. While commercial cracking catalysts include acid-treated natural aluminosilicates, amorphous synthetic silica-alumina combinations, and crystalline synthetic silica-alumina (zeolites), the most widely used commercial catalytic cracking catalysts are the zeolites.

Zeolites are aluminosilicate, aluminophosphate, aluminosilicophosphate, or other oxide members of a family of microporous solids known as molecular sieves. The term molecular sieve refers to a particular property of these materials, for example the ability to selectively sort molecules based primarily on a size exclusion process. This is due to a very regular pore structure of molecular dimensions. The maximum size of the molecular or ionic species that can enter the pores of a zeolite is controlled by the diameters of the tunnels. More than 1500 zeolite types have been synthesized and 48 naturally occurring zeolites are known. Typically used zeolites are from the faujasitic family, for example, X-, Y-zeolites, pentasils such as ZSM-5, or other zeolites such as zeolite beta and zeolite L. Such zeolitic catalysts and their manufacture are within the knowledge of one skilled in the art.

The hydrogen form of a zeolite (prepared by ion-exchange) is a powerful solid-state acid, and can facilitate a number of acid-catalyzed reactions, such as isomerization, alkylation, and cracking. More specifically, zeolites confine the hydrocarbons in small spaces which cause the hydrocarbons to change their structures or reactivity, such as being converted from quaternary olefinic carbons to carbenium intermediates.

The pore size of the zeolite catalyst can be important in controlling the catalytic reactions, both kinetically and chemically. Accordingly, in selecting a suitable zeolite catalyst, the size of the hydrocarbons to be cracked needs to be taken into consideration. In addition, the pore size may affect the selectivity of a cracking process of a given hydrocarbon feedstock. Other possible types of acid cracking catalyst include mineral acids and organic acids.

During catalytic cracking, intermediate cations from the hydrocarbons may be less reactive and more stable than in other cracking processes. This can allow the cations to accumulate at an active site of a catalyst, which may generate deposits of carbonaceous products generally known as coke. Such deposits may need to be removed (for example by controlled burning) in order to restore catalyst activity.

In addition to catalytic cracking, other industrial cracking processes such as thermal, hydro, and steam cracking conditions can also cause carbon-carbon scission in a polyene structure. These cracking processes do not necessarily involve a carbenium intermediate; instead, carbon-carbon bond scissions may occur indiscriminately along the polyene backbone to produce light olefins.

A process as described herein can comprise contacting a terpene, for example a sesquiterpene, with a zeolite catalytic composition. In an embodiment, the zeolite is a 10-ring zeolite with a pore size of less than 6 Angstroms. An exemplary 10-ring zeolite is a ZSM-5. In an embodiment, the zeolite is SN27.

In another embodiment, a process comprises contacting a terpene with a large pore molecular sieve. For example, a molecular size with a pore size greater than 6 Angstrom. In an example, a large pore molecular sieve has a cage diameter of 10-15 angstroms. The large pore molecular sieve can be a 12-ring zeolite or a zeolite larger than a 12-ring zeolite. In an embodiment, the 12-ring zeolite is a β, L, or Y-type zeolite.

Examples of zeolites useful with a process described herein include, but are not limited to, LZY-72, Valfor CP811BL-25, ELZ-L, and T-4546. A catalytic composition can be converted to it's fully protonated form via ammonium exchange before use. In an embodiment, nickel containing material can be prepared by exchanging the protonated zeolites with Ni(II) acetate aqueous solutions such that 20% and 80% theoretical proton replacement by nickel cations results. In another embodiment, a catalytic composition can be ion-exchanged to yield the ammonium form of the zeolite, which upon heating can convert to the proton form with the elimination of ammonia. A proton form of a zeolite acts as a strong solid acid for catalytic reactions.

A catalytic cracking process for cracking a terpene, for example a sesquiterpene can also comprise contacting the terpene with the catalytic composition and a second catalytic composition. The second catalytic composition can be the same as or different than the first catalytic composition. For example, if a 12-ring zeolite is utilized as the first catalytic composition, a 10-ring or 12-ring zeolite can be used as a second catalytic composition. This can be useful in a variety of ways, for example, when cracking a mixture of hydrocarbons, wherein the hydrocarbons may be different sizes. In another example, a second catalytic composition can be used that is of the same type or size as the first catalyst to crack any remaining larger hydrocarbons or feedstock that did not crack using the first catalytic composition.

In an aspect, a catalytic cracking process is disclosed for cracking cuparene. Cuparene is a sesquiterpene. In an embodiment, cracking is achieved by contacting a feedstock containing cuparene under catalytic cracking conditions with a catalytic composition. Cuparene can be cracked in a reactor, for example a pulse reactor or a continuous flow reactor. The reactor can provide catalytic cracking conditions comprising a heating the reactor and cuparene to a catalytic cracking temperature, for example, 100-1000 C, 180-510 C, 200-400 C or 350-400 C. For example, cuparene can flow through a reactor comprising the catalytic composition, the reactor is heated to a catalytic cracking condition temperature. Cuparene that contacts the catalytic composition is cracked into smaller hydrocarbons than the original C15 cuparene molecule. Example catalysts include those described herein, such as SN27 (ZSM-5 type), ELZ-L (zeolite-L type), and LZY-72 (zeolite-Y type).

Cuparene has a boiling point of about 275 C and may require an adjustment of techniques to measure its presence after a reaction with a gas chromatography column. In an embodiment, adjustments can be made to the column so that cuparene analysis does not contribute to incorrect mass spectrometry analysis.

In an embodiment, cuparene is flowed through a reactor comprising a catalytic composition with a carrier gas (for example helium). A feedstock comprising cuparene can be in the liquid or gaseous phase.

In an embodiment, cuparene is cracked in a process provided herein by contacting the cuparene with a large pore molecular sieve such as β, L, or Y-type zeolite. Because cuparene is a larger hydrocarbon (C15), a large pore molecular sieve may provide for higher conversion of cracking a cuparene molecule into smaller hydrocarbons.

In some embodiment, a process of cracking cuparene produces a mixture comprising percentages by weight of greater than 50% toluene, less than 2% benzene, less than 20% xylene, and greater than 30% of a combination of cyclohexanes and cyclopentanes. In another embodiment, a process of cracking cuparene produces a mixture comprising greater than 50, 60, or 70% toluene. Toluene is a hydrocarbon with a high octane number, and therefore, can be a valuable component of a fuel composition. In an embodiment, the cracked products of cuparene are blended or added to a base fuel to generate a fuel product.

In an aspect, a catalytic cracking process is disclosed for cracking farnesene. Farnesene is a family of sesquiterpenes, with three isoprene units. In an embodiment, farnesene is cracked using a catalytic composition as described herein. For example, farnesene can be cracking using a 12-ring zeolite catalyst, such as LZY-72. In an embodiment, a feedstock comprising farnesene is cracked. The feedstock can comprise more than 50, 60, 70, 80, or 90% farnesene by weight. A feedstock can also comprise other molecules and hydrocarbons, such as bisabolene and curcumene. In an embodiment, farnesene is cracked under cracking conditions comprising temperatures of about 200 to about 50° C. For example, farnesene can be cracked around 350 C.

A process of cracking farnesene can comprise producing a mixture comprising percentages by weight of greater than 15% toluene and greater than 10% paraffins. In an embodiment, the mixture comprises percentages by weight of about 15% to about 20% toluene and about 10% to about 15% paraffins. In another embodiment, the mixture comprises percentages by weight of greater than 50% aromatic hydrocarbons. In an embodiment, more than 50, 60, 70, 75, or 80% of the mixture by weight from cracking farnesene can comprise hydrocarbons with an octane number greater than 90. A mixture can be used as a fuel product, blended with a fuel product, or refined to generate a fuel product. A high octane number mixture or fuel product can be used as fuel product, or for example, as a fuel product for blending into a fossil fuel based fuel.

In another aspect, a catalytic cracking process is described herein for cracking a mixture comprising at least three sesquiterpenes, the process comprising contacting under catalytic cracking conditions a feedstock containing the mixture comprising at least three sesquiterpenes with a catalytic composition. A mixture of sesquiterpenes can crack into a suitable array of hydrocarbons for producing a fuel product or additive, such as jet fuel, gasoline, or diesel. Also, by cracking a mixture of sesquiterpenes, the diversity of the cracking products may allow for the creation of a complete fuel. In another embodiment, a process of cracking a mixture containing all or mostly all of one type of sesquiterpene can also be used to generate a complete fuel.

As an example, the mixture comprising at least three sesquiterpenes can be ginger oil. Ginger oil can comprise molecules including, but not limited to, zingiberene, β-sesquiphellandrene, bisabolene, farnesene, β-phelladrene, cineol, curcumene, and citral.

Ginger oil can be cracked by a process comprising adding carbon dioxide to remove gingerol from the ginger oil. A fully protonated catalyst such as a 12-ring zeolite like LZY-72 can be used to contact the ginger oil to initiate the cracking process and the scission of carbon-carbon bonds of the sesquiterpenes under catalytic cracking conditions.

In an embodiment of a process of cracking ginger oil, the process produces a mixture comprising percentages by weight of greater than 15% naphthenes, greater than 20% paraffins, greater than 5% xylenes, and greater than 5% toluene. Many of the paraffins of the mixture can be branched paraffins which can have a high octane number. The high octane number of many of the components of ginger oil can be used to as a fuel product such as gasoline or a gasoline additive.

In an aspect, a composition is disclosed herein that comprises zingerone and percentages by weight of greater than 15% naphthenes, greater than 20% paraffins, greater than 5% xylenes, and greater than 5% toluene. Zingerone is a product of heating gingerol and can be present in the composition in trace amounts.

In another aspect, a catalytic cracking process for cracking a triterpene is disclosed, the process comprising contacting under catalytic cracking conditions a feedstock containing the triterpene with a catalytic composition. A triterpene is a C30 terpene comprising six isoprene units. An non-limiting example of a triterpene for use in a process is squalene. Squalene is a natural organic compound originally obtained for commercial purposes primarily from shark liver oil, though there are botanic sources as well, including amaranth seed, rice bran, wheat germ, and olives. Most higher organisms produce squalene, including humans. Squalene is a hydrocarbon and a triterpene. Squalene can also be generated from a genetically modified organism in which an organism that does not naturally produce squalene is modified to produce squalene, or an organism that naturally produces squalene is modified to upregulate squalene. For example, an algal cell can be transformed to produce an enzyme that produce squalene through the MVA or MEP pathway and the squalene produced from the algal cell can be cracked using a process described herein.

In an embodiment, a process of cracking squalene can comprise contacting the squalene under catalytic cracking conditions with a catalytic composition, such as a protonated 12-ring zeolite.

In another example of cracking squalene, a process of refining comprises cracking a feedstock comprising squalene in a flow reactor; distilling the cracking product; and obtaining a fuel product with an octane rating between about 85 to 125. In an embodiment, the octane rating of the fuel product is greater than 90. Squalene can be cracked in any suitable reactor as would be known to one skilled in the art. In an example, squalene is cracked in a tubular reactor comprising a pump that allows batches of liquid to be fed to that reactor at a constant, programmable rate. The pump can also allow for the flow of carrier gas or other gases needed to be fed to the reactor, such as helium and nitrogen. In the example, the tubular reactor can be packed with a catalytic composition and the feedstock to be cracked is fed over the catalytic composition. The catalytic cracking conditions in the reactor can be set to an appropriate temperature as determined by the user, for example, 300-500 C. Reaction products from the cracking can be collected at the output of the reactor, for example, by a condensation device. Cracking products can then be identified as described herein. In addition, fractionation, such as distillation can be carried out to further refine the cracking products.

In yet another aspect, a catalytic cracking process is disclosed herein for cracking a diterpene, the process comprising contacting under catalytic cracking conditions a feedstock containing the diterpene with a catalytic composition. A diterpene is a C20 terpene comprising four isoprene unit. As a non-limiting example, phytol can be present in the feedstock to be cracked. Phytol is a natural terpene alcohol that is produced during the break down of chlorophyll. Phytol can be extracted from a plant organism for the cracking methods as described herein. In an embodiment, an organism is genetically modified to upregulate phytol production. For example, an algal cell can be genetically modified to upregulate phytol, the amount of chlorophyll in the cell, and/or a breakdown of chlorophyll in the cells.

Phytol can be cracked catalytically using a zeolite catalyst, such as a Y, L, or β-type zeolite. In an embodiment, cracking phytol under a condition of a temperature of about 350 C produces no measurable quantity or less than 1% by weight benzene cracking product. When producing a fuel product, such as gasoline, it can be favorable to avoid the production of benzene due to regulations. Analysis of phytol cracking products can be performed as described previously herein, such as by GC/MS.

In an embodiment, the process of cracking phytol comprises producing a mixture comprising percentage by weight of greater than 55% C5-C9 paraffins, wherein more than 70% by weight of the paraffins are mono-methyl paraffins. In another embodiment the process comprises producing a mixture comprising percentage by weight of greater than 75% of components with an octane number greater than 90.

In an embodiment, a process of cracking phytol further comprises extracting phytol from an oil. For example, using an organic solvent to extract phytol from an algal oil.

A process for cracking phytol can also comprise hydrocracking phytol by contacting the phytol with a catalytic composition and a hydrogen source under hydrocracking conditions. For example, the catalytic composition can comprise an nickel ion exchange zeolite catalyst, such as Ni/LZY-72. Hydrocracking conditions can comprise temperatures of 100-1000 C. In a further embodiment, the temperatures are 200-500 C. In an example, phytol is flowed through a pulse reactor in 25ul pulses with hydrogen.

In an aspect, a composition is disclosed that comprises: a terpene and a catalytic cracking composition. The composition can be utilized to carry out a process or method described herein. For example, the composition can be the reactants for cracking the terpene into a composition or fuel product. The composition can be brought to catalytic cracking conditions, for example in a reactor, in order for the composition to react and break the terpene into light hydrocarbons.

In an embodiment, the terpene is selected from the group consisting of the following: a monoterpene, a sesquiterpene, a diterpene, a triterpene, a tetraterpene, cuparene, farnesene, squalene, zingerene, and carotene. The terpene can be any terpene that is suitable for catalytic cracking into smaller hydrocarbons, including those described herein.

In an aspect, a composition is disclosed that comprises: oil extracted from algae and a catalytic cracking composition. In other aspects, compositions are disclosed that comprise: ginger oil and a catalytic cracking composition, phytol and a catalytic cracking composition, or squalene and a catalytic cracking composition. Exemplary catalytic cracking compositions include those described herein without limitation. For example, the catalytic cracking composition can be a molecular sieve. In another example, the molecular sieve is a large pore molecular sieve having a pore size greater than 6 Angstrom. A large pore molecular sieve can have a cage diameter of 10-15 angstroms and/or be a 12-ring zeolite. Exemplary large pore molecular sieves include without limitation β, L, or Y-type zeolites, such as LZY-72, Valfor CP811BL-25, ELZ-L, or T-4546. In other instance the molecular sieve is a 10-ring zeolite, such as ZSM-5 zeolite.

Biomass Feedstocks

In certain embodiments, biomass feedstocks suitable for refining (for example, cracking) and methods of converting the same into light or rearranged hydrocarbons are described. Biomass feedstocks can comprises hydrocarbons extracted from genetically modified biological sources, such as algae and bacteria. Typically, cracking of oil produces light or rearranged hydrocarbons produced are suitable as fuels (for example, gasoline, diesel fuel or jet fuel), fuel additives and petrochemicals for further processing into plastics, resins, fibers, elastomers, lubricants, gels and the like.

More specifically, certain biomass hydrocarbons are selected as feedstock, which can undergo one or more refining processes including cracking and alteration. In certain embodiments, the biomass hydrocarbons are broken down or cracked into smaller molecules of hydrocarbons through scissions of carbon-carbon bonds. In other embodiments, the biomass hydrocarbons are altered (for example, by alkylation or isomerization) to form hydrocarbons having certain structures, such as branched hydrocarbons, hydrocarbons having high octane numbers (for example, higher than 90), and so forth. Advantageously, these biomass feedstocks can be compatible with existing petroleum refining processes and the light or rearranged hydrocarbons produced can be further processed or distributed using existing infrastructure for refining petroleum.

In some instances biomass feedstocks are blended or mixed with fossil fuel or petroleum based feedstocks before refining. For example, a feedstock extracted from algae can be blended with crude petroleum and then contacted with a catalytic composition to catalytically crack the mixture. Other methods of refining, such as fractionation, can be performed after a biomass feedstock is blended or mixed with a petroleum based feedstock. In some instances, the petroleum based feedstock has already been refined before blending with a biomass feedstock. For example, the petroleum based feedstock can be gasoline, diesel, or jet fuel. In other instances, the petroleum based feedstock is a mixture for fuel blending, for example, a hydrocarbon mixture that when blended with another hydrocarbon mixture can create a suitable fuel product. The mixture for fuel blending or the biomass feedstock or both can be suitable as a fuel product before refining. In another instance, the mixture for fuel blending or the biomass feedstock or neither is suitable as a fuel product before refining.

As used herein, "biomass hydrocarbons" or "biomass feedstocks" can refer to one or more organic compounds obtained from a biological organism that was alive within the last 50 years and comprise predominantly carbon and hydrogen, and may optionally comprise heteroatoms such as oxygen, nitrogen and sulfur. Unlike fossil-based crude oil, which originated from plant life up to 600 millions years ago, the hydrocarbons described herein are derived from living or recently living organisms. Such renewable biological sources include naturally occurring organisms as well as genetically modified organisms. In certain embodiments, such organisms comprise algae or bacteria. In some instances, the biomass hydrocarbon has between about 5-80 carbons, 10-50 carbons, 10-40 carbons, 10-60 carbons, 15-40 carbons, 15-60 carbons, 20-40 carbons and so forth. In other instances, the hydrocarbon has 5, 10, 15, 20, 25, 30, 35 or 40 carbons. The carbons of the hydrocarbon molecule are connected via covalent single, double or triple carbon-carbon bonds and are typically arranged in linear, branched, cyclic configurations or a combination thereof.

In some instances, biomass hydrocarbons take the form of terpenes, isoprenoids, lipids, alkyl esters, alkaloids, and phenyl propanoids. Terpene can refer to any terpenoid or isoprenoid that include heteroatoms as well as pure hydrocarbons. Biomass hydrocarbons described herein can be used as feedstocks in industrial refineries. Like the conventional feedstock, the biomass hydrocarbons can be cracked or altered. In some embodiments, the biomass hydrocarbons are broken down into light hydrocarbons which refers to hydrocarbons (as defined herein) having fewer carbons than the hydrocarbon feedstock. A light hydrocarbon can be, for example, a product of refined biomass feedstocks. Typically, a light hydrocarbon has fewer than 20 carbons, or fewer than 15 carbons, or fewer than 12 carbons, or fewer than 10 carbons, or fewer than 8 carbons. The light hydrocarbons can be cyclic or acyclic, saturated or unsaturated. Saturated acyclic hydrocarbons are also referred to as paraffin. Saturated cyclic hydrocarbons are also referred to as naphthenes. Unsaturated hydrocarbons are also referred to as olefins. Unsaturated hydrocarbons can also be aromatic. Exemplary light hydrocarbons include, without limitation, C2-C20 olefins, C6-C20 aromatic hydrocarbons (for example, benzene, toluene, xylenes, naphthalene and the like), C6-C20 naphthenes (for example, substituted or unsubstituted cyclopentanes and cyclohexanes), C1-C20 paraffins and the like. Depending on the distillation ranges, the light hydrocarbons may comprise fractions suitable as gasoline products, diesel, kerosene, or jet fuel.

Certain chemical structural characteristics can afford particular advantages in the cracking processes. For example, the biomass hydrocarbons may have specifically substituted and positioned carbon centers that can be converted into reactive intermediates under cracking conditions (for example, catalytic, steam, thermal or hydrocracking). These reactive intermediates facilitate further carbon-carbon bond scissions and produce light hydrocarbons. Branched hydrocarbons are particularly susceptible to carbon-carbon scission due to effects such as electrical stabilization and steric acceleration, both of which are associated with substituted carbon centers. See, for example, Ruchardt C. et al. *Angew. Chem. Ed. Engl.* 18, 429-440 (1980).

In other embodiments, the biomass feedstock comprises lower-order isoprenoids, which are terpenes having fewer than six isoprene residues. These lower-order isoprenoids are particularly useful for producing highly branched hydrocarbon structures which are suitable as high-octane fuels or fuel additives.

In particular, lower-order isoprenoids include monoterpenes (C10 terpenes having two isoprene residues), sesquiterpenes (C15 terpenes having three isoprene residues), diterpenes (C20 terpenes having four isoprene residues) and triterpenes (C30 terpenes having six isoprene residues). The isoprene residues are arranged in linear or cyclic configurations. Specific examples of the lower-order terpenes or isoprenoids include, but are not limited to, limonene, cuparene, myrcene, farnesene, geraniol, terpineol, farnesol, phytol, squalene and the like.

These lower-order isoprenoids comprise branched carbon centers (including both cyclic and acyclic carbons). They are therefore suitable precursors for producing hydrocarbons in the gasoline range fractions with high octane ratings and other desirable properties through cracking, isomerization, and/or other known processes typically employed in refinery operations.

As used herein, "octane rating" refers to knock resistance (anti-knock rating) of a spark ignition engine fuel as compared to a mixture of isooctane (2,2,4-trimethylpentane), a highly branched C8 hydrocarbon and n-heptane, a straight chain C7 hydrocarbon. More specifically, in internal combustion engines, a mixture of gasoline and air is compressed before ignition. The compressed mixture has a tendency to ignite prematurely rather than burning smoothly. Premature ignition (or self-ignition) creates a knock, characterized by a rattling or pinging sound in one or more cylinders. The knock results in a loss of peak power. Typically, highly branched hydrocarbons have better resistance to knock than linear hydrocarbons.

An octane number is therefore a quantitative measure of gasoline's resistance to knock. The octane number is determined by comparing the characteristics of a gasoline to isooctane (octane number 100, minimal knock) and heptane (octane number 0, considerable knock). A linear combination of these two components is typically used to measure the octane number of a particular gasoline. Thus, a gasoline with an octane number of 91 has the same knock as a mixture of 91% isooctane and 9% of heptane. As used herein, high octane rating refers to an octane number of 80 or higher, more typically, to an octane number of 90 or higher.

Base gasoline blend stocks or straight run gasoline typically have octane number between 60 and 70. Branched hydrocarbons, including substituted naphthenes (for example, methylcyclopentane, methylcyclohexane), and aromatics have higher than 90 (90+) octane numbers. Hydrocarbons having 90+ octane numbers can be used as additives to a fuel to boost its octane number. These additives are also referred to as "octane boosters". Typical octane boosters include, for example, aromatic hydrocarbons of high octane numbers, such as toluene (octane number 124), alcohols such as ethanol (octane number 115) and methanol (octane number 113), and organomatallics such as tetraethyl lead, and so forth.

Under suitable cracking conditions, the lower-order isoprenoids can be broken down to shorter (for example, fewer than C12) and branched hydrocarbons. The fractions suitable as high-octane fuels include, for example, branched C8 hydrocarbons, cyclic C5-C7 hydrocarbons, and aromatic hydrocarbons (for example, toluene and xylenes). The desired fractions can be isolated by distillation.

Apart from the isoprenoids, other classes of biomass hydrocarbons include lipids and nitrogen-containing hydrocarbons. Lipids generally refer to fatty acids, their derivatives and sterols. A free fatty acid typically comprises a long hydrocarbon chain terminated with a carboxylic acid. The hydrocarbon chain can be either saturated or unsaturated and typically ranges in length from 12 to 24 carbons (for example, C12-C24). A fatty acid derivative includes esters of a fatty acid. For example, glycerides (for example, vegetable oil) are lipids possessing a glycerol (propan-1,2,3-triol) core structure with one or more fatty acid groups. Additional fatty acid derivatives include alkyl esters, which are transesterification products of vegetable oils. Typically, methanol can be used to produce methyl esters of fatty acids. Alkaloids and phenyl propanoids are plant-derived nitrogen-containing hydrocarbons. They are typically amino acid derivatives and are constructed based on cellular metabolic pathways.

As discussed, the biomass hydrocarbons are derived from renewable biological sources, which include naturally occurring organisms and genetically modified organisms. Hydrocarbons are present in many naturally occurring organisms (eukaryotic or prokaryotic), which include plant matter, fungi, algae, bacteria, and the like. The biomass hydrocarbons described herein can be obtained from both living organisms and recently living organisms (biomass).

In particular, the polyenes described herein are present as organic pigments that are naturally occurring in plants and some other photosynthetic organisms like algae, some types of fungus and some bacteria. Carotenoids such as α-carotene, β-carotene (β,β-carotene), and lycopene (γ,γ-carotene) are known isoprenoids.

Algae represent a source for biomass particularly suitable for biological hydrocarbon production because algae rely on photosynthesis for energy production and can accumulate a high content of carotenes (for example, marine algae *Dunaliella salina*). Unlike crops, algae cultivation does not take up arable land and does not require an irrigation system. Moreover, algae are diverse microorganisms that can be genetically manipulated to increase the biosynthetic production of carotenes.

Carotenoids (for example, carotenes) can be produced from algae grown in harvesting ponds. Depending on the types of algae, the ponds may contain fresh or brine water. The algae are harvested and dried. Carotenoids can be extracted from the dried algae using an organic solvent. Typically, a low boiling-point solvent is used. The solvent can be recycled (for example, via distillation and condensation) when the carotene extract is concentrated. Exemplary solvents include, but are not limited to, hexane, carbon disulfide, petroleum ether, acetone and mixtures thereof.

In an aspect, a catalytic cracking process is provided for cracking oil from algae, the process comprising: extracting oil from algae to form a feedstock comprising a terpene; contacting under catalytic cracking conditions the feedstock containing the sesquiterpene with a catalytic composition. In an embodiment, the oil from algae comprises a terpene, for example, a naturally occurring terpene such as a carotenoid.

In another embodiment, the oil from algae comprises a sesquiterpene, such as cuparene or farnesene.

Algal oil can be provided to a process in a variety ways. For example, algae may be harvested and dried and then the oil extracted from lysed or destroyed cells. The cells can be chemically lysed or mechanical force can be used to destroy cell walls. Oil can be extracted from the algae using an organic solvent such as hexane. Other methods of extracting oil from algae can also be used with a process of the invention as would be obvious to one skilled in the art.

In an embodiment, the oil from algae comprises hydrocarbons and terpenes of longer chain length C10 and greater that naturally occur in algae. Different species of algae may generate oil with different hydrocarbon mixtures. In some embodiments, the oil from algae is a mixture of oils from more than one species of algae. In some embodiments, the oil from algae comprises an increased amount of terpenes. In some embodiments, the oil from algae comprises terpenes not naturally produced by the algae.

In some instances, a process herein also comprises mixing the oil from algae with a fuel component prior to contacting the feedstock. For example, a blend of algal oil and crude petroleum can be provided in a process as described herein and contacted with a catalytic composition. In another example, a blend of algal oil and a refined fuel such as gasoline can contacted with a catalytic composition. For example without limitation, the fuel component is selected from the group consisting of the following: fossil fuel, petroleum, a mixture for fuel blending, gasoline, diesel, jet fuel, and any combination thereof.

In an embodiment, a process comprises genetically modifying the algae prior to the extracting oil. For example, the chloroplast or nucleus of the algae may be transformed to generate enzymes that facilitate the production of terpenes. The terpenes can be naturally occurring in the algae or heterologous to the algae. In an embodiment, the algae are genetically modified to upregulate the production of a terpene that naturally occurs in the algae. In this manner, the oil from the algae comprises a greater amount of terpenes that are capable of being cracked under catalytic cracking conditions in a process such as a process described herein. In another embodiment, the algae are genetically modified to upregulate the production of a terpene that does not naturally occur in the algae. For example, a gene encoding an enzyme that generates a terpene through the MVA or MEP pathway can be inserted into the chloroplast or nucleus of the algae. The enzyme is configured to generate a terpene that does not naturally occur in the organism. In this way, the organism can be designed to comprise a measurable amount of a large hydrocarbon that may be useful in the production of a fuel product. For example, the algae can be genetically modified to produce increased amounts of a sesquiterpene as compared to not genetically modifying the algae. A genetic transformation encoding an enzyme that generates a sesquiterpene can be inserted into the algae. In an embodiment, the sesquiterpene is cuparene. In another embodiment, the sesquiterpene is farnesene. In yet another embodiment, the sesquiterpene is zingiberene. An algae can also be genetically modified to generate any size terpene, for example a monoterpene, a diterpene, a triterpene and the like. Examples of terpenes that can be generated from genetically modified algae include, but are not limited to, phytol and squalene.

In an aspect, a catalytic cracking process is disclosed herein for cracking oil from algae, the process comprising: extracting oil from algae to form a feedstock comprising a cuparene; and contacting under catalytic cracking conditions the feedstock containing the cuparene with a catalytic composition. In an embodiment, the process further comprises genetically modifying the algae prior to the extracting oil. For example, genetically modifying the algae can produce increased amounts of cuparene compared to not genetically modifying the algae.

Cracking of oil from algae can be performed using any of the catalytic compositions as described herein. In an embodiment, algal oil is cracked using a zeolite β catalyst. A reactor for cracking can be fed by a pump or a syringe pump in order to flow the oil through the catalytic composition. In an embodiment, the oil is injected into the reactor with a carrier gas, such as helium. The cracking products of the reaction can be identified by any suitable method as known in the art, including but not limited to gas or liquid chromatography and mass spectrometry.

In an embodiment, crude oil from algae can be refined before a cracking process is carried out. For example, the crude algal oil can be subjected to an RBD (refining bleaching deodorizing) process. In another example, the crude algal oil can be fractionated into desired components, such as by distillation. Fractionation can be predetermined by a user or can be set to fractionate the crude algal oil into hydrocarbon components of desired sizes, compositions, or shapes.

In an aspect, a composition is described comprising a triglyceride and less than 25% paraffins by weight, wherein the paraffins comprises C11-C13 paraffins. The algal enzyme or fragment thereof can be present in the composition in a trace amount or in a significant amount. The composition can be similar to a fuel product such as jet fuel, gasoline, or diesel. In an embodiment, the composition is derived from carrying out a process comprising cracking oil from algae. In an embodiment, the composition comprises less paraffins than fossil fuel based gasoline. The composition can also comprise paraffins of a larger size than are present in fossil fuel based gasoline, for example C11 to C13 paraffins.

In an embodiment, the composition is derived from carrying out a process comprising cracking oil from algae, wherein the composition comprises light alkanes. In an embodiment, the light alkanes comprise a gasoline fraction.

A composition described herein can be generated from a cracking process, wherein a biomass material comprising terpenes has been cracked. For example, the flow reactor as described above can be used to carry out a process to generate the composition. Triglycerides are present in photosynthetic organisms and include fatty acids.

The biomass feedstocks are suitable for refining on an industrial scale as well as laboratory scale. Conventionally, the refining processes convert crude oil containing a wide range of hydrocarbons, into fractions of useful substances, which are typically hydrocarbons characterized with specific length or structures. The fractions can be obtained by direct distillation or, more efficiently, by cracking longer hydrocarbons into shorter ones. In addition to physically transforming the crude oil, certain refining processes can also chemically transform cracked hydrocarbons to more desirable structures. For example, alkylation process can provide highly branched hydrocarbons suitable as high-octane fuels or fuel additives. See, for example, Petroleum Refilling Technology and Economics, Gary J. et al., Taylor & Francis Group (5$^{th}$ edition).

The biomass feedstocks can be refined in a similar manner as crude oil. Thus, certain embodiments describe a process of converting a biomass feedstock to one or more light hydrocarbons. Advantageously, depending on the desired specification of the light hydrocarbon fractions, biological hydrocarbons having specific structural characteristics can be selected and obtained from natural sources or from genetically modified organisms through rational design and manipulation of the biosynthetic pathway. For example, high octane gasoline products typically comprise about 3 to 12 carbons and are molecules which are more "compact" than linear paraffins afforded by structural proprieties such as carbon skeletal branching (for example, branched hydrocarbons), naphenic character (for example, cyclic non-aromatic structures) or aromatic characters. Based on these specifications, biological hydrocarbons having appropriate carbon skeletal properties (for example, carotenoids) can be selected to produce the desired fractions through, for example, catalytic cracking.

Generally speaking, the refining processes include cracking (for example, catalytic cracking, thermal cracking, steam cracking and hydrocracking) as well as isomerization, alteration or chemical conversion.

One embodiment provides a composition suitable for a catalytic cracking process, comprising a biomass feedstock and a cracking catalyst. In a particular embodiment, the biomass feedstock comprises at least one hydrocarbon having a polyene chain structure, the polyene chain structure comprising one or more quaternary olefinic carbons. In some instances, the biomass feedstock is exclusively of algal origin. In other instances, the biomass feedstock comprises triglycerides from algae.

Fluid catalytic cracking (FCC) is one of the most widely used refinery processes for converting heavy hydrocarbons into more valuable gasoline and lighter products. FIG. 1 shows schematically a standard FCC process suitable for cracking biomass feedstock. The feedstock is heated and sprayed into the base of a "riser" (a vertical or upward sloped pipe), where the pre-heated feedstock contacts fluidized zeolite catalyst at about 1230 to 1400° F. (665 to 760° C.). The hot catalyst vaporizes the feedstock and catalyzes the cracking reactions that break down the high molecular weight hydrocarbons into lighter components including LPG (liquid petroleum gas such as $C_3$-$C_4$ olefins), and acyclic or cyclic hydrocarbons ($C_5$-$C_{12}$). The catalyst-hydrocarbon mixture flows upward through the riser for just a few seconds and then the mixture is separated via cyclones. The catalyst-free hydrocarbons are routed to a fractioner for separating shorter hydrocarbon products (for example, $C_3$-$C_{12}$ hydrocarbons) from the heavier fuels. The shorter hydrocarbons, many of which are suitable as gasoline products, are more volatile than the heavier fuels. The heavier fuels include diesels and jet fuels that fractionally distill between 200° C. to 350° C. at atmospheric pressure.

During the trip up the riser, the cracking catalyst is "spent" by reactions which deposit coke on the catalyst and greatly reduce activity and selectivity. The process of coke formation is important to the overall process because it increases the H/C (hydrogen to carbon) ratio of the gaseous products to a range more suitable for gasoline. The "spent" catalyst is disengaged from the cracked hydrocarbon vapors and sent to a stripper (not shown) where it is contacted with steam to remove hydrocarbons remaining in the catalyst pores. The "spent" catalyst then flows into a fluidized-bed regenerator where air (or in some cases air plus oxygen) is used to burn off the coke to restore catalyst activity and also provide the necessary heat for the next reaction cycle. The "regenerated" catalyst then flows to the base of the riser, repeating the cycle.

A similar type of cracking process is also envisaged for the biologically derived feedstocks, though in certain embodiments, milder condition are employed with the primary purpose being to reduce the overall molecular weight without necessarily removing carbon or increasing the H/C ratio of the product. A process known as thermofor catalytic cracking may be used.

In one embodiment, the biomass feedstock comprises at least one hydrocarbon compound. In certain embodiments, carbenium ions are formed due to the action of the catalyst on the biologically derived feedstock, which is believed to induce carbon-carbon bond rupture in a β position of the carbenium ion (for example, β-scission). In other embodiments, an alkoxide type of intermediate can be formed at the quaternary olefinic carbon, which will also lead to β-scission.

A further embodiment provides a method for cracking hydrocarbons comprising contacting a biomass feedstock with a cracking catalyst under a catalytic cracking condition, the biomass feedstock including at least one hydrocarbon having a polyene structure, the polyene structure comprising one or more quaternary olefinic carbons.

Scheme VI shows the cracking of β-carotene (3, 7, 12, 16-tetramethyl-1,18-bis(2,6,6-trimethyl-1-cyclohexenyl)-octadeca-1,3,5,7,9,11,13,15,17-nonene) from a biological source. As shown, β-carotene is contacted with a zeolite catalyst (Z), whereby a quaternary olefinic carbon is converted to a carbenium ion. The carbenium intermediate undergoes C—C bond rupture at the β-position of the carbenium ion. A light olefin (1): 3-methyl-1-bis(2,6,6-trimethyl-1-cyclohexenyl)-1-butene is produced. Further cracking produces light olefin (2): 3,8-dimethyl-1,3,5,7,9-pentadecene, which may undergo a further cracking process. Other lighter terpenes, for example, monoterpenes such as myrcene (3), may also be produced upon cracking and possible rearrangement.

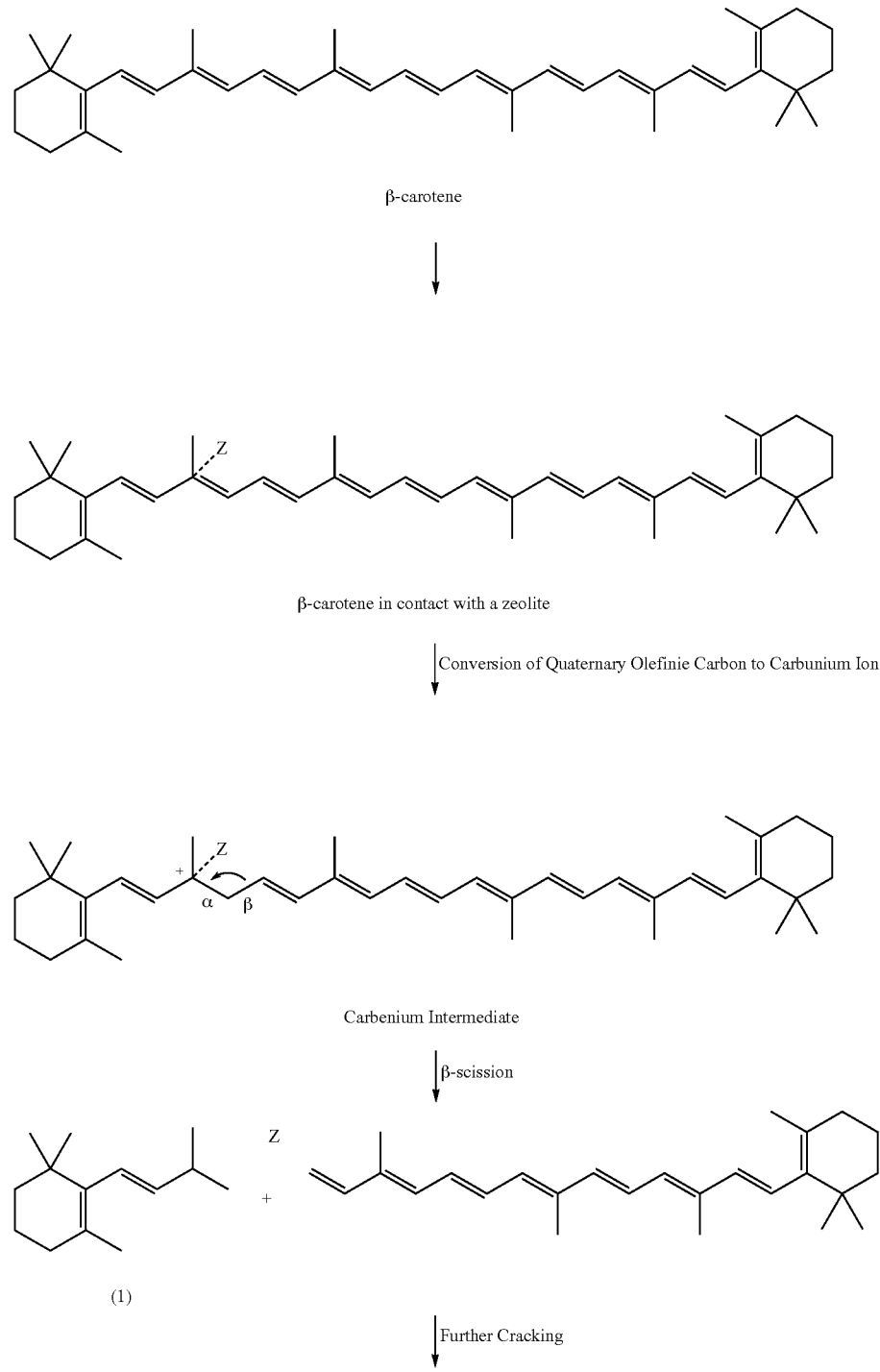

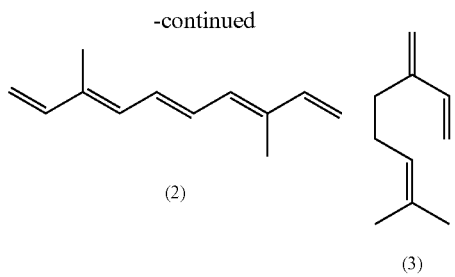

(2)

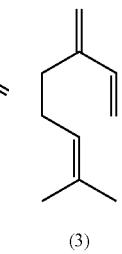

(3)

The light olefins produced can be used directly as fuel additives through blending or reforming. They can also be further processed to produce a number of gasoline products. The light olefins can also be used directly in petrochemical processes.

In another embodiment, the biomass feedstock comprises at least one lower-order isoprenoid, such as a monoterpene and a sesquiterpene.

In other embodiments, the biomass feedstocks are subjected to hydrocracking to produce light alkanes. The hydrocracking process produces saturated and shorter alkanes. Typically, the cracking process takes place in the presence of an elevated partial pressure of hydrogen gas. Hydrocracking is normally facilitated by a bifunctional catalyst that is capable of rearranging and breaking hydrocarbon chains as well as adding hydrogen to aromatics and olefins to produce naphthenes and alkanes.

In other embodiments, the biomass feedstocks are subjected to thermal cracking to produce light olefins. Thermal cracking takes place at elevated temperature (about 800° C.) and pressures (about 700 kPa). The thermal energy typically causes homolytic fission of carbon-carbon bonds and produces smaller olefins. Because homolytic fission generates radicals, many chemical reactions can take place during thermal cracking, including addition or elimination reactions.

In other embodiments, the biomass feedstocks are subjected to steam cracking to produce light olefins. Steam cracking can be carried out by diluting a biomass feedstock with steam and briefly heated in a furnace (at about 850° C.). The products produced in the reaction depend on the composition of the feed, the hydrocarbon to steam ratio and on the cracking temperature and furnace residence time. Typically, light olefins are produced.

The biomass hydrocarbons described herein can be cracked into lighter hydrocarbons in the presence of one or more zeolite catalysts. As shown in the Examples, the cracking processes typically result in temperature-dependent product distributions. Further, depending on the structure of the hydrocarbon being cracked, the product distribution can favor light hydrocarbons of high octane numbers. Additionally, the type of catalyst plays an important role in determining the nature and distribution of the cracked products.

As described, lower order terpenes (for example, cuparene, farnesene, ginger oil, phytol, and squalene) can be subjected to catalytic cracking conditions. The cracking products typically include paraffins (for example, C4-C9), naphthenes (for example, C5-C9), aromatics (for example, benzene, toluene, xylene, naphthalene). Among the cracking products, hydrocarbons with branched carbon centers such as branched paraffins, naphthenes and aromatics tend to be associated with high octane numbers (for example, higher than 91).

In certain embodiments, cracking products having high octane numbers are produced at over 60% yield at temperatures ranging from 200° C. to 500° C. Depending on the desirable products, an optimal temperature range can be empirically established at which, products of high octane numbers (for example, aromatics other than benzene, naphthenes) are maximized and products of low octane numbers (for example, linear paraffins) are minimized. Typically, the temperatures may range from 200° C. to 350° C., or 350° C. to 450° C.

The cracking products are thus produced in high yield and are of desirable and/or diverse structural characteristics, which allow for them to be used as fuel, fuel additives or for use directly as petrochemicals. Accordingly, the biomass hydrocarbons described herein are suitable for refining into useful substances, and can be used to replace or supplement fossil fuel in refining processes.

In an aspect, a method for making a fuel product is disclosed herein that comprises: obtaining a feedstock from a genetically modified non-vascular photosynthetic organism; and contacting under catalytic cracking conditions the feedstock with a catalytic composition thereby making a fuel product, wherein the catalytic composition comprises a large pore molecular sieve having a pore size greater than 6 Angstrom. For example, the feedstock can be a genetically-modified algae. The algae can be genetically-modified in a variety of ways including those that upregulate the production of a terpene. In an embodiment, genetic modification allows the organism to generate a hydrocarbon or terpene that does not naturally occur in the organism. Catalytic cracking conditions can be conditions as described herein. For example, the cracking can occur at a temperature up to 420° C. The catalytic composition in contact with the genetically modified non-vascular photosynthetic organisms can also be any catalytic composition as described herein or a composition that would be obvious or anticipated for use under catalytic cracking conditions as would be known to one skilled in the art. In some instances, a large pore molecular sieve is a 12 ring zeolite.

A fuel product produced from a method or process as described herein can have an octane number between about 85 and 125. A fuel product can also an octane number of greater than 90.

In some instances, a process or method can further comprises adding a fuel component to the fuel product, wherein the fuel component is a blending fuel, such as ethanol, jet fuel, diesel, biodiesel, or gasoline. For example, the fuel product can be about 5-95% of a mixture comprising the fuel product and the fuel component. In another embodiment, a fuel additive, such as MTBE, detergents, and oxidizers can be added to the fuel product.

Compositions and Products

Provided herein are compositions and methods for creating products from terpenes and creating product from terpenes from biomass. Examples of products include, but are not limited to, fuel products, fragrance products, and insecticide products. A product can be any substance that releases molecularly stored energy. In an embodiment, a product is organic molecules. In another embodiment, a product is a hydrocarbon. In some instances a product does not include hydrogen. In some instances a product does not include oxygen. In some instances, a product does not include antibodies or proteins. In some instances a product does not include fatty acids.

Examples of fuel products include petrochemical products and their precursors and all other substances that may be useful in the petrochemical industry. Fuel products include, for example, petroleum products, and precursors of petroleum, as well as petrochemicals and precursors thereof. The fuel product may be used for generating substances, or materials, useful in the petrochemical industry, including petroleum products and petrochemicals. The fuel or fuel products may be used in a combustor such as a boiler, kiln, dryer or furnace. Other examples of combustors are internal combustion engines such as vehicle engines or generators, including gasoline engines, diesel engines, jet engines, and others. Fuel products may also be used to produce plastics, resins, fibers, elastomers, lubricants, and gels.

Examples of products contemplated herein include hydrocarbon products and hydrocarbon derivative products that can consist of hydrogen molecules and carbon molecules and sometimes one or more heteroatoms, wherein the heteroatom is any atom that is not hydrogen or carbon. Examples of heteroatoms include, but are not limited to, nitrogen, oxygen, sulfur, and phosphorus. Some products are hydrocarbon-rich, wherein at least 50%, 60%, 70%, 80%, 90%, 95, 99% of the product by weight is made up carbon and hydrogen. In an embodiment, a product is 100% by weight carbon and hydrogen atoms.

Fuel products, such as hydrocarbons, may be precursors or products conventionally derived from crude oil, or petroleum, such as, but not limited to, liquid petroleum gas, naptha (ligroin), gasoline, kerosene, diesel, lubricating oil, heavy gas, coke, asphalt, tar, and waxes. For example, fuel products may include small alkanes (for example, 1 to approximately 4 carbons) such as methane, ethane, propane, or butane, which may be used for heating (such as in cooking) or making plastics. Fuel products may also include molecules with a carbon backbone of approximately 5 to approximately 9 carbon atoms, such as naptha or ligroin, or their precursors. Other fuel products may be about 5 to about 12 carbon atoms or cycloalkanes used as gasoline or motor fuel. Molecules and aromatics of approximately 10 to approximately 18 carbons, such as kerosene, or its precursors, may also be fuel products. Fuel products may also include molecules, or their precursors, with more than 12 carbons, such as used for lubricating oil. Other fuel products include heavy gas or fuel oil, or their precursors, typically containing alkanes, cycloalkanes, and aromatics of approximately 20 to approximately 70 carbons. Fuel products also includes other residuals from crude oil, such as coke, asphalt, tar, and waxes, generally containing multiple rings with about 70 or more carbons, and their precursors.

The various fuel products may be further refined to a final product for an end user by a number of processes. Refining can occur by fractional distillation. For example, a mixture of fuel products, such as a mix of different hydrocarbons with different various chain lengths may be separated into various components by fractional distillation.

The fuel products may also be refined by combining them in a unification step, for example by using catalysts, such as platinum or a platinum-rhenium mix. The unification process typically produces hydrogen gas, a by-product which may be used in cracking.

The fuel products may also be refined by altering or rearranging or restructuring hydrocarbons into smaller molecules. There are a number of chemical reactions that occur in the catalytic reforming process of which are known to one of ordinary skill in the arts. Generally, catalytic reforming is performed in the presence of a catalyst and high partial pressure of hydrogen. One common process is alkylation. For example, propylene and butylene are mixed with a catalyst such as hydrofluoric acid or sulfuric acid.

The fuel products may also be blended or combined into mixtures to obtain an end product. For example, the fuel products may be blended to form gasoline of various grades, gasoline with or without additives, lubricating oils of various weights and grades, kerosene of various grades, jet fuel, diesel fuel, heating oil, and chemicals for making plastics and other polymers. Compositions of the fuel products described herein may be combined or blended with fuel products produced by other means.

The products produced may be naturally, or non-naturally (as a result of the transformation) produced by the host cell and organism(s) transformed. The product may also be a novel molecule not present in nature. For example, products naturally produced in algae may be terpenes such as carotenoids (for example beta-carotene). Examples of products not naturally produced by algae may include a non-native terpene such as limonene.

In some instances, a product (such as a fuel product) contemplated herein comprises one or more carbons derived from an inorganic carbon source. In an embodiment, at least 10%, 20%, 30%, 40%, 50%, 60%, 70%, 80%, 90%, 95%, or 99% of the carbons of a product as described herein are derived from an inorganic carbon source. Examples of inorganic carbon sources include, but are not limited to, carbon dioxide, carbonate, bicarbonate, and carbonic acid. The product can be an organic molecule with carbons from an inorganic carbon source that were fixed during photosynthesis.

A product herein can be described by its Carbon Isotope Distribution (CID). At the molecular level, CID is the statistical likelihood of a single carbon atom within a molecule to be one of the naturally occurring carbon isotopes (for example, $^{12}C$, $^{13}C$, or $^{14}C$). At the bulk level of a product, CID may be the relative abundance of naturally occurring carbon isotopes (for example, $^{12}C$, $^{13}C$, or $^{14}C$) in a compound containing at least one carbon atom. While it is noted that CID of each fossil fuel may differ based on its source, CID(fos) (for example, CID of carbon in a fossil fuel, for example, petroleum, natural gas, and coal) is distinguishable from CID(atm) (for example, the CID of carbon in current atmospheric carbon dioxide). Additionally, CID(photo-atm) refers to the CID of a carbon-based compound made by photosynthesis in recent history where the source of inorganic carbon was carbon dioxide in the atmosphere. CID(photo-fos) refers to the CID of a carbon based compound made by photosynthesis in recent history where the source of substantially all of the inorganic carbon was carbon dioxide produced by the burning of fossil fuels (for example, coal, natural gas, and/or petroleum).

The exact distribution is also a characteristic of 1) the type of photosynthetic organism that produced the molecule and 2) the source of inorganic carbon. These isotope distributions can be used to define the composition of photosynthetically-derived fuel products.

Carbon isotopes are unevenly distributed among and within different compounds and the isotopic distribution can reveal information about the physical, chemical, and metabolic processes involved in carbon transformations. The overall abundance of $^{13}C$ relative to $^{12}C$ in photosynthetic organism tissue is commonly less than in the carbon of atmospheric carbon dioxide, indicating that carbon isotope discrimination occurs in the incorporation of carbon dioxide into photosynthetic biomass.

Some fuel products can be produced from biomass, sometimes after refining, will be identical to existing petrochemicals, for example same structure. Some of the fuel products may not be the same as existing petrochemicals. In an embodiment, a fuel product or composition is identical to an existing petrochemical, except for the carbon isotope distribution. For example, it is believed no fossil fuel petrochemicals have a $\delta^{13}C$ distribution of less than −32‰, whereas fuel products as described herein can have a $\delta^{13}C$ distribution of less than −32‰, −35‰, −40‰, −45‰, −50‰, −55‰, or −60‰. In another embodiment, a fuel product or composition is similar but not the same as an existing fossil fuel petrochemical and has a $\delta^{13}C$ distribution of less than −32‰, −35‰, −40‰, −45‰, −50‰, −55‰, or −60‰. However, although a molecule may not exist in conventional petrochemicals or refining, it may still be useful in these industries. For example, a hydrocarbon can be produced that is in the boiling point range of gasoline, and that could be used as gasoline or an additive, even though the hydrocarbon does not normally occur in gasoline. A fuel product can be a composition comprising: hydrogen and carbon molecules, wherein the hydrogen and carbon molecules are at least 80% of the atomic weight of the composition, and wherein the $\delta^{13}C$ distribution of the composition is less than −32‰. For some fuel products described herein, the hydrogen and carbon molecules are at least 90% of the atomic weight of the composition. For example, a biodiesel or fatty acid methyl ester (which have less than 90% hydrogen and carbon molecules by weight) may not be part of the composition. In still other compositions, the hydrogen and carbon molecules are at least 95 or 99% of the atomic weight of the composition. In yet other compositions, the hydrogen and carbon molecules are 100% of the atomic weight of the composition. In some instances, the composition is a liquid. In other instances, the composition is a fuel additive or a fuel product.

Also described herein is a fuel product comprising a composition comprising hydrogen and carbon molecules, wherein the hydrogen and carbon molecules are at least 80% of the atomic weight of the composition, and wherein the $\delta^{13}C$ distribution of the composition is less than −32‰ and a fuel component. In some embodiments, the $\delta^{13}C$ distribution of the composition is less than about −35‰, −40‰, −45‰, −50‰, −55‰, or −60‰. In some instances, the fuel component is a blending fuel which may be fossil fuel, gasoline, diesel, ethanol, jet fuel, or any combination thereof. In still other instances, the blending fuel has a $\delta^{13}C$ distribution of greater than −32‰. For some fuel products described herein, the fuel component is a fuel additive which may be MTBE, an anti-oxidant, an antistatic agent, a corrosion inhibitor, and any combination thereof. A fuel product as described herein may be a product generated by blending a fuel product as described and a fuel component. In some instances, the fuel product has a $\delta^{13}C$ distribution of greater than −32‰. In other instances, the fuel product has a $\delta^{13}C$ distribution of less than −32‰. For example, a composition extracted from an organism can be blended with a fuel component prior to refining (for example, cracking) in order to generate a fuel product as described herein. A fuel component, as described, can be a fossil fuel, or a mixing blend for generating a fuel product. For example, a mixture for fuel blending may be a hydrocarbon mixture that is suitable for blending with another hydrocarbon mixture to generate a fuel product. For example, a mixture of light alkanes may not have a certain octane number to be suitable for a type of fuel, however, it can be blended with a high octane mixture to generate a fuel product. In an example, a composition with a $\delta^{13}C$ distribution of less than −32‰ is blended with a hydrocarbon mixture for fuel blending to create a fuel product. In some instances, the composition or fuel component alone are not suitable as a fuel product, however, when combined, they comprise a fuel product. In other instances, either the composition or the fuel component or both individual are suitable as a fuel product. In yet other instances, the fuel component is an existing petroleum product, such as gasoline or jet fuel. In yet other instances, the fuel component is derived from a renewable resource, such as bioethanol, biodiesel, biogasoline, and the like.

The biomass feedstocks are suitable for producing high-octane hydrocarbon products. Thus, one embodiment describes a method of forming a fuel product comprising: forming one or more light hydrocarbons having 4 to 12 carbons having an Octane number of 80 or higher by cracking a biomass feedstock, and blending the one or more light hydrocarbons with the Octane number of 80 or higher with a hydrocarbon having an Octane number of 80 or less. Typically, the hydrocarbons having an Octane number of 80 or less are fossil fuels derived from refining crude oil. In a particular embodiment, the biomass feedstock includes at least one hydrocarbon having a polyene structure, the polyene structure comprising one or more quaternary olefinic carbons. In another embodiment, the biomass feedstock includes at least one lower-order isoprenoid, as defined herein.

The biomass feedstock can be modified or tagged to afford verifiable characteristics that are preserved in the cracked or altered light hydrocarbon products, such that the light hydrocarbon products can be identified or traced back as to its original feedstock. For example, carbon isotopes can be introduced into a biomass hydrocarbon in the course of its biosynthesis. The carbon isotopes serve as markers in the hydrocarbon feedstocks produced. The tagged hydrocarbon feedstocks can be subjected to the refining processes described herein to produce light hydrocarbon products tagged with carbon isotopes. The isotopes allows for the identification of the tagged products, either alone or in combination with other untagged products, such that the tagged products can be traced back to their biomass feedstocks.

Biomass Hydrocarbon Production

Any of the products described herein can be prepared by transforming an organism to cause the production by such organism of the product. The organism can be photosynthetic prior to or after transformation.

Organisms

Examples of organisms that can be transformed using the compositions and methods herein include vascular and non-vascular organisms. The organism can be prokaroytic or eukaroytic. The organism can be unicellular or multicellular.

Examples of non-vascular photosynthetic organisms include bryophtyes, such as marchantiophytes or anthocerotophytes. In some instances the organism is a cyanobacteria. In some instances, the organism is algae (for example, macroalgae or microalgae). The algae can be unicellular or multicellular algae. In some instances the organism is a rhodophyte, chlorophyte, heterokontophyte, tribophyte, glaucophyte, chlorarachniophyte, euglenoid, haptophyte, cryptomonad, dinofiagellum, or phytoplankton.

For example, the microalgae *Chlamydomonas reinhardtii* may be transformed with a vector encoding limonene synthase to produce limonene. In another embodiment, the microalgae may be transformed with one or more vectors encoding a limonene synthase and proteins to improve limonene production.

The methods can be exemplified using the microalga, *C. reinhardtii*. The use of microalgae to express a polypeptide or protein complex according to a method of the invention and provides the advantage that large populations of the microalgae can be grown, including commercially (Cyanotech Corp.; Kailua-Kona Hi.), thus allowing for production and, if desired, isolation of large amounts of a desired product. However, the ability to express, for example, functional mammalian polypeptides, including protein complexes, in the chloroplasts of any plant allows for production of crops of such plants and, therefore, the ability to conveniently produce large amounts of the polypeptides. Accordingly, the methods can be practiced using any plant having chloroplasts, including, for example, macroalgae, for example, marine algae and seaweeds, as well as plants that grow in soil.

The term "plant" is used broadly herein to refer to a eukaryotic organism containing plastids, particularly chloroplasts, and includes any such organism at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or a cultured cell, or can be part of higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like.

A method as described herein can generate a plant containing chloroplasts that are genetically modified to contain a stably integrated polynucleotide (Hager and Bock, *Appl. Microbiol. Biotechnol.* 54:302-310, 2000). Accordingly, a method can further provide a transgenic (transplastomic) plant, for example *C. reinhardtii*, which comprises one or more chloroplasts containing a polynucleotide encoding one or more heterologous polypeptides, including polypeptides that can specifically associate to form a functional protein complex. A photosynthetic organism as described herein can comprise at least one host cell that is modified to generate a product.

Expression Vectors and Host Cell Transformation

The organisms/host cells herein can be transformed to modify the production of a product(s) with an expression vector, for example, to increase production of a product(s). The product(s) can be naturally or not naturally produced by the organism.

The expression vector can encode one or more homologous or heterologous nucleotide sequences (derived from the host organism or from a different organism) and/or one or more autologous nucleotide sequences (derived from the same organism) and/or those that encode homologous or heterologous polypeptides. Examples of heterologous nucleotide sequences that can be transformed into an algal host cell include genes from bacteria, fungi, plants, photosynthetic bacteria or other algae. Examples of autologous nucleotide sequences that can be transformed into an algal host cell include isoprenoid synthetic genes, endogenous promoters and 5' UTRs from the psbA, atpA, or rbcL genes. In some instances, a heterolgous sequence is flanked by two autologous sequences or homologous sequences. Homologous sequences are those that have at least 50%, 60%, 70%, 80%, or 90% homology to the sequence in the host cell. In some instances, a homologous sequence is flanked by two autologous sequences. The first and second homologous sequences enable recombination of the heterologous sequence into the genome of the host organism. The first and second homologous sequences can be at least 100, 200, 300, 400, or 500 nucleotides in length.

The expression vector may comprise nucleotide sequences that are codon biased for expression in the organism being transformed. The skilled artisan will be aware of the "codon-bias" exhibited by a specific host cell in usage of nucleotide codons to specify a given amino acid. Without being bound by theory, by using a host cell's preferred codons, the rate of translation may be greater. Therefore, when synthesizing a gene for improved expression in a host cell, it may be desirable to design the gene such that its frequency of codon usage approaches the frequency of preferred codon usage of the host cell. The codons can be generally A/T rich, for example, A/T rich in the third nucleotide position of the codons. Typically, the A/T rich codon bias is used for algae. In some embodiments, at least 50% of the third nucleotide position of the codons are A or T. In other embodiments, at least 60%, 70%, 80%, 90%, or 99% of the third nucleotide position of the codons are A or T.

One approach to construction of a genetically manipulated strain of alga involves transformation with a nucleic acid which encodes a gene of interest, typically an enzyme capable of converting a precursor into a fuel product or precursor of a fuel product. In some embodiments, a transformation may introduce nucleic acids into any plastid of the host alga cell (for example, chloroplast). Transformed cells are typically plated on selective media following introduction of exogenous nucleic acids. This method may also comprise several steps for screening. Initially, a screen of primary transformants is typically conducted to determine which clones have proper insertion of the exogenous nucleic acids. Clones which show the proper integration may be patched and re-screened to ensure genetic stability. Such methodology ensures that the transformants contain the genes of interest. In many instances, such screening is performed by polymerase chain reaction (PCR); however, any other appropriate technique known in the art may be utilized. Many different methods of PCR are known in the art (for example, nested PCR, real time PCR). Particular examples are utilized in the examples described herein; however, one of skill in the art will recognize that other PCR techniques may be substituted for the particular protocols described. Following screening for clones with proper integration of exogenous nucleic acids, typically clones are screened for the presence of the encoded protein. Protein expression screening typically is performed by Western blot analysis and/or enzyme activity assays.

A recombinant nucleic acid molecule useful in a method of the invention can be contained in a vector. Furthermore, where the method is performed using a second (or more) recombinant nucleic acid molecules, the second recombinant nucleic acid molecule also can be contained in a vector, which can, but need not, be the same vector as that containing the first recombinant nucleic acid molecule. The vector can be any vector useful for introducing a polynucleotide into a chloroplast and, preferably, includes a nucleotide sequence of chloroplast genomic DNA that is sufficient to undergo homologous recombination with chloroplast genomic DNA, for example, a nucleotide sequence comprising about 400 to 1500 or more substantially contiguous nucleotides of chloroplast genomic DNA. Chloroplast vectors and methods for selecting regions of a chloroplast genome for use as a vector are well known (see, for example, Bock, J. Mol. Biol. 312: 425-438, 2001; see, also, Staub and Maliga, *Plant Cell* 4:39-45, 1992; Kavanagh et al., *Genetics* 152:1111-1122, 1999, each of which is incorporated herein by reference).

In some instances, such vectors include promoters. Promoters may come from any source (for example, viral, bacterial, fungal, protist, animal). The promoters contemplated herein can be specific to photosynthetic organisms, non-vascular photosynthetic organisms, and vascular photosynthetic organisms (for example, algae, flowering plants). As used herein, the term "non-vascular photosynthetic organism," refers to any macroscopic or microscopic organism, including, but not limited to, algae, cyanobacteria and photosynthetic bacteria, which does not have a vascular system such as that found in higher plants. In some instances, the nucleic acids above are inserted into a vector that comprises a promoter of a photosynthetic organism, for example, algae. The promoter can be a promoter for expression in a chloroplast and/or other plastid. In some instances, the nucleic acids are chloroplast based. Examples of promoters contemplated for insertion of any of the nucleic acids herein into the chloroplast include those disclosed in US Application No. 2004/0014174. The promoter can be a constitutive promoter or an inducible promoter. A promoter typically includes necessary nucleic acid sequences near the start site of transcription, (for example, a TATA element).

The entire chloroplast genome of *C. reinhardtii* is available to the public on the world wide web, at the URL "biology.duke.edu/chlamy_genome/-chloro.html" (see "view complete genome as text file" link and "maps of the chloroplast genome" link), each of which is incorporated herein by reference (J. Maul, J. W. Lilly, and D. B. Stern, unpublished results; revised Jan. 28, 2002; to be published as GenBank Acc. No. AF396929). Generally, the nucleotide sequence of the chloroplast genomic DNA is selected such that it is not a portion of a gene, including a regulatory sequence or coding sequence, particularly a gene that, if disrupted due to the homologous recombination event, would produce a deleterious effect with respect to the chloroplast, for example, for replication of the chloroplast genome, or to a plant cell containing the chloroplast. In this respect, the website containing the *C. reinhardtii* chloroplast genome sequence also provides maps showing coding and non-coding regions of the chloroplast genome, thus facilitating selection of a sequence useful for constructing a vector. For example, the chloroplast vector, p322, is a clone extending from the Eco (Eco RI) site at about position 143.1 kb to the Xho (Xho I) site at about position 148.5 kb (see, world wide web, at the URL "biology.duke.edu/chlamy_genome/chloro.html", and clicking on "maps of the chloroplast genome" link, and "140-150 kb" link; also accessible directly on world wide web at URL "biology.duke.edu/chlam-y/chloro/chloro140.html").

A vector utilized in the practice of a method or process herein also can contain one or more additional nucleotide sequences that confer desirable characteristics on the vector, including, for example, sequences such as cloning sites that facilitate manipulation of the vector, regulatory elements that direct replication of the vector or transcription of nucleotide sequences contain therein, sequences that encode a selectable marker, and the like. As such, the vector can contain, for example, one or more cloning sites such as a multiple cloning site, which can, but need not, be positioned such that a heterologous polynucleotide can be inserted into the vector and operatively linked to a desired element. The vector also can contain a prokaryote origin of replication (ori), for example, an *E. coli* ori or a cosmid ori, thus allowing passage of the vector in a prokaryote host cell, as well as in a plant chloroplast, as desired.

A regulatory element, as the term is used herein, broadly refers to a nucleotide sequence that regulates the transcription or translation of a polynucleotide or the localization of a polypeptide to which it is operatively linked. Examples include, but are not limited to, an RBS, a promoter, enhancer, transcription terminator, an initiation (start) codon, a splicing signal for intron excision and maintenance of a correct reading frame, a STOP codon, an amber or ochre codon, an IBES. Additionally, a cell compartmentalization signal (for example, a sequence that targets a polypeptide to the cytosol, nucleus, chloroplast membrane or cell membrane). Such signals are well known in the art and have been widely reported (see, for example, U.S. Pat. No. 5,776,689).

Any of the expression vectors herein can further comprise a regulatory control sequence. A regulatory control sequence may include for example, promoter(s), operator(s), repressor(s), enhancer(s), transcription termination sequence(s), sequence(s) that regulate translation, or other regulatory control sequence(s) that are compatible with the host cell and control the expression of the nucleic acid molecules. In some cases, a regulatory control sequence includes transcription control sequence(s) that are able to control, modulate, or effect the initiation, elongation, and/or termination of transcription. For example, a regulatory control sequence can increase transcription and translation rate and/or efficiency of a gene or gene product in an organism, wherein expression of the gene or gene product is upregulated resulting (directly or indirectly) in the increased production of a product described herein. The regulatory control sequence may also result in the increase of production of a product by increasing the stability of a gene or gene product.

A regulatory control sequence can be autologous or heterologous, and if heterologous, may be homologous. The regulatory control sequence may encode one or more polypeptides which are enzymes that promote expression and production of products. For example, a heterologous regulatory control sequence may be derived from another species of the same genus of the organism (for example, another algal species) and encode a synthase in an algae. In another example, an autologous regulatory control sequence can be derived from an organism in which an expression vector is to be expressed.

Depending on the application, regulatory control sequences can be used that effect inducible or constitutive expression. The algal regulatory control sequences can be used, and can be of nuclear, viral, extrachromosomal, mitochondrial, or chloroplastic origin.

Suitable regulatory control sequences include those naturally associated with the nucleotide sequence to be expressed (for example, an algal promoter operably linked with an algal-derived nucleotide sequence in nature). Suitable regulatory control sequences include regulatory control sequences not naturally associated with the nucleic acid molecule to be expressed (for example, an algal promoter of one species operatively linked to an nucleotide sequence of another organism or algal species). The latter regulatory control sequences can be a sequence that controls expression of another gene within the same species (for example, autologous) or can be derived from a different organism or species (for example, heterologous).

To determine whether a putative regulatory control sequence is suitable, the putative regulatory control sequence is linked to a nucleic acid molecule typically encodes a protein that produces an easily detectable signal. The construction may then be introduced into an alga or other organism by standard techniques and expression thereof is monitored. For example, if the nucleic acid molecule encodes a dominant selectable marker, the alga or organism to be used is tested for the ability to grow in the presence of a compound for which the marker provides resistance.

In some cases, a regulatory control sequence is a promoter, such as a promoter adapted for expression of a nucleotide sequence in a non-vascular, photosynthetic organism. For example, the promoter may be an algal promoter, for example as described in U.S. Publ. Appl. Nos. 2006/0234368 and 2004/0014174, and in Hallmann, *Transgenic Plant* J. 1:81-98 (2007). The promoter may be a chloroplast specific promoter or a nuclear promoter. The promoter may an EF1-α gene promoter or a D promoter. In some embodiments, the synthase is operably linked to the EF1-α gene promoter. In other embodiments, the synthase is operably linked to the D promoter.

A regulatory control sequences herein can be found in a variety of locations, including for example, coding and non-coding regions, 5' untranslated regions (for example, regions upstream from the coding region), and 3' untranslated regions (for example, regions downstream from the coding region).

Thus, in some instances an autologous or heterologous nucleotide sequence can include one or more 3' or 5' untranslated regions, one or more introns, or one or more exons.

For example, in some embodiments, a regulatory control sequence can comprise a Cyclotella cryptica acetyl-CoA carboxylase 5' untranslated regulatory control sequence or a Cyclotella cryptica acetyl-CoA carboxylase 3'-untranslated regulatory control sequence (U.S. Pat. No. 5,661,017).

A regulatory control sequence may also encode chimeric or fusion polypeptides, such as protein AB, or SAA, that promotes expression of heterologous nucleotide sequences and proteins. Other regulatory control sequences include autologous intron sequences that may promote translation of a heterologous sequence.

The regulatory control sequences used in any of the expression vectors herein may be inducible, Inducible regulatory control sequences, such as promoters, can be inducible by light, for example. Regulatory control sequences may also be autoregulatable. Examples of autoregulatable regulatory control sequences include those that are autoregulated by, for example, endogenous ATP levels or by the product produced by the organism. In some instances, the regulatory control sequences may be inducible by an exogenous agent. Other inducible elements are well known in the art and may be adapted for use herein.

Various combinations of the regulatory control sequences described herein may be embodied and combined with other features described herein. In some cases, an expression vector comprises one or more regulatory control sequences operatively linked to a nucleotide sequence encoding a polypeptide that effects, for example, upregulates production of a product described herein. In some cases, an expression vector comprises one or more regulatory control sequences operatively linked to a nucleotide sequence encoding a polypeptide that effects, for example, upregulates production of a product.

A vector or other recombinant nucleic acid molecule may include a nucleotide sequence encoding a reporter polypeptide or other selectable marker. The term "reporter" or "selectable marker" refers to a polynucleotide (or encoded polypeptide) that confers a detectable phenotype. A reporter generally encodes a detectable polypeptide, for example, a green fluorescent protein or an enzyme such as luciferase, which, when contacted with an appropriate agent (a particular wavelength of light or luciferin, respectively) generates a signal that can be detected by eye or using appropriate instrumentation (Giacomin, *Plant Sci.* 116:59-72, 1996; Scikantha, *J. Bacteriol.* 178:121, 1996; Gerdes, *FEBS Lett.* 389:44-47, 1996; see, also, Jefferson, *EMBO J.* 6:3901-3907, 1997, fl-glucuronidase). A selectable marker generally is a molecule that, when present or expressed in a cell, provides a selective advantage (or disadvantage) to the cell containing the marker, for example, the ability to grow in the presence of an agent that otherwise would kill the cell.

A selectable marker can provide a means to obtain prokaryotic cells or plant cells or both that express the marker and, therefore, can be useful as a component of a vector (see, for example, Bock, supra, 2001). Examples of selectable markers include, but are not limited to, those that confer antimetabolite resistance, for example, dihydrofolate reductase, which confers resistance to methotrexate (Reiss, *Plant Physiol. (Life Sci. Adv.)* 13:143-149, 1994); neomycin phosphotransferase, which confers resistance to the aminoglycosides neomycin, kanamycin and paromycin (Herrera-Estrella, *EMBO J.* 2:987-995, 1983), hygro, which confers resistance to hygromycin (Marsh, *Gene* 32:481-485, 1984), trpB, which allows cells to utilize indole in place of tryptophan; hisD, which allows cells to utilize histinol in place of histidine (Hartman, *Proc. Natl. Acad. Sci., USA* 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: Current Communications in Molecular Biology, Cold Spring Harbor Laboratory ed.); and deaminase from *Aspergillus terreus*, which confers resistance to Blasticidin S (Tamura, *Biosci. Biotechnol. Biochem.* 59:2336-2338, 1995). Additional selectable markers include those that confer herbicide resistance, for example, phosphinothricin acetyltransferase gene, which confers resistance to phosphinothricin (White et al., *Nucl. Acids Res.* 18:1062, 1990; Spencer et al., *Theor Appl. Genet.* 79:625-631, 1990), a mutant EPSPV-synthase, which confers glyphosate resistance (Hinchee et al., *BioTechnology* 91:915-922, 1998), a mutant acetolactate synthase, which confers imidazolione or sulfonylurea resistance (Lee et al., *EMBO J.* 7:1241-1248, 1988), a mutant psbA, which confers resistance to atrazine (Smeda et al., *Plant Physiol.* 103:911-917, 1993), or a mutant protoporphyrinogen oxidase (see U.S. Pat. No. 5,767,373), or other markers conferring resistance to an herbicide such as glufosinate. Selectable markers include polynucleotides that confer dihydrofolate reductase (DHFR) or neomycin resistance for eukaryotic cells and tetracycline; ampicillin resistance for prokaryotes such as *E. coli*; and bleomycin, gentamycin, glyphosate, hygromycin, kanamycin, methotrexate, phleomycin, phosphinotricin, spectinomycin, streptomycin, sulfonamide and sulfonylurea resistance in plants (see, for example, Maliga et al., Methods in Plant Molecular Biology, Cold Spring Harbor Laboratory Press, 1995, page 39).

Reporter genes have been successfully used in chloroplasts of higher plants, and high levels of recombinant protein expression have been reported. In addition, reporter genes have been used in the chloroplast of *C. reinhardtii*, but, in most cases very low amounts of protein were produced. Reporter genes greatly enhance the ability to monitor gene expression in a number of biological organisms. In chloroplasts of higher plants, β-glucuronidase (uidA, Staub and Maliga, *EMBO J.* 12:601-606, 1993), neomycin phosphotransferase (nptII, Carrer et al., *Mol. Gen. Genet.* 241:49-56, 1993), adenosyl-3-adenyltransf-erase (aadA, Svab and Maliga, *Proc. Natl. Acad. Sci., USA* 90:913-917, 1993), and the *Aequorea victoria* GFP (Sidorov et al., *Plant J.* 19:209-216, 1999) have been used as reporter genes (Heifetz, *Biochemie* 82:655-666, 2000). Each of these genes has attributes that make them useful reporters of chloroplast gene expression, such as ease of analysis, sensitivity, or the ability to examine expression in situ. Based upon these studies, other heterologous proteins have been expressed in the chloroplasts of higher plants such as *Bacillus thuringiensis* Cry toxins, conferring resistance to insect herbivores (Kota et al., *Proc. Natl. Acad. Sci., USA* 96:1840-1845, 1999), or human somatotropin (Staub et al., *Nat. Biotechnol.* 18:333-338, 2000), a potential biopharmaceutical. Several reporter genes have been expressed in the chloroplast of the eukaryotic green alga, *C. reinhardtii*, including aadA (Goldschmidt-Clermont, *Nucl. Acids Res.* 19:4083-4089 1991; Zerges and Rochaix, *Mol. Cell. Biol.* 14:5268-5277, 1994), uidA (Sakamoto et al., *Proc. Natl. Acad. Sci., USA* 90:477-501, 19933, Ishikura et al., *J. Biosci. Bioeng.* 87:307-314 1999), *Renilla luciferase* (Minko et al., *Mol. Gen. Genet.* 262:421-425, 1999) and the amino glycoside phosphotransferase from *Acinetobacter baumanii*, aphA6 (Bateman and Purton, *Mol. Gen. Genet.* 263:404-410, 2000).

In some instances, the vectors will contain elements such as an *E. coli* or *S. cerevisiae* origin of replication. Such features, combined with appropriate selectable markers, allows for the vector to be "shuttled" between the target host cell and the bacterial and/or yeast cell. The ability to passage a shuttle vector in a secondary host may allow for more convenient manipulation of the features of the vector. For example, a reaction mixture containing the vector and putative inserted polynucleotides of interest can be transformed into prokaryote host cells such as *E. coli*, amplified and collected using routine methods, and examined to identify vectors containing an insert or construct of interest. If desired, the vector can be further manipulated, for example, by performing site directed mutagenesis of the inserted polynucleotide, then again amplifying and selecting vectors having a mutated polynucleotide of interest. A shuttle vector then can be introduced into plant cell chloroplasts, wherein a polypeptide of interest can be expressed and, if desired, isolated according to a method.

A polynucleotide or recombinant nucleic acid molecule, can be introduced into plant chloroplasts using any method known in the art. A polynucleotide can be introduced into a cell by a variety of methods, which are well known in the art and selected, in part, based on the particular host cell. For example, the polynucleotide can be introduced into a plant cell using a direct gene transfer method such as electroporation or microprojectile mediated (biolistic) transformation using a particle gun, or the "glass bead method," or by pollen-mediated transformation, liposome-mediated transformation, transformation using wounded or enzyme-degraded immature embryos, or wounded or enzyme-degraded embryogenic callus (Potrykus, *Ann. Rev. Plant. Physiol. Plant Mol. Biol.* 42:205-225, 1991).

Plastid transformation is a routine and well known method for introducing a polynucleotide into a plant cell chloroplast (see U.S. Pat. Nos. 5,451,513, 5,545,817, and 5,545,818; WO 95/16783; McBride et al., *Proc. Natl. Acad. Sci., USA* 91:7301-7305, 1994). In some embodiments, chloroplast transformation involves introducing regions of chloroplast DNA flanking a desired nucleotide sequence, allowing for homologous recombination of the exogenous DNA into the target chloroplast genome. In some instances one to 1.5 kb flanking nucleotide sequences of chloroplast genomic DNA may be used. Using this method, point mutations in the chloroplast 16S rRNA and rps12 genes, which confer resistance to spectinomycin and streptomycin, can be utilized as selectable markers for transformation (Svab et al., *Proc. Natl. Acad. Sci., USA* 87:8526-8530, 1990), and can result in stable homoplasmic transformants, at a frequency of approximately one per 100 bombardments of target leaves.

Microprojectile mediated transformation also can be used to introduce a polynucleotide into a plant cell chloroplast (Klein et al., *Nature* 327:70-73, 1987). This method utilizes microprojectiles such as gold or tungsten, which are coated with the desired polynucleotide by precipitation with calcium chloride, spermidine or polyethylene glycol. The microprojectile particles are accelerated at high speed into a plant tissue using a device such as the BIOLISTIC PD-1000 particle gun (BioRad; Hercules Calif.). Methods for the transformation using biolistic methods are well known in the art (see, for example; Christou, *Trends in Plant Science* 1:423-431, 1996). Microprojectile mediated transformation has been used, for example, to generate a variety of transgenic plant species, including cotton, tobacco, corn, hybrid poplar and papaya. Important cereal crops such as wheat, oat, barley, sorghum and rice also have been transformed using microprojectile mediated delivery (Duan et al., *Nature Biotech.* 14:494-498, 1996; Shimamoto, *Curr. Opin. Biotech.* 5:158-162, 1994). The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, the glass bead agitation method, and the like.

Transformation frequency may be increased by replacement of recessive rRNA or r-protein antibiotic resistance genes with a dominant selectable marker, including, but not limited to the bacterial aadA gene (Svab and Maliga, *Proc. Natl. Acad. Sci., USA* 90:913-917, 1993). Approximately 15 to 20 cell division cycles following transformation are generally required to reach a homoplastidic state. It is apparent to one of skill in the art that a chloroplast may contain multiple copies of its genome, and therefore, the term "homoplasmic" or "homoplasmy" refers to the state where all copies of a particular locus of interest are substantially identical. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein.

In some instances, a method can be performed by introducing a recombinant nucleic acid molecule into a chloroplast, wherein the recombinant nucleic acid molecule includes a first polynucleotide, which encodes at least one polypeptide (for example, 1, 2, 3, 4, or more). In some embodiments, a polypeptide is operatively linked to a second, third, fourth, fifth, sixth, seventh, eighth, ninth, tenth and/or subsequent polypeptide. For example, several enzymes in a hydrocarbon production pathway may be linked, either directly or indirectly, such that products produced by one enzyme in the pathway, once produced, are in close proximity to the next enzyme in the pathway.

For transformation of chloroplasts, a major benefit herein can be the utilization of a recombinant nucleic acid construct which contains both a selectable marker and one or more genes of interest. Typically, transformation of chloroplasts is performed by co-transformation of chloroplasts with two constructs: one containing a selectable marker and a second containing the gene(s) of interest. Screening of such transformants is laborious and time consuming for multiple reasons. First, the time required to grow some transformed organisms is lengthy. Second, transformants must be screened both for presence of the selectable marker and for the presence of the gene(s) of interest. Typically, secondary screening for the gene(s) of interest is performed by Southern blot (see, for example PCT/US2007/072465).

In chloroplasts, regulation of gene expression generally occurs after transcription, and often during translation initiation. This regulation is dependent upon the chloroplast translational apparatus, as well as nuclear-encoded regulatory factors (see Barkan and Goldschmidt-Clermont, *Biochemie* 82:559-572, 2000; Zerges, *Biochemie* 82:583-601, 2000). The chloroplast translational apparatus generally resembles that in bacteria; chloroplasts contain 70S ribosomes; have mRNAs that lack 5' caps and generally do not contain 3' poly-adenylated tails (Harris et al., *Microbiol. Rev.* 58:700-754, 1994); and translation is inhibited in chloroplasts and in bacteria by selective agents such as chloramphenicol.

Some methods as described herein take advantage of proper positioning of a ribosome binding sequence (RBS) with respect to a coding sequence. It has previously been noted that such placement of an RBS results in robust translation in plant chloroplasts (see U.S. Application 2004/0014174, incorporated herein by reference), and that polypeptides that an advantage of expressing polypeptides in chloroplasts is that the polypeptides do not proceed through cellular compartments typically traversed by polypeptides expressed from a nuclear gene and, therefore, are not subject to certain post-translational modifications such as glycosylation. As such, the polypeptides and protein complexes produced by some methods of the invention can be expected to be produced without such post-translational modification.

One or more codons of an encoding polynucleotide can be biased to reflect chloroplast and/or nuclear codon usage. Most amino acids are encoded by two or more different (degenerate) codons, and it is well recognized that various organisms utilize certain codons in preference to others. Such preferential codon usage, which also is utilized in chloroplasts, is referred to herein as "chloroplast codon usage". The codon bias of *Chlamydomonas reinhardtii* has been reported. See U.S. Application 2004/0014174. Examples of nucleic acids encoding isoprenoid biosynthetic enzymes which are biased for expression in *C. reinhardtii* are provided in Tables 5-8. Percent identity to the native sequence (in the organism from which the sequence was isolated) may be about 50%, about 60%, about 70%, about 80%, about 90% or higher. Some vectors comprise one or more of the nucleic provided in Table 5 and/or nucleic acids with about 70% identity thereto.

The term "biased," when used in reference to a codon, means that the sequence of a codon in a polynucleotide has been changed such that the codon is one that is used preferentially in the target which the bias is for, for example, alga cells, chloroplasts. A polynucleotide that is biased for chloroplast codon usage can be synthesized de novo, or can be genetically modified using routine recombinant DNA techniques, for example, by a site directed mutagenesis method, to change one or more codons such that they are biased for chloroplast codon usage. Chloroplast codon bias can be variously skewed in different plants, including, for example, in alga chloroplasts as compared to tobacco. Generally, the chloroplast codon bias selected reflects chloroplast codon usage of the plant which is being transformed with the nucleic acids. For example, where *C. reinhardtii* is the host, the chloroplast codon usage is biased to reflect alga chloroplast codon usage (about 74.6% AT bias in the third codon position).

Any of the products described herein can be prepared by transforming an organism to cause the production by such organism of the product. An organism is considered to be a photosynthetic organism even if a transformation event destroys or diminishes the photosynthetic capability of the transformed organism (for example, exogenous nucleic acid is inserted into a gene encoding a protein required for photosynthesis).

Pathways to be Modified

The expression vectors herein can encode polypeptide(s) that promote the production of intermediates, products, precursors, and derivatives of the products described herein. For example, the expression vectors can encode polypeptide(s) that promote the production of intermediates, products, precursors, and derivatives in the isoprenoid pathway.

Isoprenoids, or terpenoids, are a group of organic chemicals related to terpenes. Terpenes are typically derived from isoprene units. Isoprene units are five-carbon units (C5). Terpenes are classified by the number of isoprene units, such as hemiterpenes (C5), monoterpenes (C10), sesquiterpenes (C15), diterpenes (C20), triterpenes (C30), tetraterpenes (C40), and polyterpenes ($C_n$, wherein "n" is equal to or greater than 45). Terpenes are hydrocarbons that can be modified (for example oxidized, methyl groups removed, etc.) or its carbon skeleton rearranged, to form derivatives of terpenes, such as isoprenoids. Isoprenoids include other steroids and lipids as well.

Terpene precursors are thought to be generated by two pathways. The mevalonate pathway, or HMG-CoA reductase pathway, generates dimethylallyl pyrophosphate (DMAPP) and isopentyl pyrophosphate (IPP), the common C5 precursor for terpenes. The non-mevalonate pathway is an alternative pathway to form DMAPP and IPP. The DMAPP and IPP may be condensed to form geranyl-diphosphate (GPP), or other precursors, such as farnesyl-diphosphate (FPP), geranylgeranyl-diphosphate (GGPP), from which higher isoprenes are formed.

An expression vector herein may encode polypeptide(s) having a role in the mevalonate pathway, such as, for example, thiolase, HMG-CoA synthase, HMG-CoA reductase, mevalonate kinase, phosphemevalonate kinase, and mevalonate-5-pyrophosphate decarboxylase. In other embodiments, the polypeptides are enzymes in the non-mevalonate pathway, such as DOXP synthase, DOXP reductase, 4-diphosphocytidyl-2-C-methyl-D-erythritol synthase, 4-diphophocytidyl-2-C-methyl-D-erythritol kinase, 2-C-methyl-D-erythritol 2,4,-cyclodiphosphate synthase, HMB-PP synthase, HMB-PP reductase, or DOXP reductoisomerase.

In other instances, an expression vector may comprise a nucleotide sequence encoding a polypeptide in an isoprenoid pathway, such as, for example, a synthase-encoding sequence. The synthase may be a C10, C15, C20, C30, or C40 synthase. In some embodiments, the synthase is botryococcene synthase, limonene synthase, 1,8 cineole synthase, α-pinene synthase, camphene synthase, (+)-sabinene synthase, myrcene synthase, abietadiene synthase, taxadiene synthase, farnesyl pyrophosphate synthase, amorphadiene synthase, (E)-α-bisabolene synthase, diapophytoene synthase, or diapophytoene desaturase. Examples of synthases and their sequences are described in Table 2.

TABLE 2

Examples of Synthases

| Synthase | Source | NCBI protein ID |
|---|---|---|
| Limonene | *M. spicata* | 2ONH_A |
| Cineole | *S. officinalis* | AAC26016 |
| Pinene | *A. grandis* | AAK83564 |
| Camphene | *A. grandis* | AAB70707 |
| Sabinene | *S. officinalis* | AAC26018 |
| Myrcene | *A. grandis* | AAB71084 |
| Abietadiene | *A. grandis* | Q38710 |
| Taxadiene | *T. brevifolia* | AAK83566 |
| FPP | *G. gallus* | P08836 |
| Amorphadiene | *A. annua* | AAF61439 |
| Bisabolene | *A. grandis* | O81086 |
| Diapophytoene | *S. aureus* | |
| Diapophytoene desaturase | *S. aureus* | |
| GPPS-LSU | *M. spicata* | AAF08793 |
| GPPS-SSU | *M. spicata* | AAF08792 |
| GPPS | *A. thaliana* | CAC16849 |
| GPPS | *C. reinhardtii* | EDP05515 |
| FPP | *E. coli* | NP_414955 |
| FPP | *A. thaliana* | NP_199588 |
| FPP | *A. thaliana* | NP_193452 |
| FPP | *C. reinhardtii* | EDP03194 |
| IPP isomerase | *E. coli* | NP_417365 |
| IPP isomerase | *H. pluvialis* | ABB80114 |
| Limonene | *L. angustifolia* | ABB73044 |
| Monoterpene | *S. lycopersicum* | AAX69064 |
| Terpinolene | *O. basilicum* | AAV63792 |
| Myrcene | *O. basilicum* | AAV63791 |
| Zingiberene | *O. basilicum* | AAV63788 |
| Myrcene | *Q. ilex* | CAC41012 |
| Myrcene | *P. abies* | AAS47696 |
| Myrcene, ocimene | *A. thaliana* | NP_179998 |
| Myrcene, ocimene | *A. thaliana* | NP_567511 |
| Sesquiterpene | *Z. mays*; B73 | AAS88571 |
| Sesquiterpene | *A. thaliana* | NP_199276 |
| Sesquiterpene | *A. thaliana* | NP_193064 |
| Sesquiterpene | *A. thaliana* | NP_193066 |
| Curcumene | *P. cablin* | AAS86319 |
| Farnesene | *M. domestica* | AAX19772 |
| Farnesene | *C. sativus* | AAU05951 |
| Farnesene | *C. junos* | AAK54279 |
| Farnesene | *P. abies* | AAS47697 |
| Bisabolene | *P. abies* | AAS47689 |
| Sesquiterpene | *A. thaliana* | NP_197784 |
| Sesquiterpene | *A. thaliana* | NP_175313 |
| GPP Chimera | | |
| GPPS-LSU + SSU fusion | | |
| Geranylgeranyl reductase | *A. thaliana* | NP_177587 |
| Geranylgeranyl reductase | *C. reinhardtii* | EDP09986 |
| Chlorophyllidohydrolase | *C. reinhardtii* | EDP01364 |
| Chlorophyllidohydrolase | *A. thaliana* | NP_564094 |

TABLE 2-continued

Examples of Synthases

| Synthase | Source | NCBI protein ID |
|---|---|---|
| Chlorophyllidohydrolase | A. thaliana | NP_199199 |
| Phosphatase | S. cerevisiae | AAB64930 |
| FPP A118W | G. gallus | |

The synthase may also be β-caryophyllene synthase, germacrene A synthase, 8-epicedrol synthase, valencene synthase, (+)-δ-cadinene synthase, germacrene C synthase, (E)-β-farnesene synthase, casbene synthase, vetispiradiene synthase, 5-epi-aristolochene synthase, aristolchene synthase, α-humulene, (E,E)-α-farnesene synthase, (−)-β-pinene synthase, γ-terpinene synthase, limonene cyclase, linalool synthase, (+)-bornyl diphosphate synthase, levopimaradiene synthase, isopimaradiene synthase, (E)-γ-bisabolene synthase, copalyl pyrophosphate synthase, kaurene synthase, longifolene synthase, γ-humulene synthase, δ-selinene synthase, β-phellandrene synthase, terpinolene synthase, (+)-3-carene synthase, syn-copalyl diphosphate synthase, α-terpineol synthase, syn-pimara-7,15-diene synthase, ent-sandaaracopimaradiene synthase, sterner-13-ene synthase, E-β-ocimene, S-linalool synthase, geraniol synthase, γ-terpinene synthase, linalool synthase, E-β-ocimene synthase, epi-cedrol synthase, α-zingiberene synthase, guaiadiene synthase, cascarilladiene synthase, cis-muuroladiene synthase, aphidicolan-16b-ol synthase, elizabethatriene synthase, sandalol synthase, patchoulol synthase, zinzanol synthase, cedrol synthase, scareol synthase, copalol synthase, or manool synthase.

Pathways utilized for methods described herein may involve enzymes present in the cytosol, in a plastid (for example, chloroplast), or both. Exogenous nucleic acids encoding the enzymes of certain embodiments may be introduced into a host cell, such that the enzyme encoded is active in the cytosol or in a plastid, or both. In some embodiments, a naturally occurring enzyme which is present in one intracellular compartment (for example, in the cytosol) may be expressed in a different intracellular locale (for example, in the chloroplast), or in both the naturally occurring and non-naturally occurring locales following transformation of the host cell.

To illustrate this concept, and merely by way of example, a non-vascular photosynthetic microalga species can be genetically engineered to produce an isoprenoid, such as limonene (a molecule of high value in the specialty chemical and petrochemical industries). Limonene is a monoterpene that is a pure hydrocarbon, only composed of hydrogen and carbon atoms. Limonene is not naturally produced in the species, *Chlamydomonas rheinhardii*. Production of limonene in these microalgae can be achieved by engineering the microalgae to express the heterologous enzyme limonene synthase in the chloroplast. Limonene synthase can convert the terpene precursor geranyl pyrophosphate into limonene. Unlike limonene, geranyl pyrophosphate is naturally present in the chloroplast of microalgae. The expression of the limonene synthase can be accomplished by inserting the heterologous gene encoding limonene synthase into the chloroplast genome of the microalgae. The modified strain of microalgae is then made homoplasmic to ensure that the limonene gene will be stably maintained in the chloroplast genome of all descendents. A microalgae is homoplasmic for a gene when the inserted gene is present in all copies of the chloroplast genome. It is apparent to one of skill in the art that a chloroplast may contain multiple copies of its genome, and therefore, the term "homoplasmic" or "homoplasmy" refers to the state where all copies of a particular locus of interest are substantially identical. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein.

Expression.

Chloroplasts are a productive organelle of photosynthetic organisms and a site of large of amounts of protein synthesis. Any of the expression vectors herein may be selectively adapted for chloroplast expression. A number of chloroplast promoters from higher plants have been described in Kung and Lin, *Nucleic Acids Res.* 13: 7543-7549 (1985). Gene products may be expressed from the expression vector in the chloroplast. Gene products encoded by expression vectors may also be targeted to the chloroplast by chloroplast targeting sequences. For example, targeting an expression vector or the gene product(s) encoded by an expression vector to the chloroplast may further enhance the effects provided by the regulatory control sequences and sequence(s) encoding a protein or peptide that allows or improves production of a fuel molecule.

Various combinations of the chloroplast targeting described herein may be embodied and combined with other features described herein. For example, a nucleotide sequence encoding a terpene synthase may be operably linked to a nucleotide sequence encoding a chloroplast targeting sequence. A host cell may be transformed with an expression vector encoding limonene synthase targeted to the chloroplast, and thus, may produce more limonene synthase as compared to a host cell transformed with an expression vector encoding limonene synthase but not a chloroplast targeting sequence. The increased limonene synthase expression may produce more of the limonene in comparison to the host cell that produces less.

In yet another example, an expression vector comprising a nucleotide sequence encoding an enzyme that produces a product (for example fuel product, fragrance product, insecticide product) not naturally produced by the organism by using precursors that are naturally produced by the organism as substrates, is targeted to the chloroplast. By targeting the enzyme to the chloroplast, production of the product may be increased in comparison to a host cell wherein the enzyme is expressed, but not targeted to the chloroplast. Without being bound by theory, this may be due to increased precursors being produced in the chloroplast and thus, more product may be produced by the enzyme encoded by the introduced nucleotide sequence.

Methods

A product (for example fuel product, fragrance product, insecticide product) may be produced by a method that comprises the step of growing/culturing a non-vascular organism transformed by one or more of the nucleic acids herein. The methods herein can further comprise the step of transforming the organism. Transformation can occur using any method known in the art or described herein. The methods herein can further comprise the step of collecting the product produced by the organism.

The methods herein may further comprise the step of providing to the organism a source of inorganic carbons, such as flue gas. In some instances, the inorganic carbon source provides all of the carbons necessary for making the product (for example, fuel product). The growing/culturing step preferably occurs in a suitable medium, such as one that has minerals and/or vitamins.

In a related yet distinct aspect, a method for producing a product (for example fuel product, fragrance product, insecticide product) comprises: transforming a photosynthetic organism with an expression vector, growing the organism; and collecting the product from the organism. The expression vector is typically the expression vector described herein, and is specifically used to add additional biosynthetic capacity to an organism or to modify an existing biosynthetic pathway within the organisms, either with the intension of increasing or allowing the production of a molecule by the photosynthetic organism.

The methods herein comprise selecting genes that are useful to produce products, such as fuels, fragrances, and insecticides, transforming a cell of a photosynthetic organism with such gene(s), and growing such organisms under conditions suitable to allow the product to be produced. Organisms for use herein can be cultured in conventional fermentation bioreactors, which include, but are not limited to, batch, fed-batch, cell recycle, and continuous fermentors. Further, they may be grown in photobioreactors (see for example US Appl. Publ. No. 20050260553; U.S. Pat. Nos. 5,958,761; 6,083,740). Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

A host organism may also be grown on land, for example, landfills. In some cases, host organism(s) are grown near ethanol production plants or other facilities or regions (for example, cities, highways, etc.) generating $CO_2$. As such, the methods herein contemplate business methods for selling carbon credits to ethanol plants or other facilities or regions generating $CO_2$ while making fuels by growing one or more of the modified organisms described herein near the ethanol production plant.

Further, the organisms may be grown in outdoor open water, such as ponds, the ocean, sea, rivers, waterbeds, marsh water, shallow pools, lakes, reservoirs, etc. When grown in water, the organisms can be contained in a halo like object comprising of lego-like particles. The halo object encircles the algae and allows it to retain nutrients from the water beneath while keeping it in open sunlight.

In some instances, organisms can be grown in containers wherein each container comprises 1 or 2 or a plurality of organisms. The containers can be configured to float on water. For example, a container can be filled by a combination of air and water to make the container and the host organism(s) in it buoyant. A host organism that is adapted to grow in fresh water can thus be grown in salt water (for example, the ocean) and vice versa. This mechanism allows for automatic death of the organism if there is any damage to the container.

In some instances a plurality of containers can be contained within a halo-like structure as described above. For example, up to 100, 1,000, 10,000, 100,000, or 1,000,000 containers can be arranged in a meter-square of a halo-like structure.

In some embodiments, the product (for example fuel product, fragrance product, insecticide product) is collected by harvesting the organism. The product may then be extracted from the organism.

In some embodiments, the expression of the product (for example fuel product, fragrance product, insecticide product) is inducible. The product may be induced to be expressed. Expression may be inducible by light. In yet other embodiments, the production of the product is autoregulatable. The product may form a feedback loop, wherein when the product (for example fuel product, fragrance product, insecticide product) reaches a certain level, expression of the product may be inhibited. In other embodiments, the level of a metabolite of the organism inhibits expression of the product. For example, endogenous ATP produced by the organism as a result of increased energy production to express the product, may form a feedback loop to inhibit expression of the product. In yet another embodiment, production of the product may be inducible, for example, by light or an exogenous agent. For example, an expression vector for effecting production of a product in the host organism may comprise an inducible regulatory control sequence that is activated or inactivated by an exogenous agent.

The methods described herein can relate to methods for screening for new genes/expression vectors to create any of the fuel products described herein. Such methods comprise the steps of: (1) inserting a candidate expression vector of nucleic acids into a photosynthetic organism, (2) collecting a putative fuel product produced there from, (3) applying the putative fuel product to a mass spectrometer to determine a characteristic of the putative fuel product, and whether it may be used as a fuel product. In some embodiments, step (2) may comprise collecting a known fuel product and whether a candidate expression vector increases production of the fuel product relative to a photosynthetic organism without the candidate expression vector.

The present disclosure is further illustrated by the following examples, which should not be construed as limiting in any way. The experimental procedures to generate the data shown are discussed in more detail below. The disclosure has been described in an illustrative manner, and it is to be understood that the terminology used is intended to be in the nature of description rather than of limitation.

EXAMPLE 1

Cracking of the sesquiterpene, cuparene, was achieved with the processes provided herein. In this example, a 10-ring molecular sieve catalytic composition was selected to demonstrate the catalytic cracking of cuparene. The zeolite was a ZSM-5 material known as SN27 which has a relatively high alumina content for ZSM-5 type zeolites of about 27/1 $SiO_2/Al_2O_3$. This material was converted to the proton form by exchange with ammonium cations followed by calcination at about 500° C. in a pulse reactor prior to use.

Figure 1B:
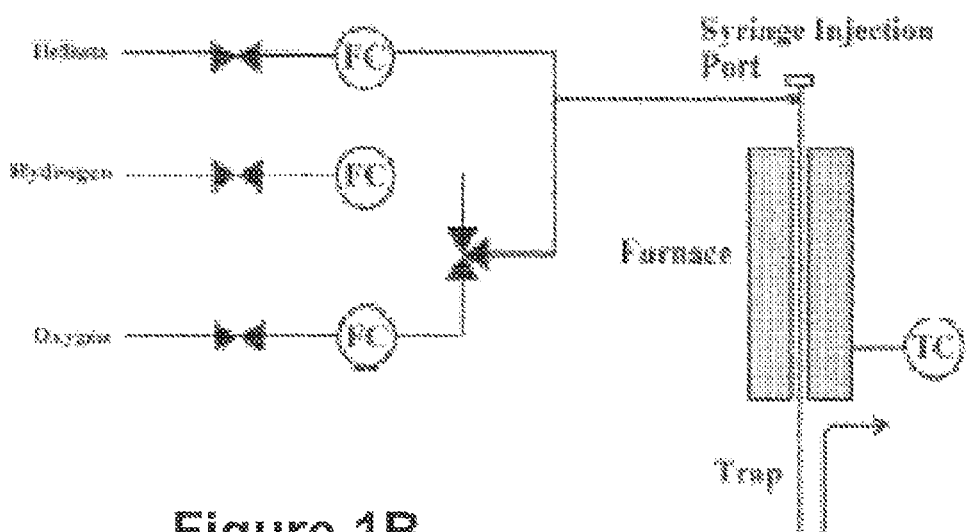
FIG. 1B is a schematic diagram showing the pulse reactor in operation.

A pulse reactor was constructed to study catalytic reactions of the biologically-derived hydrocarbons described herein. Design criteria include minimizing the quantities of reactants necessary to produce reliable results and allowing for evaluation of the products and product distributions. As shown in FIG. 1A, the pulse reactor 10 is constructed of a 30-cm-long quartz tube 20, capable of withstanding temperatures over 1000° C. The quartz tube is equipped with a gas inlet 24 and a gas outlet 28 at its respective ends. It has a fritted disk 30 in the center which is used to support a catalyst sample (not shown). Quartz wool 40 is placed on the top and bottom of the catalyst in the reactor to hold it in place. An O-ring connector 44 at the top allows for a syringe injection port 50, and another O-ring joint 60 at the bottom is used to connect a removable U-shaped trap 70. Optionally, an additional tube 80 can be attached to the O-ring joint 60 to prevent condensation of the products on the O-ring. The main tube 20 can be placed in a tubular furnace and a temperature controller (not shown) is attached. FIG. 1B is a schematic diagram showing the pulse reactor in operation. Briefly, a flow stream of a carrier gas is typically provided through pressure and flow regulators. The carrier gas flows past the syringe injection port, down the tube, over the catalyst sample, and into the trap. The carrier gas carries the hydrocarbon reactants to the catalyst, as well as optionally provides certain reaction atmosphere. For example, the carrier gas can be helium or nitrogen (inert atmosphere), hydrogen (reducing atmosphere), or oxygen (oxidizing atmosphere). The catalyst sample may be pretreated in any of the desired atmospheres and at any temperature prior to introduction of pulses of reactant. The reactor is brought to the desired reaction temperature in a furnace, and small quantities of the hydrocarbon reactants are injected into the flowing stream which carries this "pulse" to the catalyst at reaction temperature. To collect reaction products, the U-tube trap 70 at the bottom is immersed in a cold trap equipped with liquid nitrogen. Products of the catalytic reaction freeze in the U-tube trap and can be retrieved by removing the U-tube trap and washing it with a solvent (e.g., methanol). The products can then be analyzed with GC/MS for qualitative determination of product species and/or GC with FID detector for quantitative determination. In both the GC and GC/MS systems, identical chromatographic columns with identical column temperature programming profiles are used. These are 50-m PONA capillary columns, and splitting injectors are used on both devices.

Cuparene is a C15 molecule, such that it has a high boiling point (about 275° C.) and therefore can require adjustment of chromatographic procedure for analysis. A GC/MS system was used for analysis of cracking products.

Figure 1C:
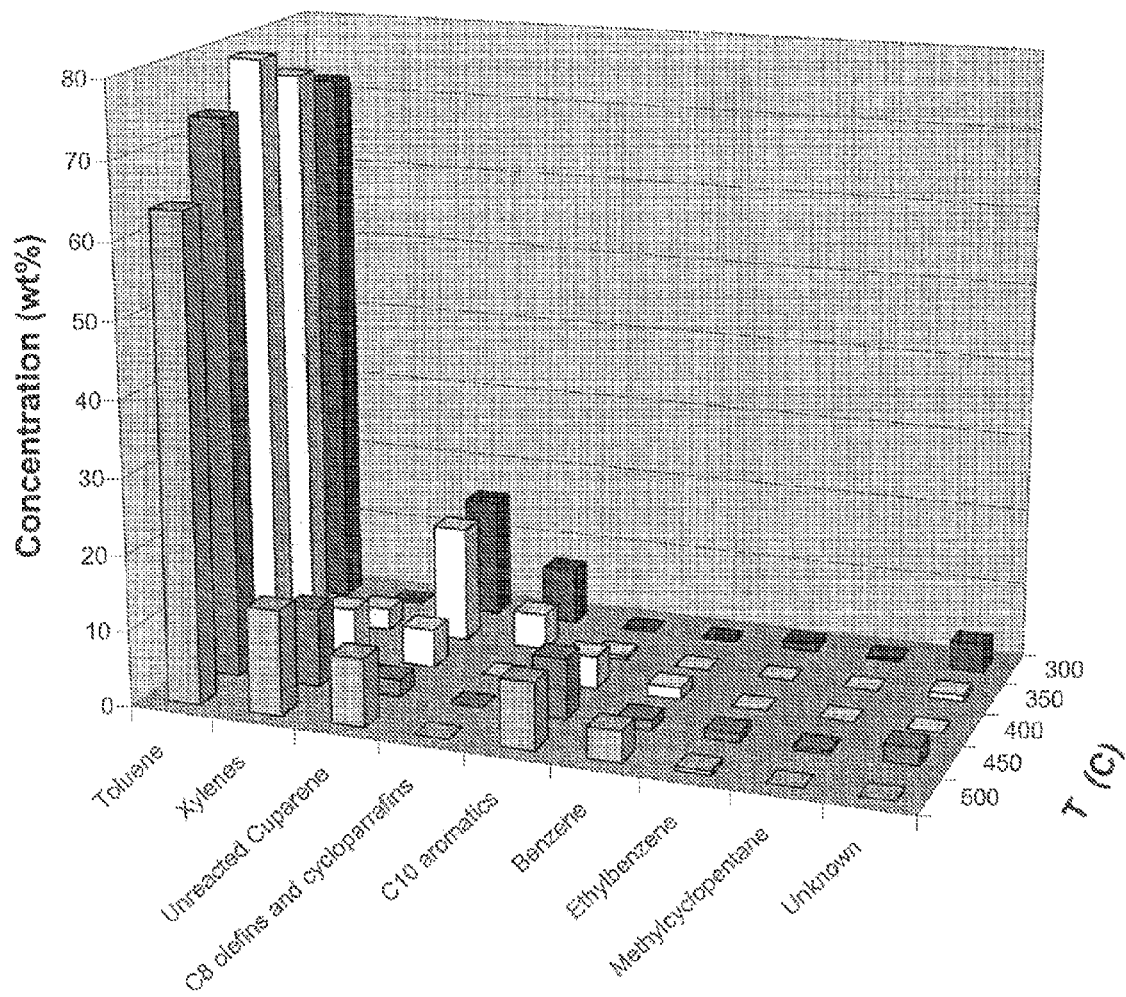
FIG. 1C summarizes the various cracking products from cuparene obtained for different temperatures.

Experiment for catalytic cracking of cuparene cracking were conducted on the fully protonated form of SN27. The cracking conditions were 500° C. and the cuparene was provided to a pulse reactor with a helium carrier gas (100 cc/min) at 25 µL pulses. The conversion of cuparene to cracking products was near 100% and the major products were toluene, benzene, xylenes, ethylbenzene, and heavier aromatics. In order to avoid some aromatics such as benzene and the xylenes cracking was also performed under cracking conditions of lower temperatures: 450, 400, 350, and 300° C. A summary of the various cracking products obtained for the different temperatures is shown in FIG. 1C.

EXAMPLE 2

LZY-72 is a Union Carbide Y-type zeolite which is often used as a cracking catalyst. The catalytic composition used in this example began with the LZY-72 base which is generally in a sodium form, from which the base was ion-exchanged with $NH_4NO_3$ aqueous solution to yield the ammonium form of the zeolite. Upon heating, the ammonium zeolite converts to the proton form with the elimination of ammonia. The proton form of the zeolite acts as a strong solid acid. Y-type zeolites have a 3-dimensional pore network with pore mouths of about 8.6 Å which opens into larger, nearly spherical cages of free diameter about 13 Å.

A second catalyst, SN27, is a ZSM-5 zeolite base material manufactured by VAW-AG in Germany. It has a $SiO_2/Al_2O_3$ ratio of 27/1. This zeolite was also supplied in the sodium form, and a similar ammonium exchange procedure followed by heating was used to convert it to a strong acid. ZSM-5 zeolites are characterized by a two-dimensional channel system which is roughly cylindrical in shape with a pore diameter of about 5.5 Å.

Figure 2A:
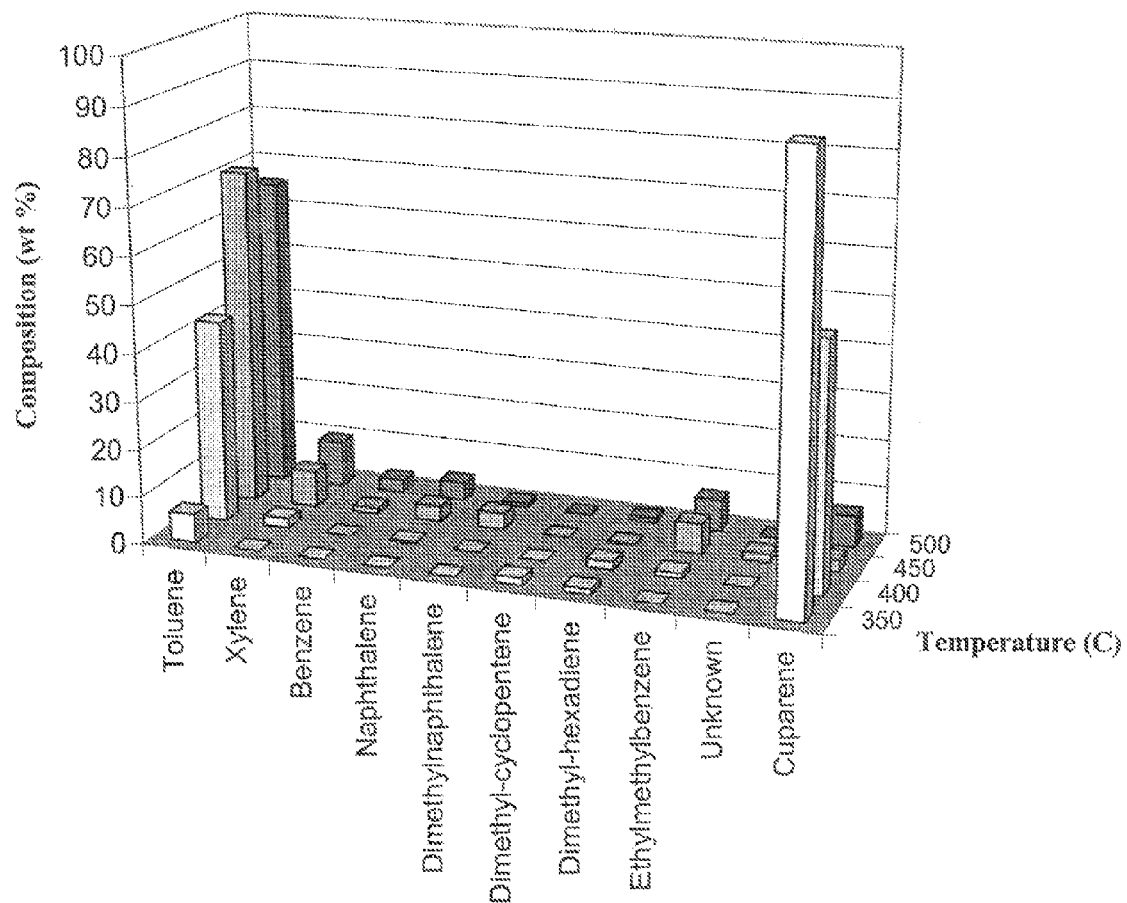
FIG. 2A shows the cracking products of cuparene at various reaction temperatures using SN27 catalyst.

Cracking of a sesquiterpene, in this example, cuparene, was performed by contacting cuparene with the SN27 catalyst and the products resulting from the process are summarized in FIG. 2A. As illustrated in FIG. 2A, high cuparene conversions were obtained at high temperatures (450-500° C.) and toluene was the major product, with smaller amounts of benzene, xylenes, and ethyl-methylbenzene.

Figure 2B:
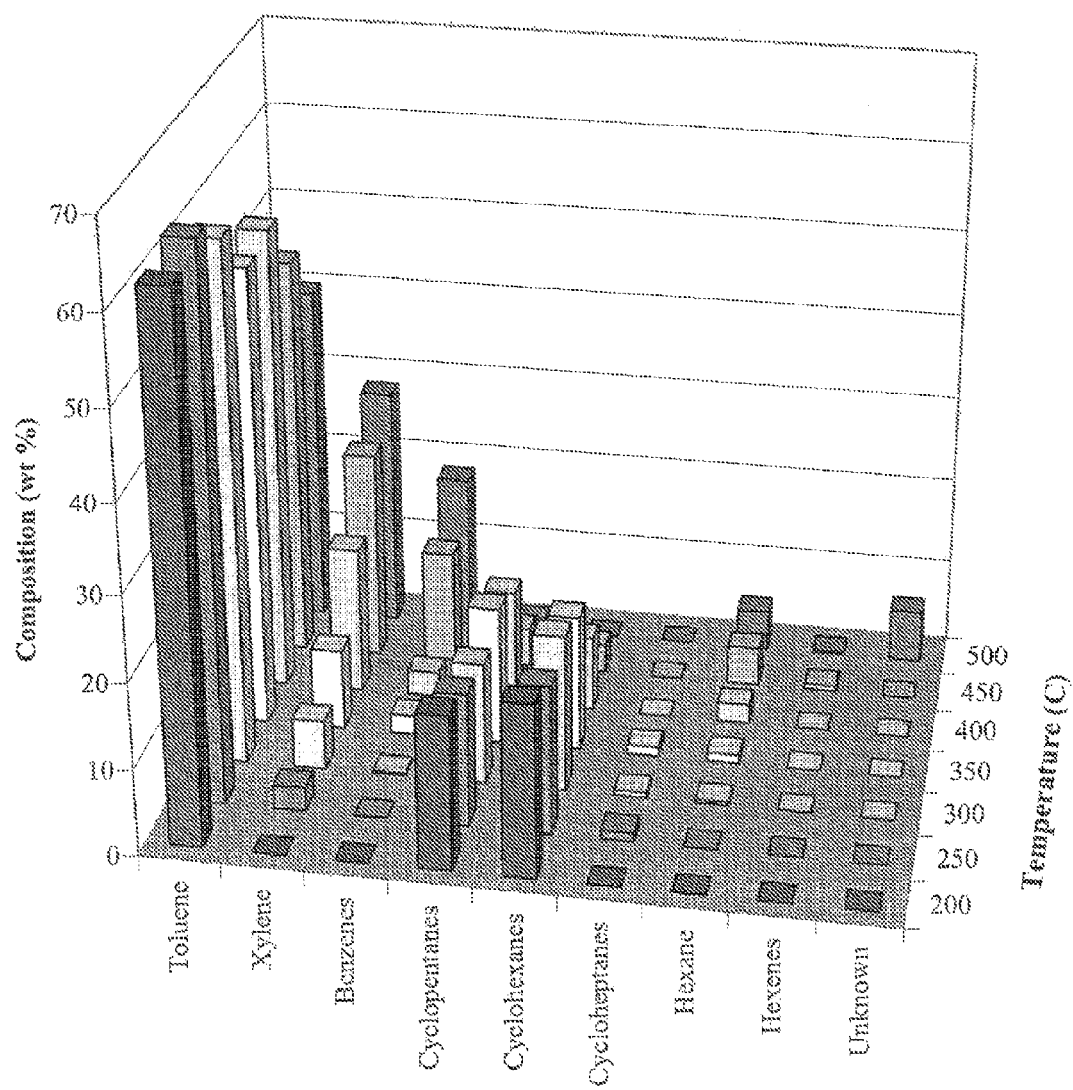
FIG. 2B shows the cracking products of cuparene at various reaction temperatures using LZY-72 catalyst.
Figure 2C:
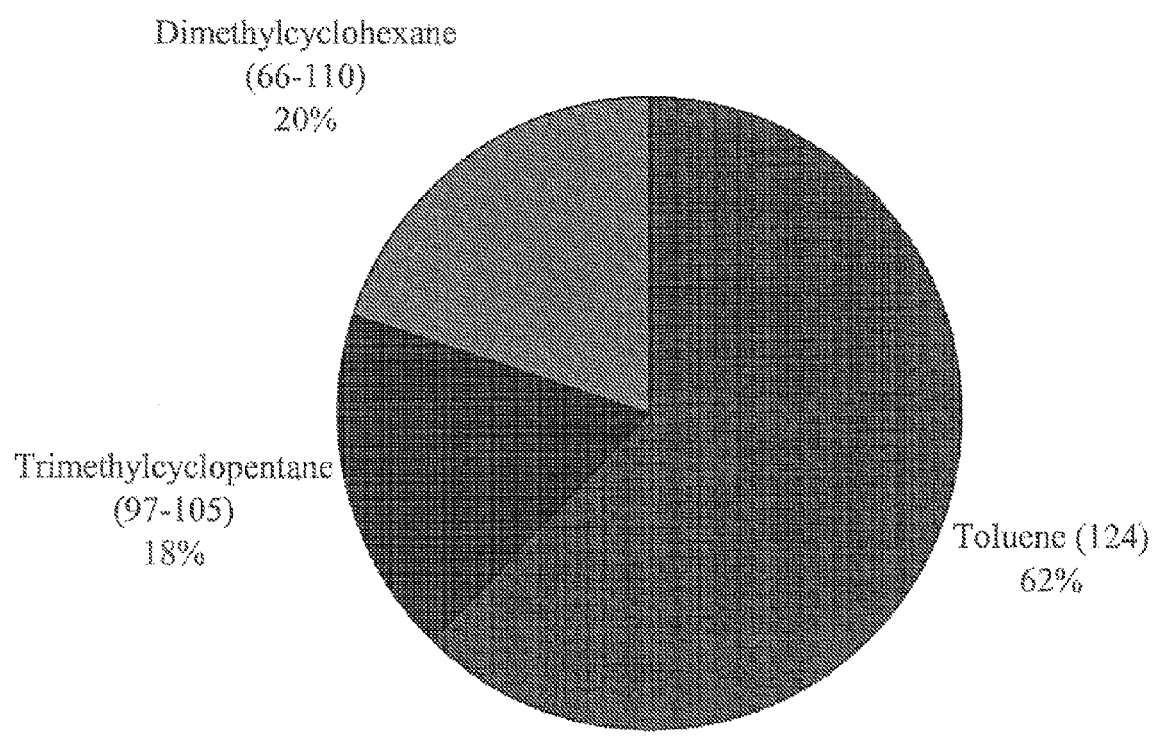
FIGS. 2C, 2D, and 2E summarize the quantifications of the cracking products of cuparene catalyzed by LZY-72 at three different temperatures.
Figure 2D:
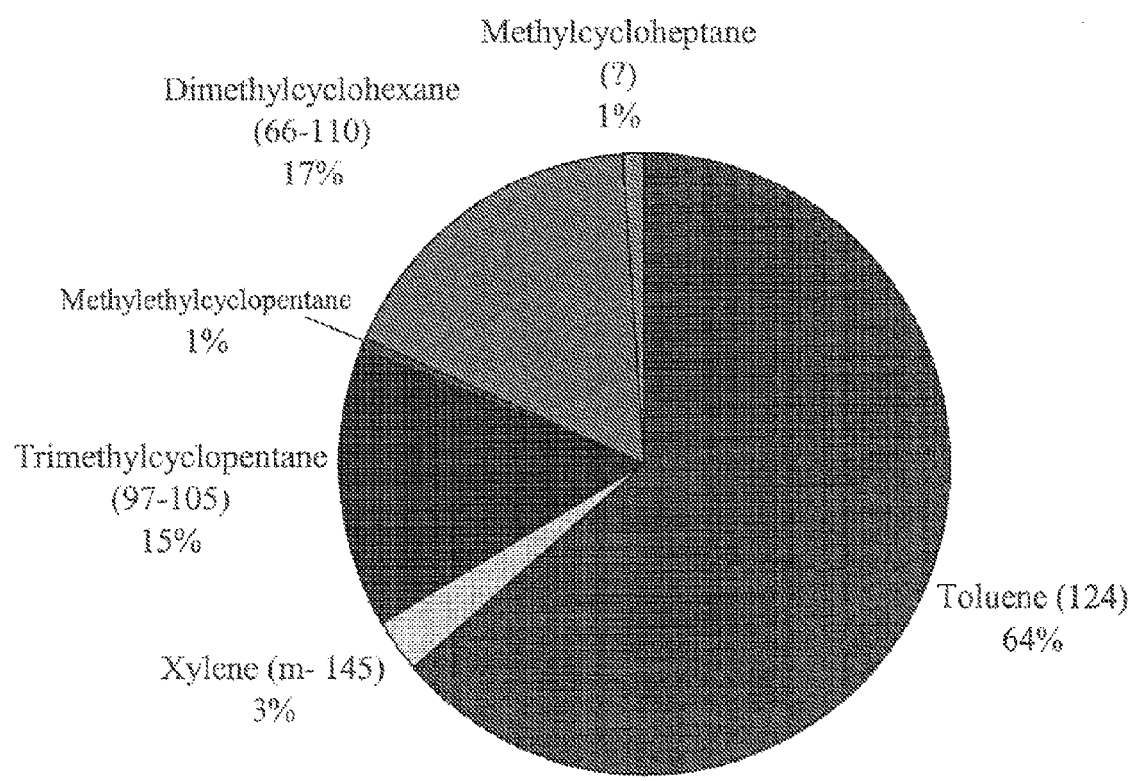
Figure 2E:
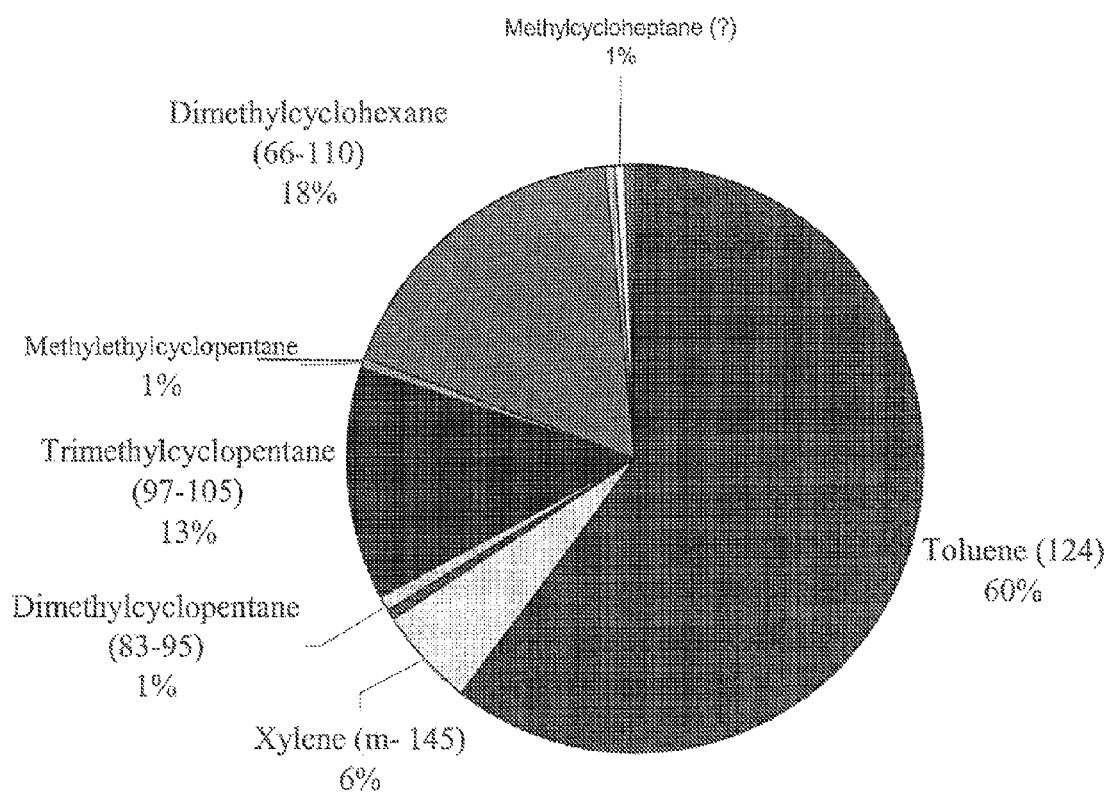

Using the LZY-72 catalyst, cuparene was cracked at much lower temperatures into high octane number components as summarized in FIG. 2B. The major component in all products from cracking of cuparene with the LZY-72 catalyst was toluene. Xylene and benzene derivatives were produced preferentially at higher temperatures, similar to the results over the SN27 catalyst. At low temperatures, derivatives of cyclopentane and cyclohexane were produced in significant quantities, with very little benzene, indicating a high octane fuel product or fuel component that may be suitable for blending or as a fuel product. FIGS. 2C, 2D, and 2E illustrate the compositions from the cracking of cuparene with the LZY-72 zeolite at 200, 250 and 300 C, respectively. The numbers in parenthesis indicate the range of octane numbers for the various components.

The hydrogen-to-carbon (H/C) ratio of the products from cuparene cracking was also observed. The reactant cuparene is $C_{15}H_{22}$, with an H/C ratio is 1.47. If cuparene cracked exactly into its two basic rings, the products would be would be 54.5% trimethylcyclopentene, $C_8H_{14}$, and 45.5% toluene, $C_7H_8$, and this mixture would have the identical H/C ratio of the parent molecule, 1.47. However, the cracking products mixture of this example contains trimethylcyclopentanes and dimethylcyclohexanes instead of trimethylcyclopentene. Since the saturated napthenes have a higher H/C ratio than the unsaturated napthenes, we might expect the overall product to contain a higher H/C content than the reactant; as a result, the reaction would require hydrogen addition. However, the measured H/C ratio of the actual product shown in FIG. 2B is 1.43 and this is possible without hydrogen addition because the actual toluene weight fraction (62.1%) exceeds 45.5%. Therefore, a cracking product comprises a high octane product that is suitable for a combustion fuel product such as gasoline or jet fuel.

Also, more cuparene was cracked with less aromatics using the LZY-52 catalyst as compared to the SN27 catalyst, at most temperatures. This difference may result from the difference in pore sizes. SN27 has a pore diameter of about 5.5 Å, and the pore structure is known to admit aromatic rings, but the size and shape of cuparene may be slightly too large to fit into the pores. High temperatures appear to be required for catalytic cracking with SN27, but the selectivity suffers at higher temperatures. With pores of about 8.6 Å, LZY-52 appears better able to accommodate the cuparene molecule.

In another instance of the example, there are no measurable alkylcyclopentenes or alkylcyclohexenes in the product, which can be undesirable in fuel products such as gasoline. Such unsaturates, though possibly acceptable, could cause difficulties in reactivity in large quantities in gasoline. Benzene, another undesirable molecule in a fuel product such as gasoline was also not present in measurable quantities in some instances.

EXAMPLE 3

Zeolite beta was obtained from PQ Catalysts (now part of Zeolyst International). The material is known as Valfor CP811BL-25. It has a $SiO_2/Al_2O_3$ ratio of about 25, and was supplied in its acidic (fully protonated) form. The zeolite beta was converted from a loose powder to 20-40 mesh particles prior to loading into a pulse reactor via pressing it into pellets, grinding in a mortar and pestle, and sieving.

Similar to zeolite Y as demonstrated in Example 2, zeolite beta has a 12-ring, three-dimensional pore system. Unlike zeolite Y, zeolite beta can be synthesized in much higher $SiO_2/Al_2O_3$ ratios. This gives rise to a lower density of protonic sites, but each individual site is generally stronger in zeolite beta.

Figure 3A:
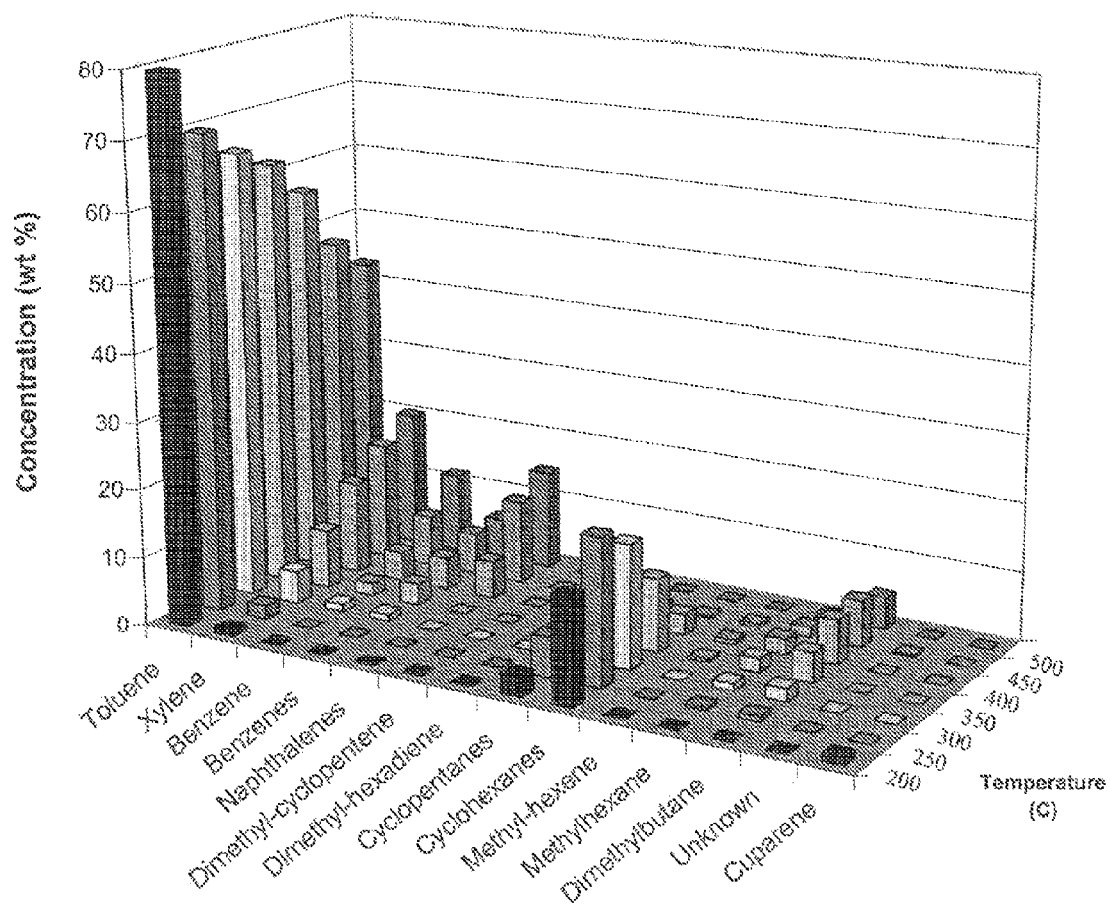
FIG. 3A shows the cracking products of cuparene at various reaction temperatures using zeolite beta catalyst.
Figure 3B:
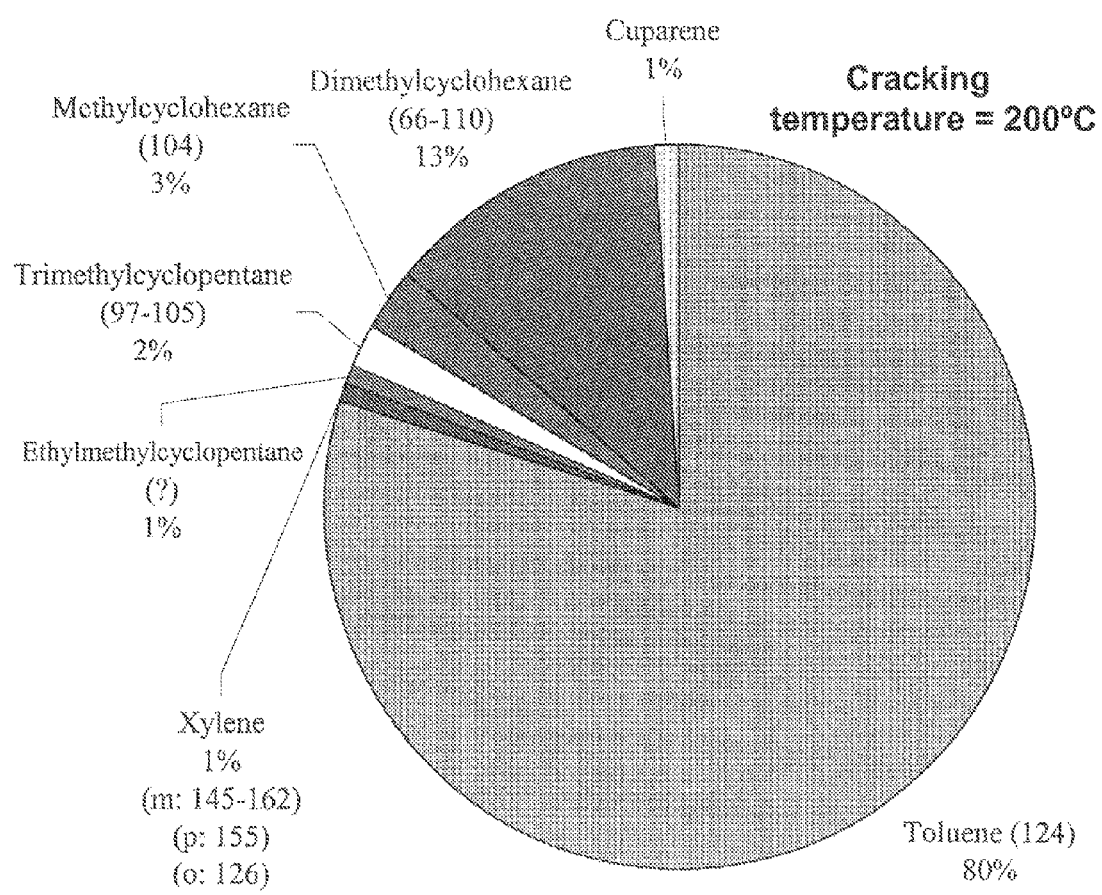
FIGS. 3B and 3C summarize the quantifications of the cracking products of cuparene catalyzed by zeolite beta at two different temperatures.
Figure 3C:
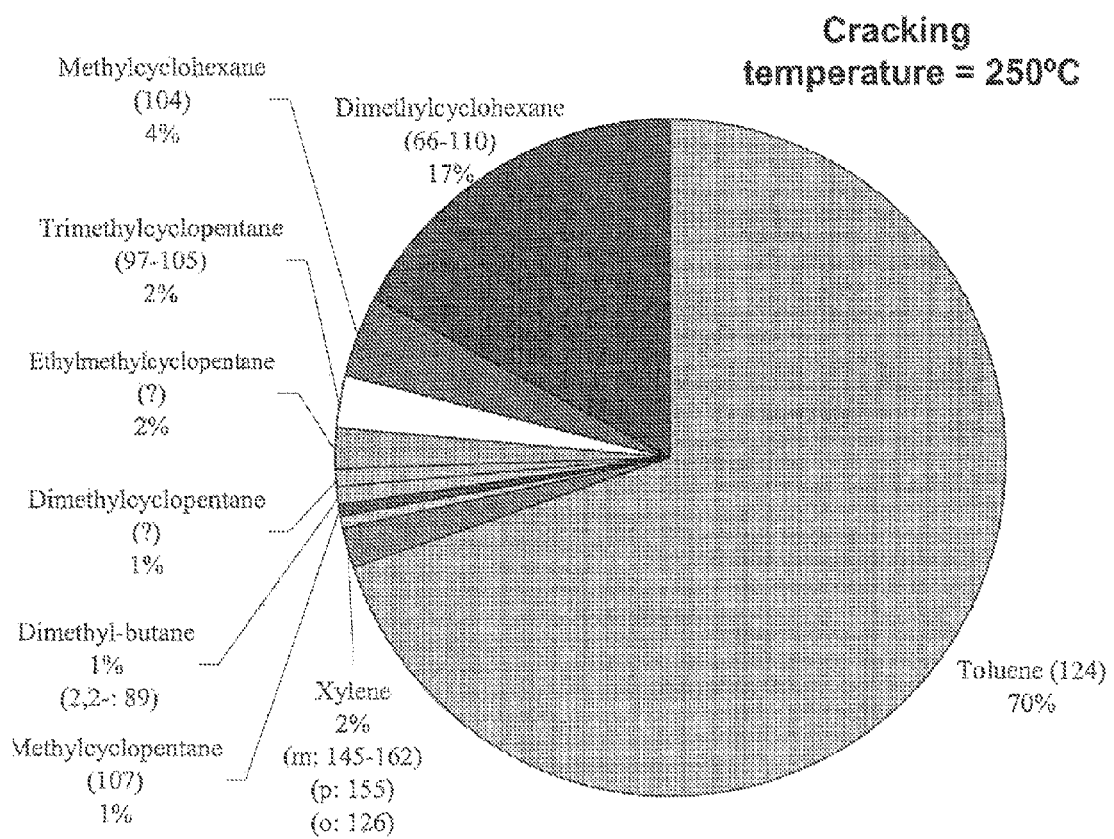

A process of cracking cuparene was performed in a pulse reactor at catalytic cracking condition and contacting the cuparene with zeolite beta. High cuparene conversions were observed at conditions with temperature as low as 200° C. and toluene was the major product at all temperatures utilized, 200 to 500° C. FIG. 3A details the temperature sensitivity of cuparene cracking using zeolite beta (Valfour CP811BL-25) catalyst and the products obtained therefrom. FIGS. 3B and 3C illustrates product detail for cuparene cracking using zeolite beta (Valfour CP811BL-25) catalyst at 200 and 250 C. The numbers in parentheses indicate the octane number of the species. A range is indicated where different isomers would have different octane numbers.

EXAMPLE 4

The ammonium form of ELZ-L zeolite was prepared starting with the potassium form (Linde Molecular Sieves). 10 g of the potassium form of the zeolite were slurried in a solution containing 10 g of ammonium acetate in 50 cc of water. The mixture was warmed and stirred overnight, then the solution was filtered off, and the process was repeated a second time. This material was dried at 125° C. overnight before being used. Microbalance desorption experiments show strong proton content of the material after drying at 500° C.

Cracking of cuparene was carried out in a pulse reactor by contacting the cuparene with the ELZ-Z catalytic composition. The cracking products were analyzed by GC and GC/MS. The chromatograms exhibited a wide array of cracking products, particularly at lower temperatures. Only peaks with areas at least 1% of the largest peak area on the chromatogram were analyzed. The neglected peaks contributed about 0.3% each to the total number area of all peaks on a chromatogram. Retained peaks were then identified by library search using a NIST MS fingerprint database.

Figure 4:
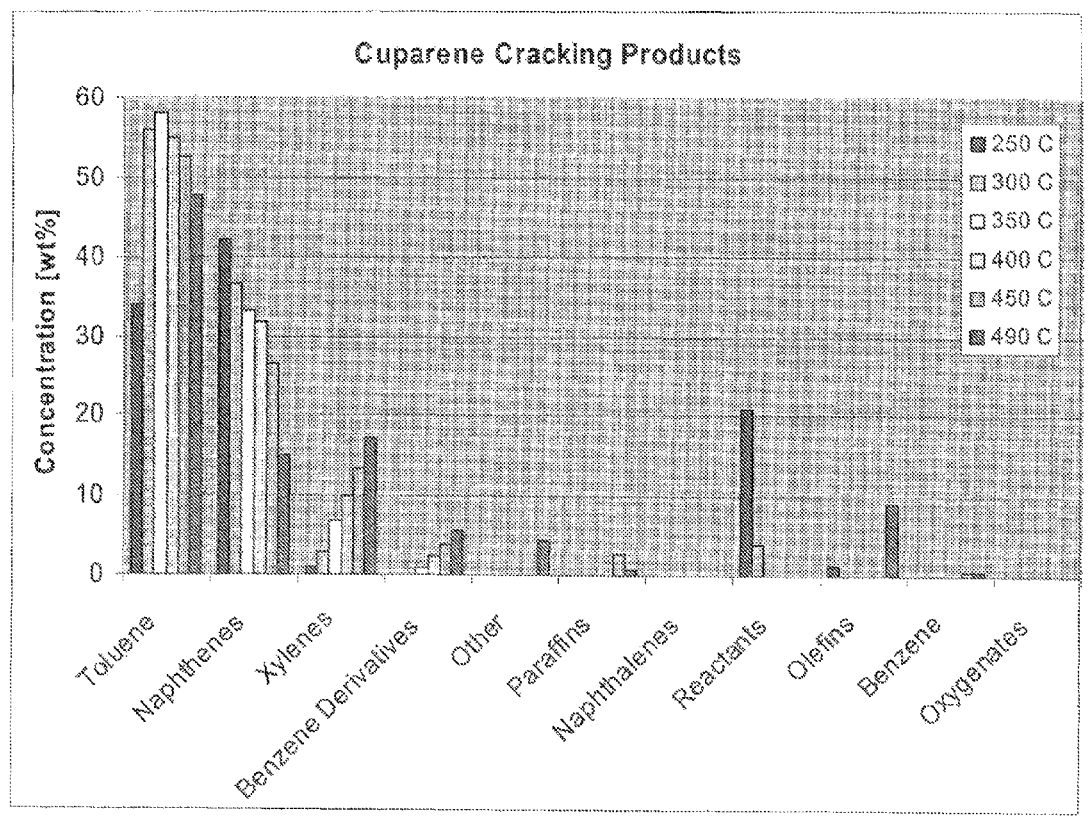
FIG. 4 shows the cracking products of cuparene at various reaction temperatures using ELZ-L zeolite catalyst.

Cracking cuparene with the ELZ-L catalyst produced primarily toluene and naphthenes (cyclic alkanes) at all temperatures tested, as shown in FIG. 4. Higher cracking temperatures enhanced production of xylenes (dimethyl benzene) and other benzene derivatives (trimethyl benzene, ethyl benzene, methyl-isopropyl benzene) at the cost of naphthenes and some toluene. Less than 1% of the products were benzene. Olefins only made up 1 and 9% of the cracking products at 250 and 490° C., respectively. No significant amounts of naphthalenes (C10+ aromatics) or oxygenates (oxygen containing molecules) were produced.

The ELZ-L catalyst yielded cracking products similar to the LZY-72 and zeolite beta catalysts demonstrated in Example 2 and 3. In particular, LZY-72 and ELZ-L produced similar amounts of toluene and naphthenes. However, the LZY-72 catalyst produced more xylene and benzene than ELZ-L does at corresponding temperatures, but LZY-72 also had better conversion of cuparene at 250 and 300° C. Zeolite beta produces more toluene than ELZ-L at 400° C. and below. Like LZY-72, zeolite beta also produced more xylene and benzene than ELZ-L does at comparable temperatures. Zeolite beta also produced naphthalenes at 400° C. and above, while neither LZY-72, nor ELZ-L, produced significant amounts of naphthalene at any temperature. Compared to zeolite beta, ELZ-L exhibited poorer conversion of cuparene at 300° C. or less.

Cuparene cracking over zeolite beta, LZY-72, and ELZ-L produced substantial amounts of toluene; never less than 30% and usually 50% or better as demonstrated in this example and Example 2 and Example 3. At high temperatures (450+° C.), xylenes were the second most abundant product at about 20%. Decreasing the cracking temperatures to between 200 and 300° C. produces about 30% naphthenes using LZY-72 and ELZ-L catalysts. Moderate temperatures also reduce benzene and olefin formation. All three of the large pore molecular sieves for cuparene cracking appear to be excellent candidates for cracking cuparene into high octane fuel products, components, or additives.

EXAMPLE 5

Figure 5A:
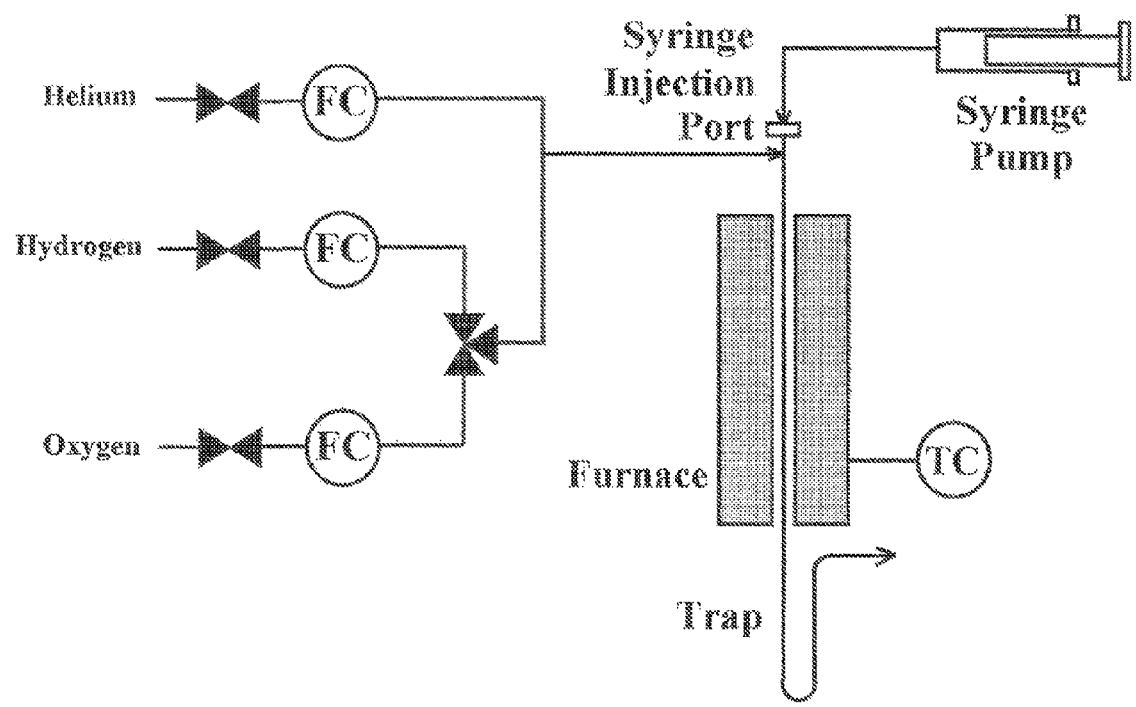
FIG. 5A demonstrates an exemplary pulse reactor setup used to crack oil extracted from algae.

Oil extracted from algae was cracked in a pulse reactor with a setup as shown in FIG. 5A. Fresh zeolite β catalyst as described herein was used for each cracking experiment and dried prior to use. The cracking experiments were performed at 500, 450, 400, 350, and 300° C. The cracking products were analyzed by GC/MS. Peaks were then identified by a combination of retention time and library search using a NIST MS fingerprint database. Peaks that could not be identified by the MS fingerprint or GC retention time were labeled as unknown.

Oil was extracted from algae via $CO_2$ and provided a first crude sample. Some of the crude algal oil was refined by an RBD process to provide a second refined sample. Each sample was cracked at 500, 450, 400, and 350° C. cracking condition temperatures.

Figure 5B:
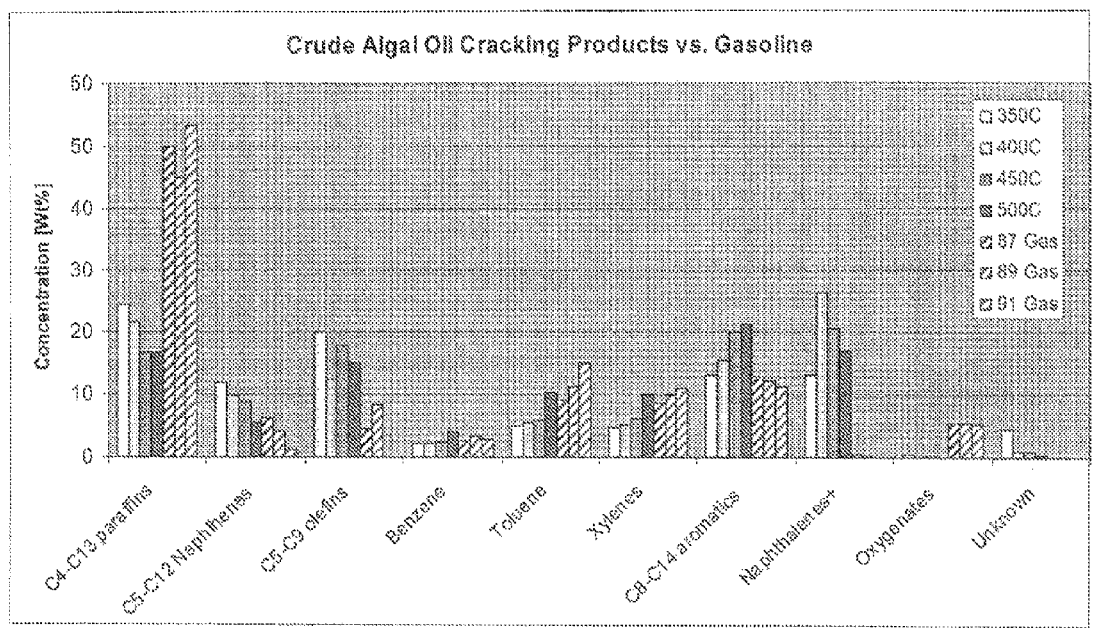
FIG. 5B shows the products resulting from cracking crude algal oils.

The crude algal oil cracked to approximately equal amounts of paraffins, olefins, C8-C14 aromatics, and naphthalenes as shown in FIG. 5B using the processes described herein wherein 0.1 g crude algal oil was cracked in contact with 0.1 g zeolite beta at various temperatures. The C4-C13 paraffins and naphthalenes averaged 19% of the products, while the naphthenes and the olefins averaged 16%. Methylbutane was the primary product at all temperatures, comprising about 9% of products. Paraffin, naphthene, and olefin production decreased with increasing cracking temperatures. Benzene, toluene, xylene, and C9-C14 aromatic content increased with the cracking temperature. Naphthalene production peaked at 400° C. Oxygenates of indeterminate structure were less than 1% of the products at all temperatures. As a result, water was expected to be a significant reaction product; however, water was not quantified using these specific procedures. The unknowns at 350° C. resulted from the inability to identify 18 peaks, each contributing between 0.1- 0.5% to the total concentration.

FIG. 5B also demonstrates the components of 87, 89, and 91 octane gasoline as taken from a standard gasoline station. Compared to petroleum gasoline, the products from the crude algal extract contained significantly fewer paraffins and more naphthalenes. Gasoline also tends to have smaller molecules than the cracking algae oil products that were observed. For example, paraffins in gasoline were C4-C10, but the paraffins in the cracking products ranged up to C13. This trend held true for the naphthenes, olefins, and C8-14 aromatics as well.

Figure 5C:
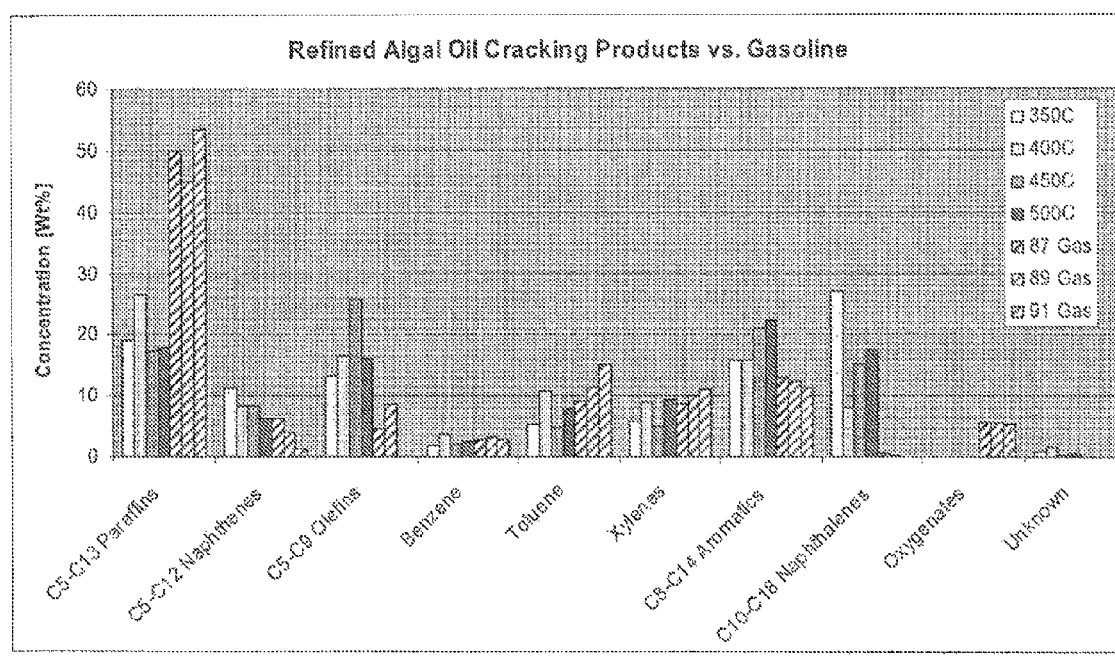
FIG. 5C shows the products resulting from cracking refined algal oils.

A second sample of algal oil was cracked by a process of the example, wherein the second sample was refined by an RBD process prior to cracking 0.1 g of the second sample over 0.1 g zeolite β. FIG. 5C shows that paraffins were the principal cracking product of refined algal oil, averaging 20% across all temperatures. Olefins, C8-C14 aromatics, and naphthalenes all averaged around 18%. Benzene averaged 2.5% of products across all temperatures with a maximum of 3.8% at 400° C. No oxygenates were identified from cracking the refined oil, but water was most likely present. Less than 1% of peaks, on average, were unidentified. Naphthene content decreased with increasing temperature while C8-C14 aromatic species increased.

Figure 5D:
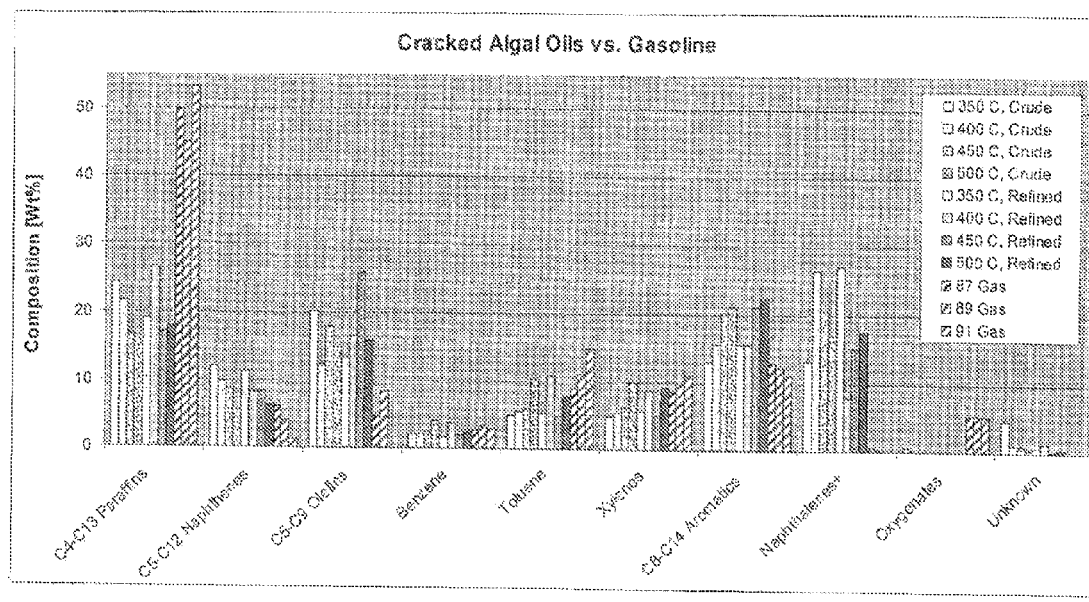
FIG. 5D demonstrates a comparison of the cracked products from both crude and refined algal oil to 87, 89, and 91 octane petroleum gasoline.

The cracking products from the refined algal oil were similar to the crude oil cracking products. Also, the toluene and xylene content are lower in comparison to the gasoline samples of the example. FIG. 5D compares the cracked products from both the crude and the refined algal oil to 87, 89, and 91 octane petroleum gasoline. On average, there is no significant difference between the two sets of products obtained by cracking the algal oil samples, suggesting that RBD refining does not enhance the cracking products. In some instances, the cracking products may require conventional fractionation refining in order to produce a suitable gasoline product. In other instances, the cracking products may be used as a fuel product, component, or additive.

EXAMPLE 6

Farnesene, a sesquiterpene, was cracked by contacting farnesene with the LZY-72 catalyst that was the same ammonium-exchanged form used in previous cuparene cracking examples. This material converts to the acidic (protonated) form upon heating during the pretreatment process at 500° C.

The cracking products were analyzed by GC/MS. The chromatograms tended to be very complicated due to the wide array of cracking products, particularly at lower temperatures. Only peaks with areas at least 1% of the largest peak's area on the chromatogram were analyzed for this report. The smaller peaks tended to contribute about 0.3% each to the total number area of all peaks on a chromatogram. Retained peaks were then identified by a combination of retention time and library search using a NIST MS fingerprint database. Peaks that could not be identified by the MS fingerprint or GC retention time were labeled as unknown.

Farnesene was concentrated to 61% by repeatedly injecting 25 uL into a preparative GC column until 2 mL of enriched farnesene was collected, the composition of which is shown in Table 3.

TABLE 3

| Component | Wt. % |
| --- | --- |
| Farnesene | 61.4 |
| Bisabolene | 11.2 |
| Unknowns | 10.3 |
| Curcumene | 7.8 |
| α-Cedrene | 2.2 |
| δ-Guaiene | 2.2 |
| 5,5-dimethyl-1-propyl-1,3-Cyclopentadiene | 1.7 |
| 2-Methyl-3-(3-methyl-but-2-enyl)-2-(4-methyl-pent-3-enyl)-oxetane | 1.6 |
| Caryophyllene | 1.6 |

The enriched farnesene was cracked over LZY-72 catalyst.

Figure 6A:
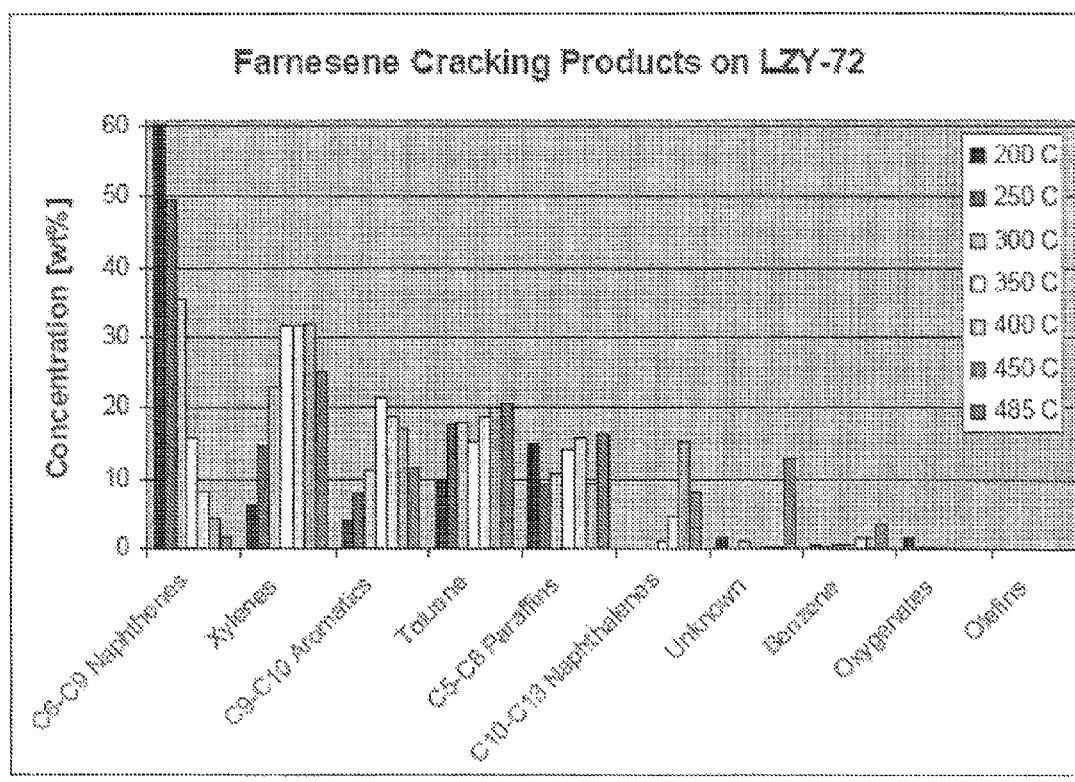
FIG. 6A shows the cracking products of farnesene at various reaction temperatures using LZY-72 zeolite catalyst.

In aggregate, cracking farnesene with the LZY-72 catalyst produced 60% aromatic molecules, 25% naphthenes, and 13% paraffins. Cracking produced primarily naphthenes between 200 and 300° C. and aromatics at higher temperatures, as shown in FIG. 6A. Methyl and dimethylcyclohexane were the primary naphthenes at cracking conditions between 200 and 300° C., comprising 21% and 17% each of all naphthenes. Naphthene production decreased with increasing cracking temperatures, as shown in FIG. 6A. Xylene, C9-C10 aromatics, naphthalene, and benzene content increased with the cracking temperature. Trimethylbenzene was the primary C9-C10 aromatic molecule, averaging 63% of the C9-C10 aromatic molecules across all temperatures. Benzene reached 1.5% of all products at 400° C. and peaked at 3% when cracking farnesene at 490° C. Toluene and paraffins were produced relatively consistently at all temperatures, averaging 17% and 12% each, respectively. Oxygenates of indeterminate structure were less than 2% of the products at all temperatures. No significant amounts of olefins were detected. The increase in unknowns at 485° C. resulted from the inability to identify four peaks, each contributing between 1-3% to the total concentration.

The increasing tendency for farnesene to crack into aromatic products as cracking temperature increases is consistent with the trends seen in the other sesquiterpene cracking examples. In general, the sesquiterpenes cracked using LZY-72 produced more xylenes and benzene at the cost of naphthenes as cracking temperature increased.

Figure 6B:
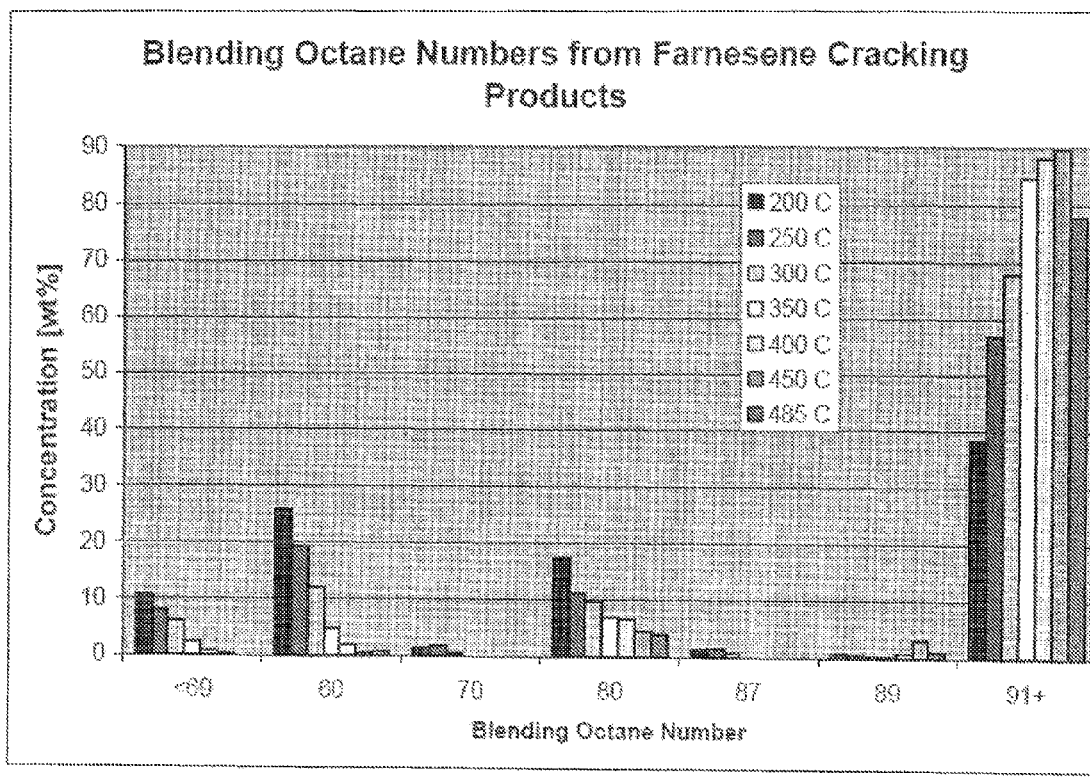
FIG. 6B shows the blending octane numbers of farnesene cracking products.

FIG. 6B shows the average of the research and motor blending octane numbers for the species found in the farnesene cracking products. The 91+ column contains methylbutane, methylcyclopentane, methylcyclohexane, and the aromatic molecules, except benzene. All the other naphthenes and paraffins had octane numbers more similar to base petroleum gasoline blend stocks or straight run gasoline, which has an octane number between 60 and 70.

Cracking farnesene at 350+° C. produced better than 75% products with high blending octane numbers, for example, above 90. The high octane products from farnesene cracking at 350+° C. suggest that the overall mixture could have a high octane number. As demonstrated by this example, a process of cracking farnesene and the composition resulting therefrom can be a useful fuel product, component, or additive, the composition resembles base petroleum gasoline feed stocks (octane numbers 60-80) and higher octane blending feed stocks (octane number 91+).

EXAMPLE 7

An exemplary process of cracking a mixture of sesquiterpenes was carried out in this example. Ginger oil contains about 80% sesquiterpenes. Zingiberene makes up 36% of ginger oil. The next largest component, at 16%, is beta sesquiphellandrene. Curcumene, farnesene, and bisabolene are also present at about 10% each. Ginger oil that was cracked in this example was obtained using carbon dioxide to minimize the amount of gingerol, which represented about 6% of the oil.

The LZY-72 catalyst used for the cracking of ginger essential oil was the same ammonium-exchanged form used in previous cuparene cracking examples. This material converts to the acidic (protonated) form upon heating during the pretreatment process at 500° C.

Figure 7:
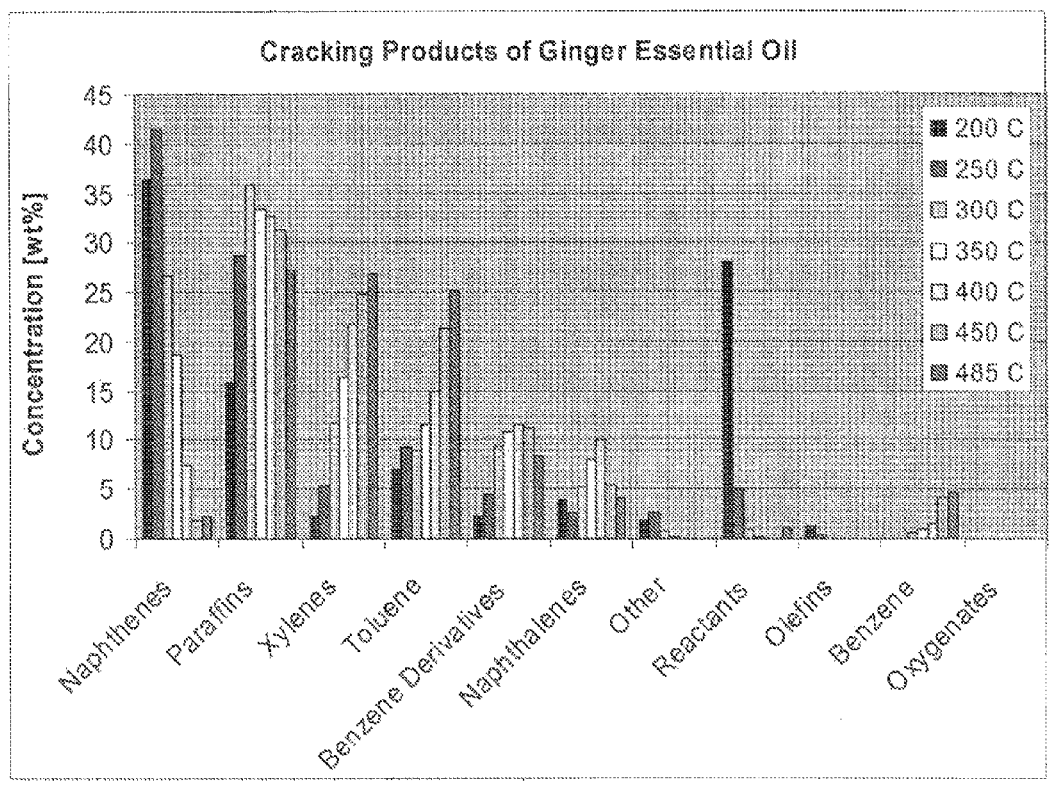
FIG. 7 shows the cracking products of ginger essential oil at various reaction temperatures using LZY-72 zeolite catalyst.

Ginger oil was cracked similar to the methods of the previous examples in a pulse reactor under catalytic cracking conditions and contacting the ginger oil with a catalytic composition. About half of the ginger oil cracked into paraffins and naphthenes. Higher cracking temperatures enhanced production of aromatic compounds at the cost of naphthenes and some paraffins. Thus, benzene formation increased from nil at 200-250° C. to about 5% at 485° C. Olefins reached 1.5% of cracking products at 200° C. and were not detected at higher temperatures. Oxygenates were not positively identified in any cracking products. FIG. 7 demonstrates the composition of cracking products from a process of cracking a mixture of sesquiterpenes, in this example, ginger oil. Cracking ginger essential oil yields a good variety of naphthenes, paraffins, xylenes, and benzene derivatives at 300° C. Many of the paraffins are branched and provide a high octane number.

EXAMPLE 8

Squalene is an exemplary triterpene. Processes as described herein were utilized to crack squalene. The LZY-72 catalyst used for the cracking of squalene was the same ammonium-exchanged form used in previous cuparene and farnesene cracking examples. This material converts to the acidic (protonated) form upon heating during the pretreatment process at 500° C. The cracking products were analyzed by GC/MS. The chromatograms tended to be very complicated due to the wide array of cracking products, particularly at lower temperatures. Only peaks with areas at least 1% of the largest peak's area on the chromatogram was analyzed for this report.

Figure 8A:
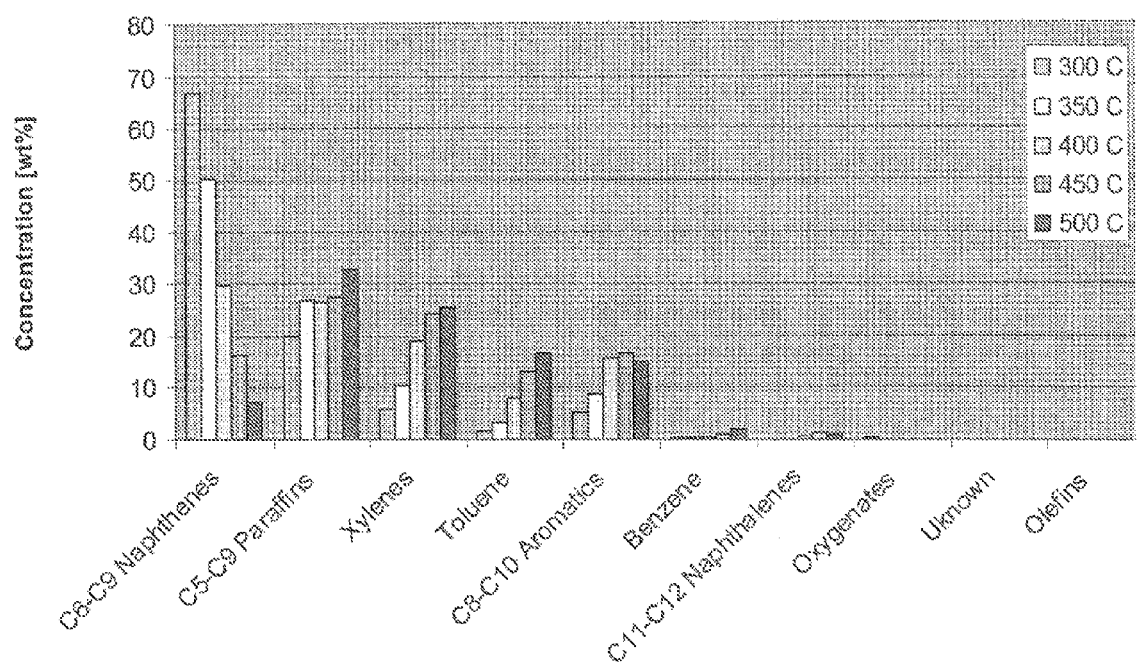
FIG. 8A shows the cracking products of squalene at various reaction temperatures using LZY-72 zeolite catalyst.

The cracking products are shown in FIG. 8A, and demonstrate similar products to those observed in previous cracking examples: more naphthene at lower temperatures and more aromatics at higher temperatures. Additionally, GC/MS results show appreciable amounts of benzene only at high temperatures (>450° C.), and negligible amounts of oxygenates and olefins.

Figure 8B:
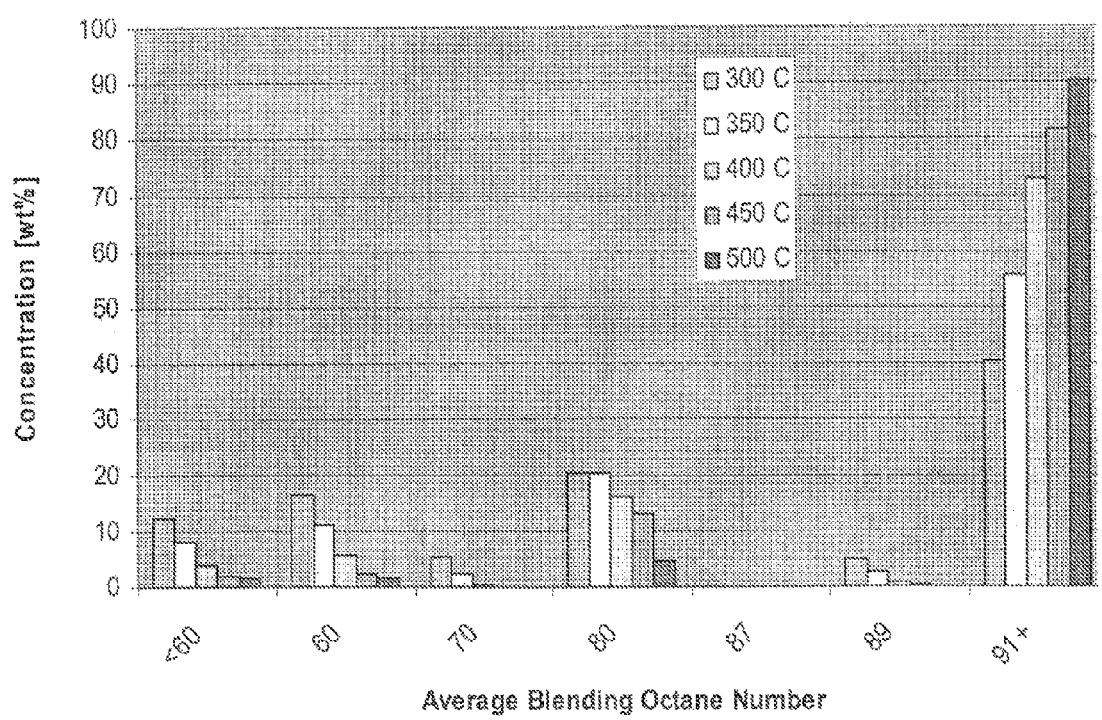
FIG. 8B shows the blending octane numbers of squalene cracking products.

The octane number of the cracked products is shown in FIG. 8B, indicating the average blending octane numbers of the product. The higher blending octane numbers at the higher temperatures are indicative of the higher aromatic concentration of the product. The higher concentration of lower octane numbers at lower temperatures results from low octane number cyclic compounds.

EXAMPLE 9

Figure 9A:
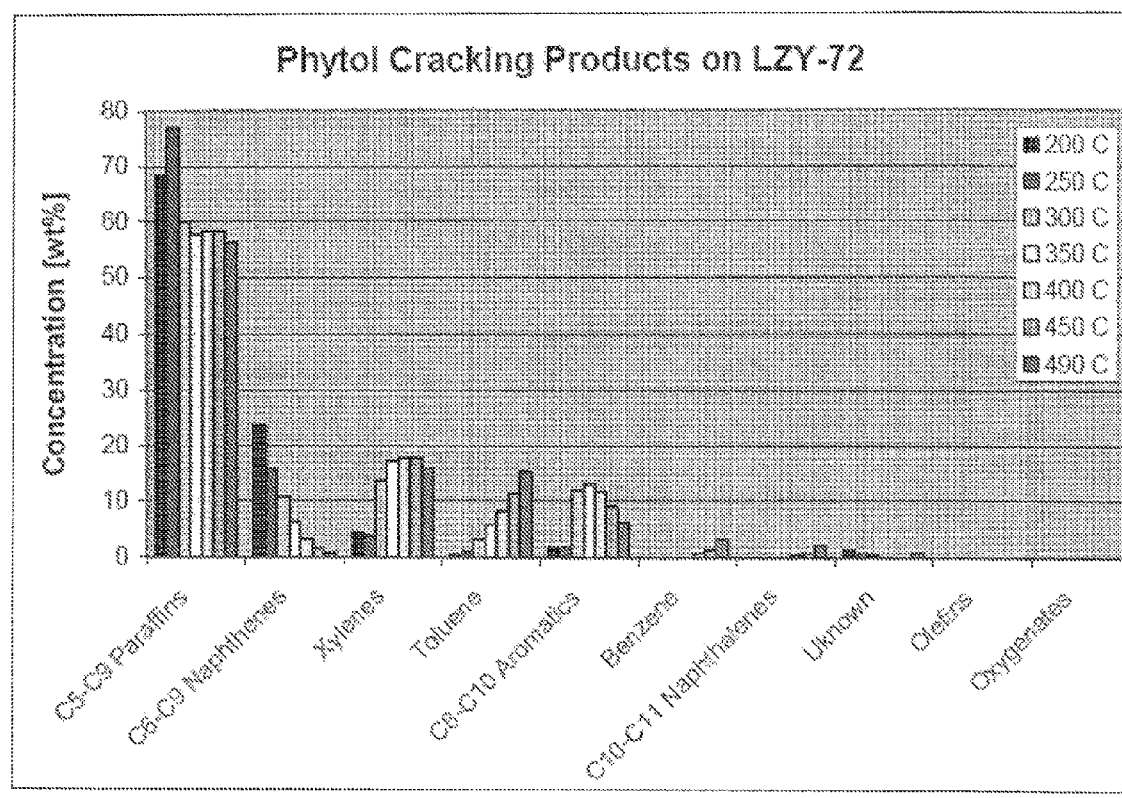
FIG. 9A shows the cracking products of phytol at various reaction temperatures using LZY-72 zeolite catalyst.

Phytol is a diterpene that is often found in photosynthetic organisms. Phytol can be the product of the degradation of chlorophyll. FIG. 9A shows that paraffins were the principal cracking product of phytol, averaging 62% across all temperatures. The naphthenes decreased from 24% at 200° C. to about 1% at 490° C. The aromatic content of the cracking products increased with temperature from 7% to 42% of all products. Benzene and naphthalene concentrations reached 3% and 2%, respectively, of all products at 490° C. No olefins or oxygenates were identified from cracking phytol.

Figure 9B:
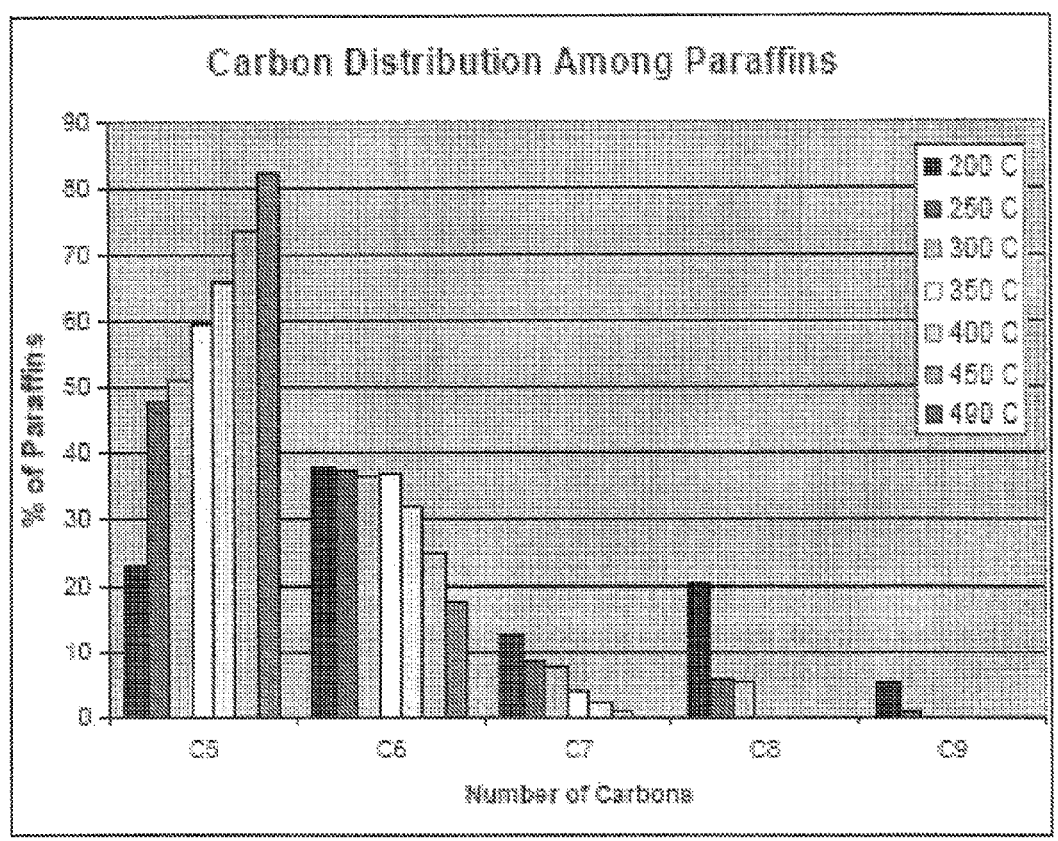
FIGS. 9B and 9C show the carbon distribution and the degree of branching, among the paraffins products of phytol cracking.
Figure 9C:
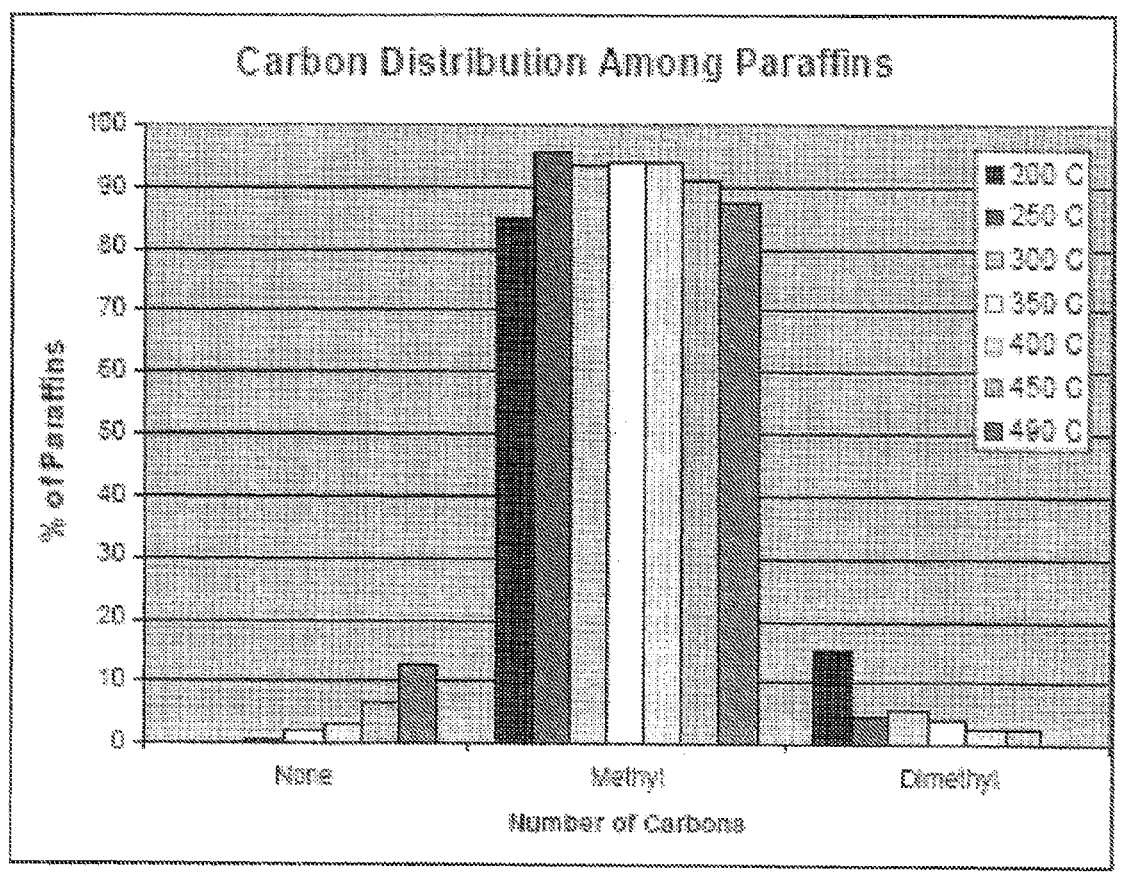

FIGS. 9B and 9C show the carbon distribution and the degree of branching, respectively, among the paraffins. Low cracking temperatures favor production of C6-C8 paraffins, such as methylpentane and methylheptane, while higher temperatures produce predominantly methylbutane. Many of the paraffins produced by cracking phytol were mono-methyl, as shown in FIG. 9C, although there is some tendency towards formation of normal and dimethyl paraffins at 200° C. and 490° C., respectively.

Figure 9D:
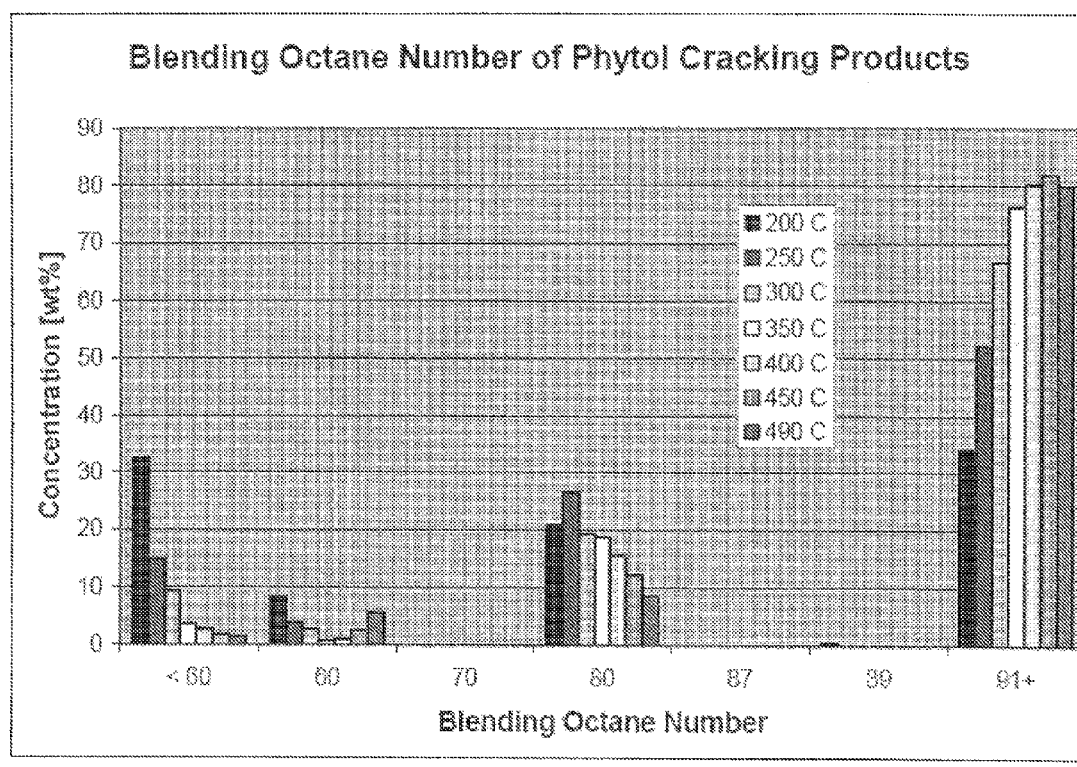
FIG. 9D shows the blending octane numbers of phytol cracking products.

The octane blending numbers of most phytol cracking products were similar to those derived from farnesene. FIG. 9D groups the molecules according to the average of the research and motor blending octane number. The high octane number molecules in the 91+ column consist of the aromatic species, methylbutane, methylcyclopentane, and methylcyclohexane.

EXAMPLE 10

The LZY-72 catalyst used for the cracking of algal phytol was the same ammonium-exchanged form used in previous examples. Cracking was only conducted for a single temperature of 350° C., chosen because it was the expected those conditions ensure little or no benzene production. The cracking products were analyzed by GC/MS as discussed in previous examples. Afterward, the compositions of cracked phytol were compare with samples of 87, 89, and 91 grade gasoline purchased at a retail gas station in Tulsa, Okla.

Six samples were investigated reported in this example: the products of a single pulse of phytol which originated from algae. Phytol was extracted from the algae and is referred to as "Algal Phytol Extract"; the products of a single pulse of phytol which originated from a commercial supplier (Sigma-Aldrich) and is referred to as "Commercial Phytol"; the products of multiple pulses of the commercial phytol which were collected into about a ½ cc product sample and encapsulated in a glass vial and is referred to as "Vial of Commercial Phytol"; a sample of 87 octane gasoline; a sample of 89 octane gasoline; and a sample of 91 octane gasoline.

Figure 10A:
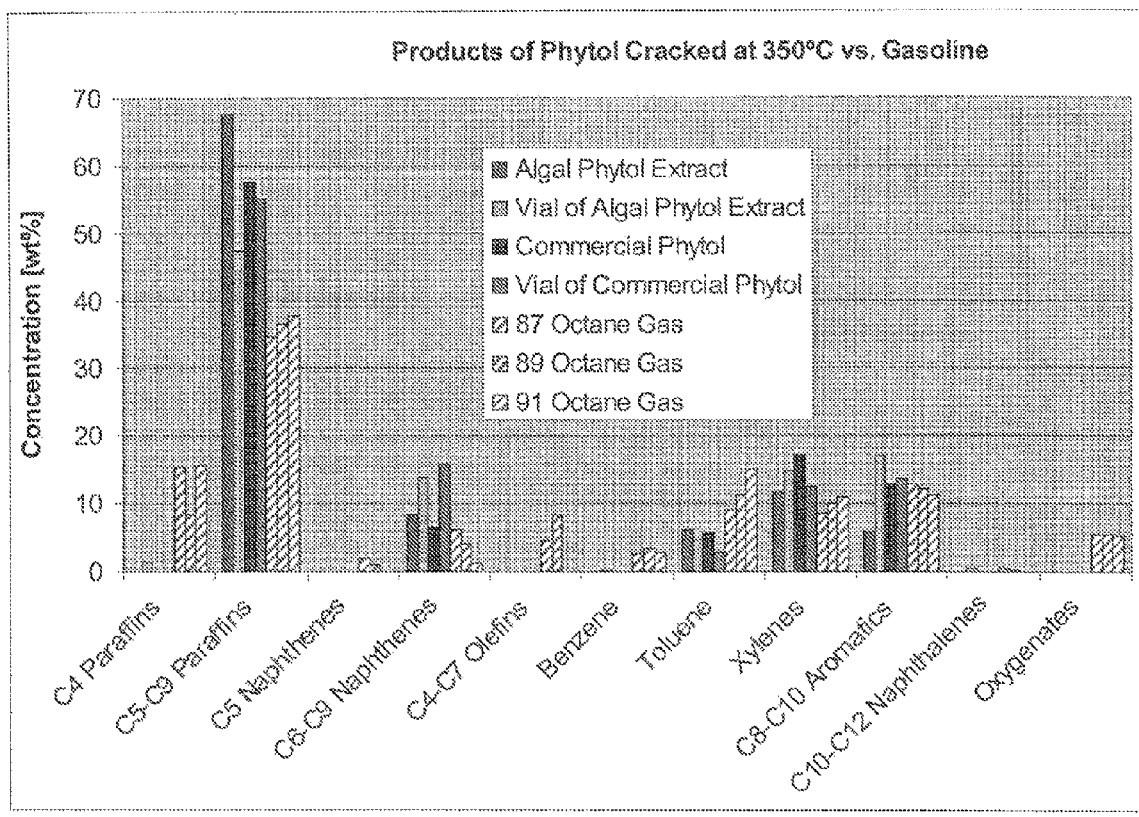
FIG. 10A shows the cracking products of the cracking products of phytol from both commercial and algal sources, as compared to the hydrocarbon components of the commercial gasoline samples.

The samples of phytol were cracked in a pulse reactor in contact with the LZY-72 catalyst as described herein. The cracking products of the phytol are shown in FIG. 10A and compared with the analyses of the gasoline samples. The cracked products from phytol show no C4 hydrocarbons in contrast to the samples of retail gasoline. C5-C9 paraffins are higher in the phytol products than the retail gasoline. Lower concentrations of toluene, oxygenates (the gasoline samples contain 5% ethanol), and benzene, are observed in the phytol products.

Figure 10B:
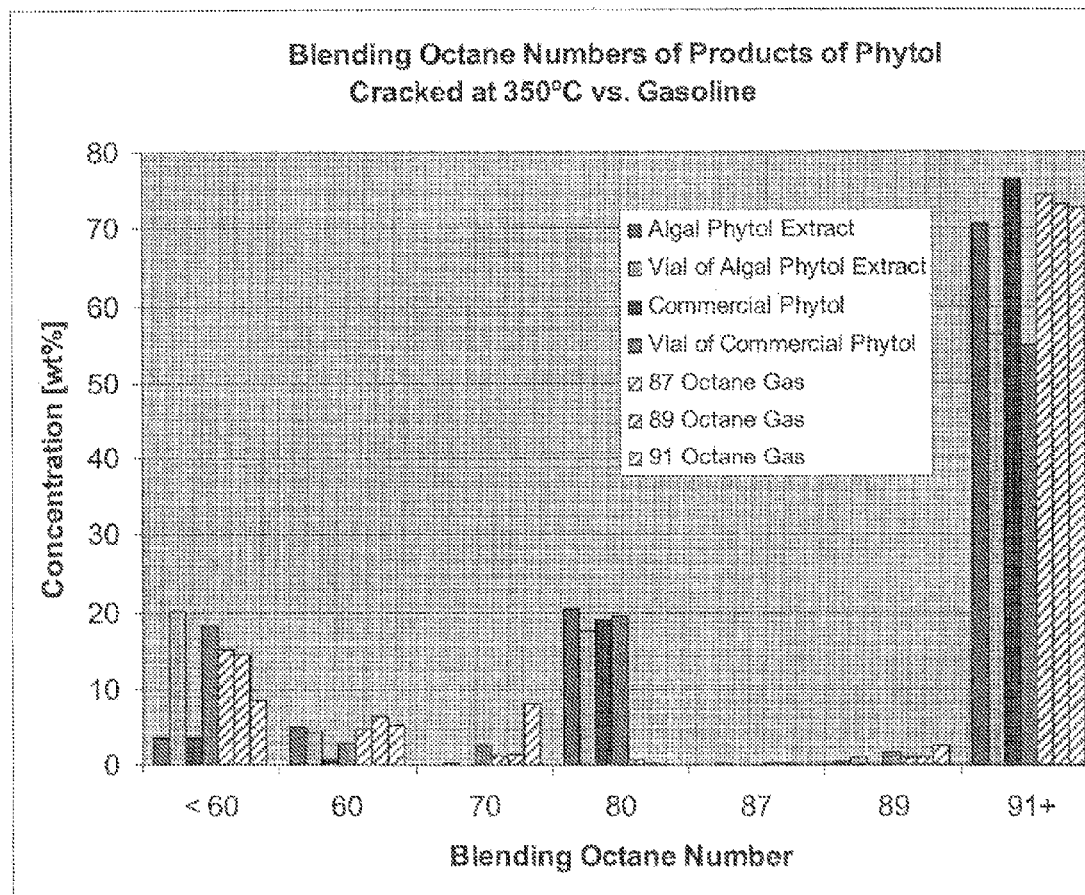
FIG. 10B shows the blending octane numbers of phytol cracking products as compared to commercial gasoline samples.

A comparison of the octane ranges of the 350° C. cracked phytol products to gasoline samples is shown in FIG. 10B. The vial of commercial phytol is the only sample significantly different from the others. It shows lower 91+ octane components, primarily as a result of its lower ethanol, benzene, and toluene concentrations. This could likely be corrected by adjusting the cracking temperature to 450° C. The difference in the larger sample in the vial from the single pulse samples is likely due to catalyst deactivation which can alter the product distribution.

EXAMPLE 11

Figure 11A:
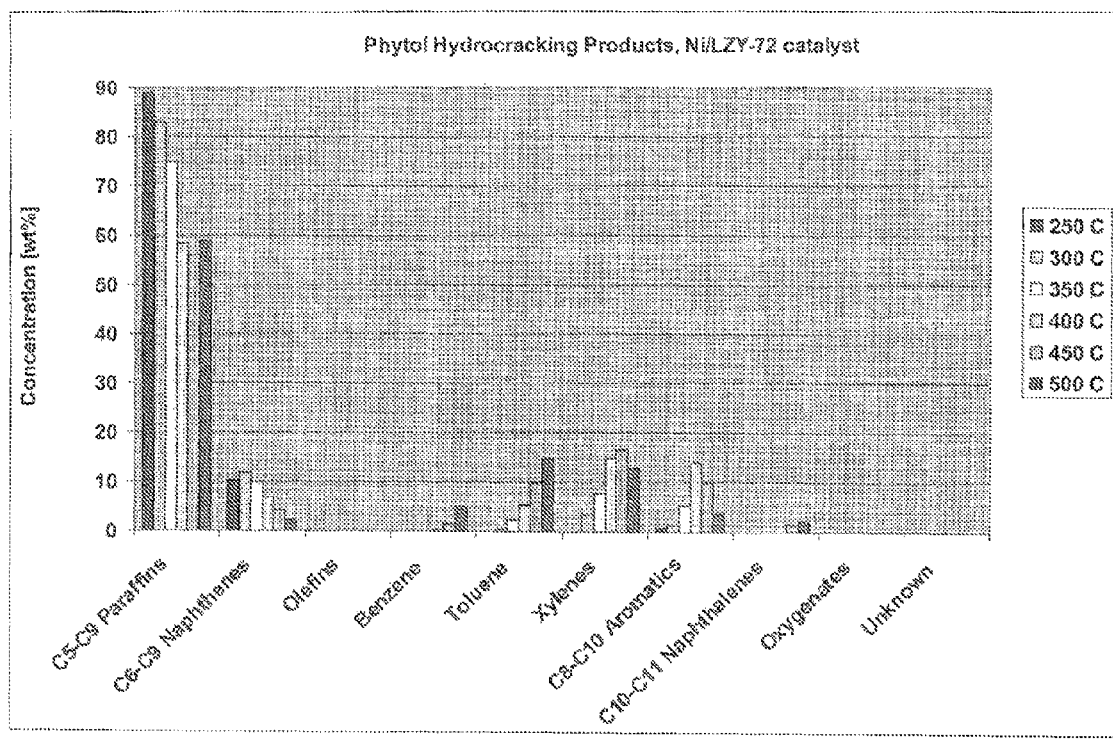
FIG. 11A shows the cracking and hydrocracking products of phytol at various reaction temperatures using Nickel/LZY-72 zeolite catalyst.
Figure 11B:
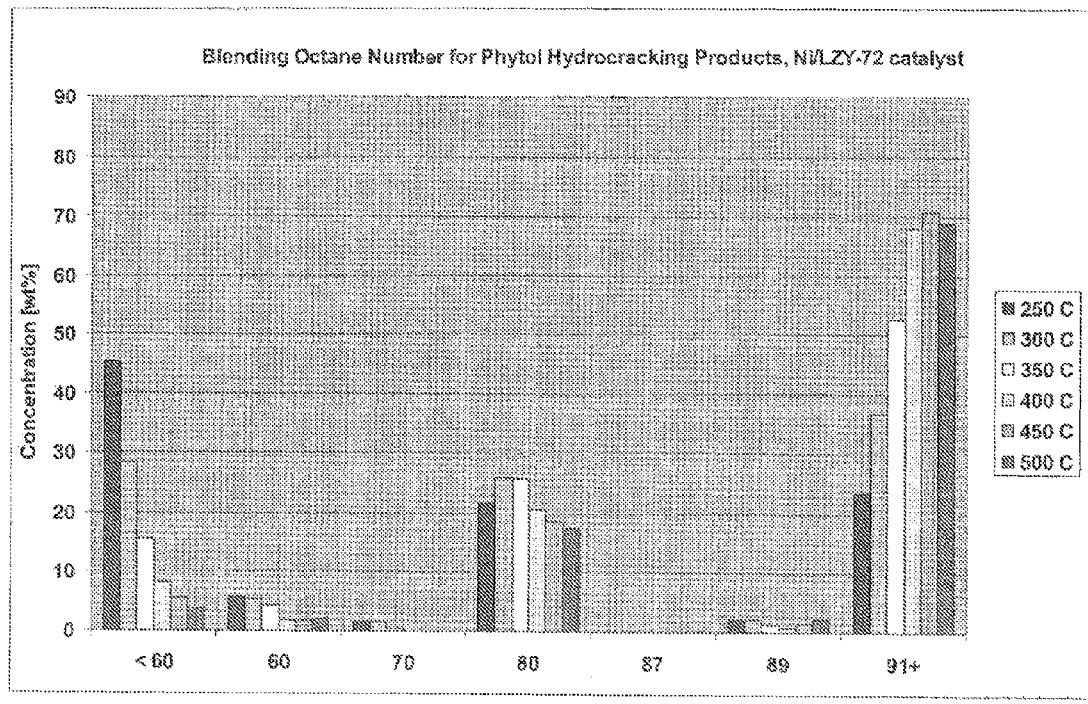
FIG. 11B shows the blending octane numbers of phytol hydrocracking products.

The LZY-72 catalyst used for other examples was partially ion-exchanged with Ni to produce Ni/LZY-72 which can be used as a hydrocracking catalyst. The ion-exchange procedure was as follows: 10.0 g of the ammonium form of LZY-72 was slurried in 50 g of water, and 2.4 g of Ni (II) acetate tetrahydrate was added. The mixture was stirred overnight at room temperature, then the solution was filtered off and the solid dried at 125° C. overnight. Catalysts such as these have both hydrogenation activity due to nickel and cracking activity due to the presence of protons. For pulse experiments, 0.5 g of this catalyst was placed in the pulse reactor, and it was activated under hydrogen flow at 300° C. for 1 hour prior to use. Hydrocracking was conducted using 25 µl pulses of phytol in hydrogen flow at 250, 300, 350, 400, 450, and 500° C. Products were trapped in liquid nitrogen, then washed out of the trap using methanol before analysis in the GC/MS system. The hydrocracking products of hydrocracking phytol are shown in FIG. 11A. Octane numbers of the products are illustrated in FIG. 11B.

EXAMPLE 12

This example describes macroscale preparation of fuel products derived from terpenes. In brief, squalene was successfully cracked using a tubular reactor to produce 1.37 gallons of liquid product. From this raw liquid product, 0.95 gallons of the lightest material was distilled and sent for ASTM gasoline analysis, which indicated the product has an octane number of 91.5.

Figure 12A:
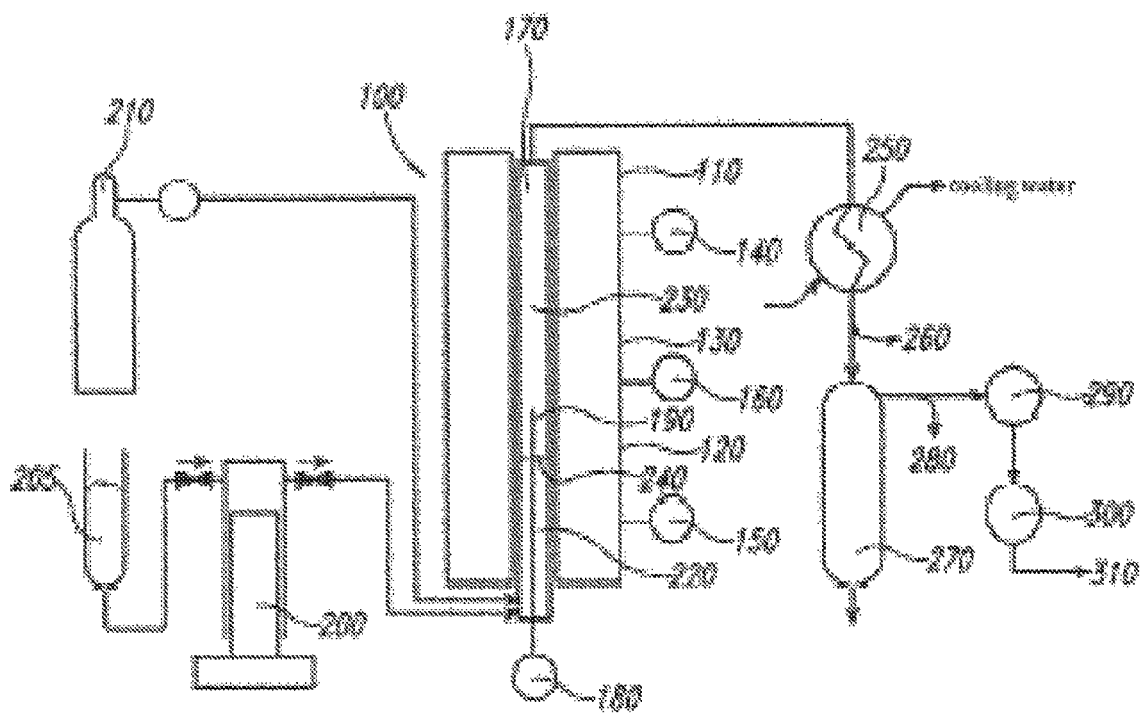
FIG. 12A shows schematically an apparatus suitable for large-scale cracking processes.

The cracking process was performed in a facility with a large furnace and tubular reactor set up in a hood. A simplified schematic of the apparatus is given in FIG. 12A. The three-zone furnace 100 includes an upper zone 110 and a lower zone 120 that are 6 inches long and 600 W each, and a middle zone 130 that is 12 inches long and 1180 W. Independent thermocouples 140, 150 and 160 measure each zone temperature, respectively. A 2-foot long tubular reactor 170 was mounted vertically within the threezone furnace 100. A thermocouple 180 is inserted axially into the catalyst zone 190 of the tubular reactor 170 measures the temperature at the center of the catalyst bed. A LabVIEW-based control program brings the furnace to isothermal conditions and the measured catalyst temperature to a set point. The same program also allows logging of all the measured system parameters including flow rates, temperatures, and pressures. An ISCO pump 200 feeds batches of up to 500 cc of liquid feed 205 to the reactor 170 at a constant, programmable rate. Flow controlled gas 210, in this case, nitrogen, can be co-fed into the reactor 170. While the majority of the cracking runs used a 1-inch OD tubular reactor packed with about 12 g of zeolite β (T-4546) extrudate (Süd Chemie); the first three runs using 500 cc of squalene reactant were conducted using a ¾-inch OD reactor filled with about 57 g of zeolite β (T-4546). As shown in FIG. 12A, liquid and gas flows enter the bottom of the tubular reactor 170 and mix as they flow through a preheating zone 220 packed with glass beads (3 mm diameters). The 18-inch long catalyst bed 230 sits above the bed of glass beads and the two are separated by a metal screen 240. Reactor products leaving the top flow through a coiled, concentric-tube heat exchanger 250 maintained at about 8° C. Cooled products exit the heat exchanger, pass through a valve arrangement which allows an instantaneous liquid sample to be collected 260 (known as a "line sample"), then they enter a cooled separator 270. Uncondensed gaseous products continue to a point where a small stream is tapped off to go to a micro-GC 280 which is dedicated to gas analysis, then on to a backpressure regulator 290, wet test gas flow meter 300, and vent 310. The backpressure regulator was set to about 5 psig for all runs.

Experiments of the example began by filling the reactor with a fresh catalyst bed of mass ~112 g. The reactor is then loaded into the furnace and heated overnight at 380-400° C. under nitrogen flow to dry the catalyst prior to reaction. The next morning, 500 cc of squalene is loaded into the ISCO pump, then nitrogen and squalene flows are set to 2 standard liters per minute (SLM) and 4 cc/min, respectively when the 1" OD reactor was used, or to 1 SLM and 2 cc/min when the ¾" OD reactor is used. Usually, the reaction temperature is set at 380° C. for the first 500 cc of squalene. The temperature is raised to 430° C. for the second 500 cc batch of squalene to offset losses in catalyst activity which occurs during the first 500 cc run. Including early runs where appropriate conditions were being established, all experiments are performed with reactor temperatures between 300 and 450° C., with all but two being between 380 and 450° C. The collection reservoir (containing the liquid products) is drained regularly, and line samples are taken regularly, and analyzed by GC as quickly as possible to ensure complete conversion of reactant.

When using the 1" diameter reactor with ~112 g of catalyst, once the second 500 cc of squalene had been processed (for a total of 1000 cc or 855 g); the reactor was cooled and the catalyst removed and replaced. In the case of 3 runs accomplished on the ¾" diameter reactor with 57 g of catalyst, the catalyst was changed after 500 cc of squalene had been cracked. Note that for either reactor, very close to the same ratio of squalene processed to catalyst charged was used.

When catalyst charges were removed from the reactor, a very small sample of catalyst was used in a microbalance system to determine coke content, then the remainder of the spent catalyst was placed in a horizontal tube furnace to be regenerated by burning in 80/20 Ar/$O_2$ at 575° C. for 4 hours. The burned catalyst was then subjected to n-propylamine thermal desorption analysis on the microbalance system to measure catalyst proton content which is directly correlated to structural integrity of the zeolite catalyst. Results of the n-propylamine thermal desorption analysis were compared to the virgin catalyst to ensure that the catalyst was still structurally sound and catalytically active. No significant damage to catalysts was detected after one full regenerative cycle. However, all the runs with squalene used fresh catalyst rather than regenerated. In total, 8.5 L or about 7268 g of squalene was processed and 1.37 gallons or about 4410 g of cracked liquid product was recovered.

A breakdown of the total products from the 7268 g of total squalene fed is given in Table 4.

TABLE 4

Global material balance.

| | Total grams | % of total squalene fed | % of total known products |
|---|---|---|---|
| Gaseous ($N_2$ free) | 2236 | 30.76 | 33.07 |
| Liquid | 4410 | 60.68 | 65.24 |
| Coke | 114 | 1.57 | 1.69 |
| Unaccounted for | 508 | 6.99 | — |

Figure 12B:
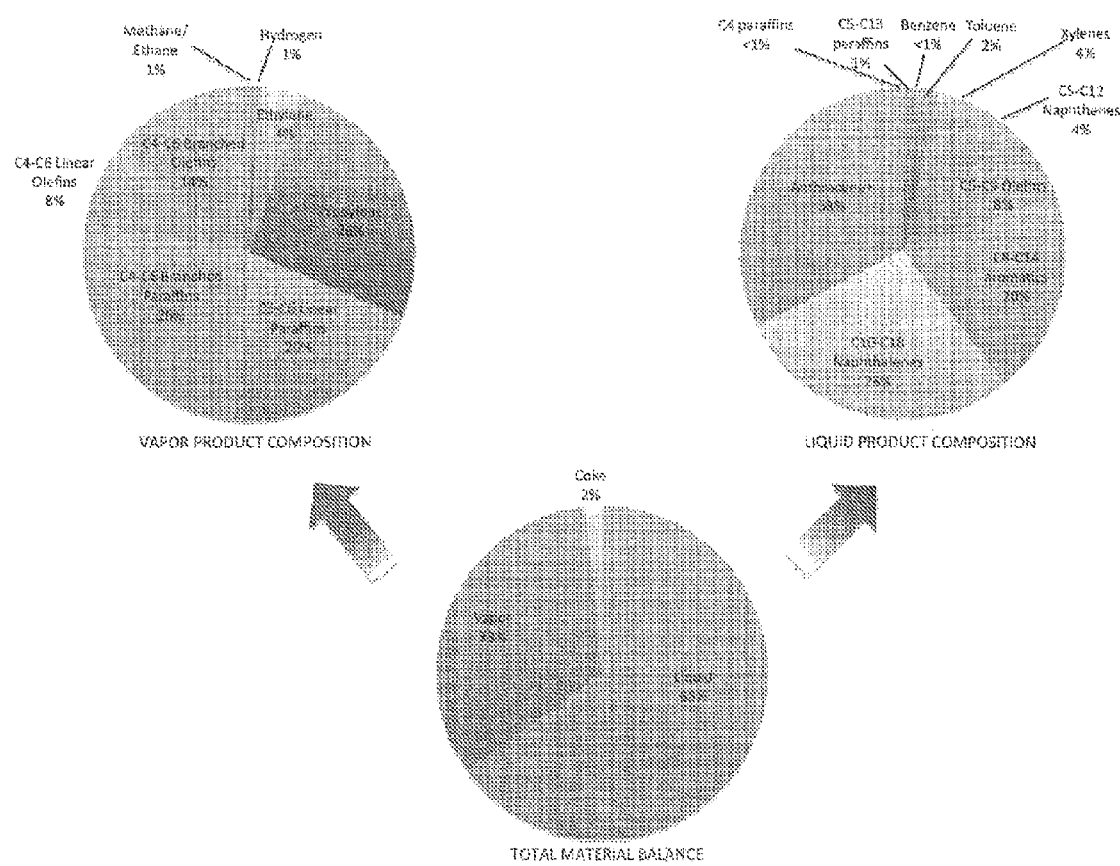
FIG. 12B shows the compositions of the gas and liquid products resulting from cracking squalene.

From the micro-GC, a detailed analysis of the gaseous product was integrated over time to yield a total amount of each gaseous product, and summed to give the total weight of gaseous rather than condensed products. The total weight of liquid collected was recorded as 4410 g. Coke was determined to be approximately 12% by weight on the spent catalyst, so this gives 13.44 g on 112 g of catalyst with a total of 8.5 separate batches of catalyst was used, yielding 114 g. Subtracting these numbers from 7268 g fed yields 508 g unaccounted for. The final column in FIG. 12B represents the percentages of total products which were actually collected and will be used in further analyses. Unaccounted material most likely went to sampling procedures and filling liquid lines.

A simulated distillation of the liquid product indicated that 58% of the liquid product was gasoline fraction (for example, boiling point less than 220° C.). Therefore, the cracked liquid product was distilled prior to ASTM testing. Collecting the gallon of product for ASTM analysis required boiling the products up to 275° C., well past the gasoline cut of 220° C. and this was not expected as the simulated distillation suggested more of the liquid was in the gasoline range. However, this was done to collect a gallon as a minimum amount required for the testing. The ASTM sample contained 3070 g of the cracking product nearest to the gasoline boiling range. The 1340 g of liquid too heavy to go in for gasoline testing remained and is termed "liquid resid". ASTM testing showed that the research octane number of the sample was 98.5 and the motor octane was 84.6 yielding a value of 91.5 for (R+M)/2 which is the usual octane number provided at the pump. Table 5 gives the fraction of squalene recovered into the various fractions. The detailed analysis of the vapor composition is an average of 3 experiments that were performed. The detailed liquid composition was derived from GC/MS analysis of a small sample from the pooled liquid cracking products.

TABLE 5

Overall yields from squalene.

| | Total grams | % of total squalene fed |
|---|---|---|
| Gaseous ($N_2$ free) | 2236 | 33.07 |
| ASTM sample | 3070 | 45.41 |
| Liquid resid (>275° C.) | 1340 | 19.83 |
| Coke | 114 | 1.69 |

FIG. 12B demonstrates the compositions obtained when cracking squalene in a flow reactor in the current example. A detailed analysis of gaseous products is demonstrated in Table 6. Because isobutane and isopentane have blending research octane numbers of 122 and 100, respectively, a reasonable estimate for the octane number of the liquid product can be computer that would be obtained if the quantities of isobutane and isopentane which appear in Table 6 were included in the liquid product. The research octane number would be approximately 100.8 and the motor octane number 88.8 yielding (R+M)/2=94.8. Note also that if isobutane (representing 5.02% of the squalene converted) and isopentane (representing 2.24% of the squalene converted) were recovered and added to the sample recovered for the ASTM analysis, the yield would go up 7.26% to 52.67% of the squalene converted to the sample recovered for the ASTM analysis. If all of the C4+ components of the gas phase were recovered and added back to the sample recovered for the ASTM analysis, the yield would have increased by 22.5 percentage points to 67.91% and since blending octane numbers for C4 and C5 olefins range from about 109 to 176, therefore further significant improvements in the octane number could be realized, possibly to even over 100 octane.

TABLE 6

Detailed gaseous product composition

| | Wt % of gaseous product | Wt % of squalene reactant |
|---|---|---|
| Hydrogen | 0.59 | 0.19 |
| Methane | 0.91 | 0.30 |
| Ethylene | 3.56 | 1.18 |
| Ethane | 0.67 | 0.22 |
| Propylene | 21.74 | 7.19 |
| Propane | 4.46 | 1.47 |
| Trans-2-butene | 5.54 | 1.83 |
| 1-Butene | 3.60 | 1.19 |
| Isobutene | 9.67 | 3.20 |
| Cis-2-butene | 4.26 | 1.41 |
| Isobutane | 15.19 | 5.02 |
| n-Butane | 9.97 | 3.30 |
| Trans-2-pentene | 1.98 | 0.65 |
| 2-Methyl-2-butene | 4.51 | 1.49 |
| 1-Pentene | 3.29 | 1.09 |
| Cis-2-pentene | 0.84 | 0.28 |
| Isopentane | 6.78 | 2.24 |
| n-Pentane | 0.86 | 0.29 |
| Hexanes plus | 1.57 | 0.52 |

The ASTM sample was sent for testing after being distilled to minimize the amount heavy cracking products in the sample. The results of the testing are given in Table 7, which also includes a column with the required standards from 2004. Many of the properties of the product meet the ASTM standards for retail gasoline. For example, the research octane (RON) and motor octane numbers (MON) were 96.5 and 84.6 respectively, for a (R+M)/2 of 91.5, all of which meet the required minimums of 91 RON and 82 MON for gasoline. Bold text in Table 7 indicates tests the sample failed. In general, the ASTM sample only failed tests related to the distillation profile. These failures were expected because material outside of the gasoline boiling point range had to be included to obtain the minimum sample volume of one gallon. The ASTM distillation results show that the distillation performed only removed the highest boiling point components (for example, anthracenes), but left additional heavy components (for example, naphthalenes and poly-substituted benzenes). This led to a final boiling point of 260° C., which was 35° C. higher than the allowable maximum for retail gasoline. The drivability index is calculated from the temperatures at which 10, 50 and 90% of the sample was recovered and gauges how well the fuel will perform when starting, idling, and driving. As expected, the sample drivability index exceeded the allowable maximum because the distillation curve exceeded specified boiling points. The example demonstrates a gallon of liquid product from squalene for ASTM testing.

TABLE 7

ASTM results for the gasoline fraction from squalene cracking. Failed tests in bold

| Parameter | Method, Regulatory Reference | Squalene Cracking Product Measurement | Standard/Regulatory Requirement (ASTM D4814-04a) |
|---|---|---|---|
| API Gravity @ 60° F. | ASTM D4052-02e1 | 35.1 | |
| Appearance in Laboratory | ASTM D4176-04e1 P1 | C + B | Clear & Bright |
| Phosphorous Content (g/gal) | ASTM D3231-07 | 0.891 | 0.005 MAX |
| Sulfur Content | ASTM D5453-08a*, 40 CFR, title 40, subpart H. | 3.8 ppm | 120 ppm |
| Appearance | Visual | Pass | |
| Oxidation Stability | ASTM D525-05 | 60.52 minutes | 240 minutes MIN |
| Existent Gum (unwashed) (mg/100 mL) | ASTM D381-04e1 | <0.5 | 5 MAX |
| Existent Gum (washed) (mg/100 mL) | ASTM D381-04e1 | <0.5 | 5 MAX |
| Mercaptan Sulfur (wt %) | ASTM D3227-04a | <0.002 | 0.035 MAX |
| Octane Number- Research | ASTM D2699-07a | 98.5 | |
| Octane Number- Motor | ASTM D2700-07b | 84.6 | 82 |
| AKI—Anti-Knock Index, = (RON + MON)/2 | | 87 (regular) 89 (mid-grade) 91+ (premium) | 91.5 |
| Silver Corrosion (3 hrs.@122° F.) | ASTM D4814-07b A1 | 1 | |
| Copper Corrosion (3 hrs. @122° F.) | ASTM D130-04e1 | 1B | 1 |
| Nace Corrosion | TMO172-01 | B | |
| Benzene Content (vol %) | ASTM D3606-07; 40 C.F.R 80.1220, 80.1230 | 0.34 | 4 MAX (In 2011, will be 0.62 Vol % MAX) |
| Oxygen Content (wt %) | ASTM D4815-04 | 0.08 | 1 MAX |
| MTBE (vol %) | ASTM D4815-04 | <0.1 | |
| V/L-20° F. | ASTM D4814-06a | 199 | 20 MAX |
| Vapor Pressure @ 100° F. (psi) | ASTM D5191-07-EPA | 2.94 | 7.8-15 MAX[1] |
| Drivability Index (° F.) | ASTM D4814-07b | 1749 | 1200-1250 MAX[1] |
| Distillation | ASTM D86-07b | | |
| IBP | | 117.6° F. (47.5° C.) | |
| 10% | | 207.1° F. (97.3° C.) | 50-70° C. MAX[1] |
| 30% | | 270.3° F. (132.4° C.) | |
| 50% | | 324.8° F. (162.7° C.) | 66-77° C. ⇒ 110-121° C. (MIN ⇒ MAX)[1] |
| 70% | | 394.8° F. (201.6° C.) | |
| 90% | | 463.6° F. (239.8° C.) | 185-190° C. MAX[1] |
| 95% | | 489.2° F. (254.0° C.) | |

TABLE 7-continued

ASTM results for the gasoline fraction from squalene cracking. Failed tests in bold

| Parameter | Method, Regulatory Reference | Squalene Cracking Product Measurement | Standard/Regulatory Requirement (ASTM D4814-04a) |
|---|---|---|---|
| | End Point | 500.0° F. (260.0° C.) | 225° C. MAX |
| | Recovered | 95.5% | |
| | Residue | 2.3 vol % | 2 vol %MAX |
| | Loss | 2.2% | |

The invention claimed is:

1. A catalytic cracking process for cracking oil from algae comprising, extracting oil from algae to form a feedstock comprising at least one cuparene, farnescene, phytol and squalene; and contacting said feedstock with a first catalytic composition comprising a large pore molecular sieve, wherein the large pore molecular sieve is a 12-ring zeolite.

2. The method of claim 1, wherein said algae is genetically modified to increase production of cuparene, farnescene, phytol or squalene as compared to a non-genetically modified algae.

3. The process of claim 1, wherein the cracking conditions comprise heating the feedstock to between about 100-1000° C.

4. The process of claim 3, wherein said catalytic cracking conditions comprise heating the feedstock to a temperature between about 180 and 580 C.

5. The process of claim 4, wherein said catalytic cracking conditions comprise heating the feedstock to a temperature between about 200 and 400° C.

6. The process of claim 5, wherein said catalytic cracking conditions comprise heating the feedstock to a temperature between about 350 and 400° C.

7. The process of claim 1, wherein the large pore molecular sieve has a pore size greater than 6 Angstroms.

8. The process of claim 7, wherein the large pore molecular sieve has a cage diameter of 10-15 Angstroms.

9. The process of claim 1, wherein the large pore molecular sieve is a β, L, or Y-type zeolite.

10. The process of claim 9, wherein the molecular sieve is LZY-72, Valfor CP811BL-25, ELZ-L, or T-4546, 11. The process of claim 1, wherein said process further comprises a second catalytic composition that is different from the first catalytic composition.

12. A catalytic cracking process for cracking oil from algae comprising, extracting oil from algae to form a feedstock comprising a carotene; and contacting said feedstock with a first catalytic composition comprising a large pore molecular sieve, wherein the large pore molecular sieve is a 12-ring zeolite.

13. The process of claim 12, wherein the cracking conditions comprise heating the feedstock to between about 100-1000° C.

14. The process of claim 13, wherein the catalytic cracking conditions comprise heating the feedstock to a temperature between 180 and 580° C.

15. The process of claim 14, wherein the catalytic cracking conditions comprise heating the feedstock to a temperature between 200 and 400° C.

16. The process of claim 15, wherein the catalytic cracking conditions comprise heating the feedstock to a temperature between 350 and 400° C.

17. The process of claim 12, wherein the large pore molecular sieve has a pore size of greater than 6 Angstroms.

18. The process of claim 17, wherein the large pore molecular sieve has a cage diameter of 10-15 Angstroms.

19. The process of claim 12, wherein the large pore molecular sieve is a β, L, or Y-type zeolite.

20. The process of claim 19, wherein the molecular sieve is LZY-72, Valfor CP811BL-25, ELZ-L, or T-4546.

* * * * *